US012616817B2

(12) United States Patent
Burkholz et al.

(10) Patent No.: US 12,616,817 B2
(45) Date of Patent: May 5, 2026

(54) INTRAVENOUS CATHETER SYSTEMS AND METHODS

(71) Applicant: Becton, Dickinson and Company, Franklin Lakes, NJ (US)

(72) Inventors: Jonathan Karl Burkholz, Salt Lake City, UT (US); Bin Wang, Irvine, CA (US); Ralph L. Sonderegger, Farmington, UT (US); Joseph Spataro, Cottonwood Heights, UT (US); Shaun Staley, Murray, UT (US); Tyler Warner, Bluffdale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/670,298

(22) Filed: Feb. 11, 2022

(65) Prior Publication Data

US 2022/0161005 A1 May 26, 2022

Related U.S. Application Data

(62) Division of application No. 15/969,584, filed on May 2, 2018, now Pat. No. 11,278,705.

(Continued)

(51) Int. Cl.
*A61M 25/00* (2006.01)
*A61M 5/158* (2006.01)
(Continued)

(52) U.S. Cl.
CPC .... *A61M 25/0097* (2013.01); *A61M 25/0606* (2013.01); *A61M 25/0637* (2013.01);
(Continued)

(58) Field of Classification Search
CPC .......... A61M 25/0693; A61M 25/0097; A61M 25/0606; A61M 25/0637; A61M 39/10;
(Continued)

(56) References Cited

U.S. PATENT DOCUMENTS 4,326,519 A * 4/1982 D'Alo ............... A61M 25/0631
604/177
4,559,043 A 12/1985 Whitehouse et al.
(Continued)

FOREIGN PATENT DOCUMENTS

AU 2010201228 4/2010
BR PI0210011 B1 8/2004
(Continued)

*Primary Examiner* — Kami A Bosworth
*Assistant Examiner* — Avery Smale
(74) *Attorney, Agent, or Firm* — Kirton McConkie; Whitney Blair; Kevin Stinger

(57) ABSTRACT

An intravenous (IV) catheter system may include a catheter adapter having a proximal end and a distal end. The IV catheter system may also include a cannula extending through the catheter adapter. A proximal end of the cannula may include a notch. The IV catheter system may also include a needle hub, which may be coupled to the proximal end of the catheter adapter. The needle hub may include a flashback chamber, which may be in fluid communication with the notch when the IV catheter system is in an insertion configuration.

8 Claims, 40 Drawing Sheets

Related U.S. Application Data

(60) Provisional application No. 62/501,670, filed on May 4, 2017.

(51) Int. Cl.
  *A61M 25/06*    (2006.01)
  *A61M 39/10*    (2006.01)

(52) U.S. Cl.
  CPC ..... *A61M 39/10* (2013.01); *A61M 2005/1586* (2013.01); *A61M 2025/0098* (2013.01); *A61M 25/0612* (2013.01); *A61M 2039/1077* (2013.01)

(58) Field of Classification Search
  CPC .. A61M 2039/1077; A61M 2202/0413; A61M 2205/583; A61M 2025/0098; A61M 2005/1586; A61M 25/0612; A61M 2025/028; A61M 25/02; A61M 2205/0216
  See application file for complete search history.

(56) References Cited

U.S. PATENT DOCUMENTS

| | | | |
|---|---|---|---|
| 4,710,173 | A | 12/1987 | McFarlane |
| 4,772,267 | A | 9/1988 | Brown |
| 5,057,087 | A | 10/1991 | Harmon |
| 5,137,518 | A | 8/1992 | Mersch |
| 5,176,655 | A | 1/1993 | McCormick et al. |
| 5,269,764 | A | 12/1993 | Vetter et al. |
| 5,690,612 | A | 11/1997 | Lopez et al. |
| 5,961,497 | A | 10/1999 | Larkin |
| 6,117,108 | A | 9/2000 | Woehr et al. |
| 6,656,161 | B2 | 12/2003 | Young et al. |
| 6,719,727 | B2 | 4/2004 | Brimhall et al. |
| 7,635,352 | B2 | 12/2009 | Adams |
| 8,496,623 | B2 | 7/2013 | Burkholz |
| 9,399,120 | B2 | 7/2016 | Burkholz |
| 10,493,244 | B2 | 12/2019 | Peterson et al. |
| 10,500,376 | B2 | 12/2019 | Isaacson et al. |
| 10,507,281 | B2 | 12/2019 | Burkholz et al. |
| 2001/0018572 | A1 | 8/2001 | Kinsey et al. |
| 2002/0082546 | A1 | 6/2002 | Crank et al. |
| 2002/0177816 | A1* | 11/2002 | Brimhall ........... A61M 25/0637 604/174 |
| 2004/0122373 | A1 | 6/2004 | Botich et al. |
| 2005/0043709 | A1 | 2/2005 | Brimhall et al. |
| 2007/0010796 | A1 | 1/2007 | Moran et al. |
| 2007/0093778 | A1 | 4/2007 | Cindrich et al. |
| 2007/0225648 | A1 | 9/2007 | Winsor et al. |
| 2008/0287876 | A1 | 11/2008 | Shue et al. |
| 2009/0227953 | A1 | 9/2009 | Tan et al. |
| 2010/0204648 | A1 | 8/2010 | Stout |
| 2010/0249713 | A1 | 9/2010 | Burkholz |
| 2011/0046570 | A1 | 2/2011 | Stout et al. |
| 2013/0165868 | A1 | 6/2013 | Isaacson et al. |
| 2013/0338577 | A1 | 12/2013 | Al-Habaibeh |
| 2014/0122373 | A1 | 5/2014 | Markov et al. |
| 2015/0025466 | A1 | 1/2015 | Antonucci |
| 2015/0224296 | A1 | 8/2015 | Winsor |
| 2016/0015892 | A1 | 1/2016 | Turner et al. |
| 2016/0100860 | A1 | 4/2016 | Lenker et al. |
| 2016/0220805 | A1* | 8/2016 | Goral .................. A61B 5/1535 |
| 2016/0354580 | A1* | 12/2016 | Teoh .................. A61M 5/1626 |
| 2017/0119997 | A1 | 5/2017 | Burkholz et al. |

FOREIGN PATENT DOCUMENTS

| | | |
|---|---|---|
| BR | PI0617697 A2 | 8/2011 |
| CA | 2201055 | 10/1997 |
| CN | 101321549 A | 12/2008 |
| CN | 104540538 A | 4/2015 |
| CN | 208785540 U | 4/2019 |
| EP | 0200393 | 11/1986 |
| EP | 0989872 A1 | 4/2000 |
| EP | 1016429 A1 | 7/2000 |
| EP | 1110574 | 6/2001 |
| EP | 2022421 A1 | 2/2009 |
| EP | 2952221 A | 12/2015 |
| JP | 60-60858 | 4/1985 |
| JP | S61-253073 A | 11/1986 |
| JP | 2005523782 A | 8/2005 |
| JP | 2008097955 A | 4/2008 |
| JP | 2012521797 | 9/2012 |
| JP | 5060858 B2 | 10/2012 |
| JP | 2014514016 | 6/2014 |
| JP | 2013502240 A | 8/2014 |
| JP | 60-60858 B2 | 1/2017 |
| JP | 2018532012 A | 11/2018 |
| WO | 2002096494 A2 | 12/2002 |
| WO | 2002096495 A1 | 12/2002 |
| WO | 2011146769 A2 | 11/2011 |
| WO | 2016152169 A1 | 9/2016 |
| WO | 2018026006 A1 | 2/2018 |
| WO | 2018204636 A3 | 11/2018 |

* cited by examiner

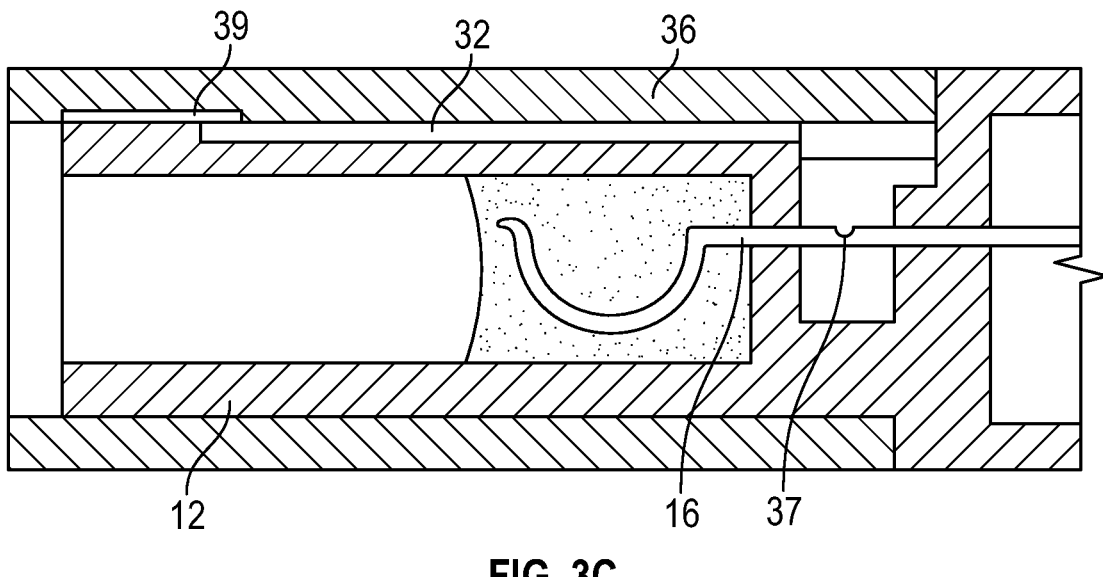
FIG. 3C
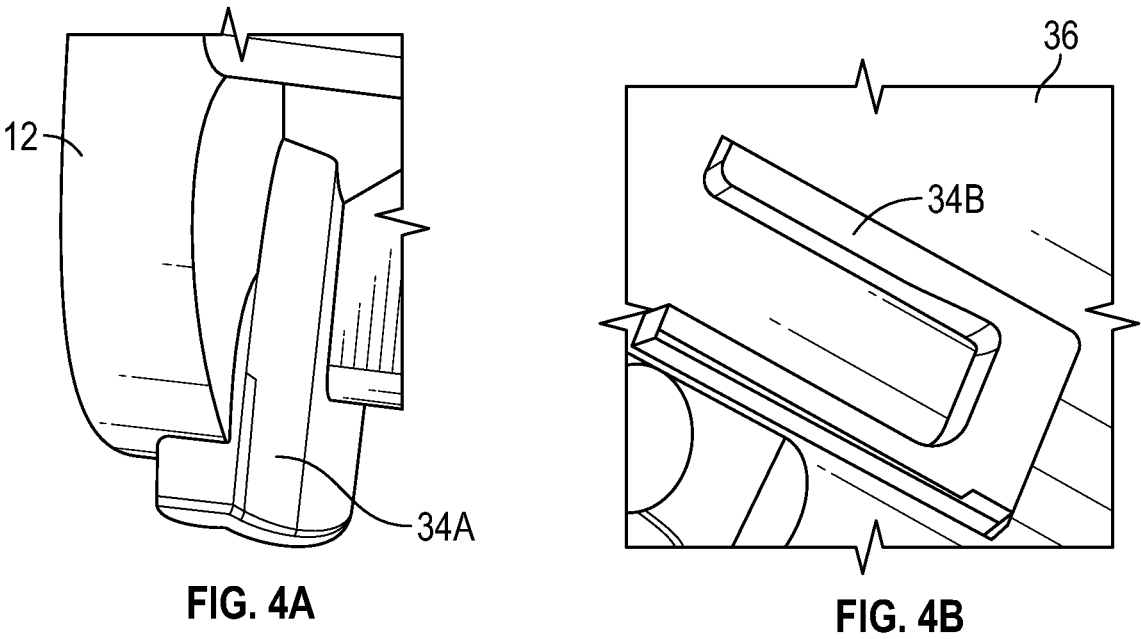
FIG. 4A
FIG. 4B

18

85
84

86

88

18

18

INTRAVENOUS CATHETER SYSTEMS AND METHODS

RELATED APPLICATIONS

This application is a divisional of U.S. patent application Ser. No. 15/969,584, filed May 2, 2018, and entitled INTRAVENOUS CATHETER SYSTEMS AND METHODS, which claims priority to U.S. Provisional Application Ser. No. 62/501,670, filed May 4, 2017, and entitled INTRAVENOUS CATHETER SYSTEMS AND METHODS, which is incorporated herein in its entirety.

BACKGROUND

Infusion therapy, a common healthcare procedure, may be facilitated by a vascular access device. Hospitalized, home care, and other patients receive fluids, pharmaceuticals, and blood products via a vascular access device inserted into the vascular system. Blood withdrawal is another common healthcare procedure that may be facilitated by a vascular access device.

A vascular access device may access a peripheral or central vasculature of a patient. A vascular access device may be indwelling for short term (days), moderate term (weeks), or long term (months to years). In some instances, the vascular access device may cause irritation to the skin of the patient when left in place for an extended period of time. A vascular access device may be used for continuous infusion therapy or for intermittent therapy.

A common type vascular access device is an over-the-needle peripheral intravenous catheter ("PIVC"). As its name implies, the "over-the-needle" PIVC may be mounted over an introducer needle having a sharp distal tip. The sharp distal tip may be used to pierce the skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient.

In order to verify proper placement of the introducer needle and/or the PIVC in the vasculature, a user generally confirms that there is flashback of blood, which may be visible to the user. In some instances, the introducer needle may include a notch disposed towards a distal end of the introducer needle, and in response to the distal tip of the introducer needle being positioned within the vasculature, blood may flow proximally through a needle lumen, exit the needle lumen through the notch, and then travel proximally between an outer surface of the introducer needle and an inner surface of the PIVC.

Accordingly, where the PIVC is at least partially transparent, the user may visualize a small amount of blood "flashback" and thereby confirm placement of the PIVC within the vasculature. Presence of a vasculature entrance indicator, such as flashback, may facilitate successful placement of PIVCs. Once placement of the introducer needle within the vasculature has been confirmed, the user may temporarily occlude flow in the vasculature and withdraw the introducer needle, leaving the PIVC in place for future blood withdrawal and/or fluid infusion.

The user may also attach a device to the PIVC for fluid infusion and/or blood withdrawal. This process has been somewhat difficult in practice since many catheter placement sites simply do not allow easy occlusion of the vein. Additionally, even when such occlusion is achieved, it may be imperfect, resulting in blood leaking from a catheter assembly housing the PIVC and endangering medical personnel. Catheter assemblies have thus been provided in the art that provide a variety of seals or "septa" for preventing outflow of fluid during and following removal of the introducer needle from the blood vessel.

A septum may be secured within the catheter assembly via friction and/or adhesive between the septum and a wall of the catheter assembly. However, in some instances, septum dislodgement may occur in response to pressurization of the catheter assembly, which may result from venous pressure, fluid injection under high or low pressure, flush of the catheter assembly, blood collection, etc. Septum dislodgement presents a risk of exposure by medical personnel to blood or other fluids. Thus, challenges to infusion and/or blood withdrawal using a vascular access device still remain.

The subject matter claimed herein is not limited to embodiments that solve any disadvantages or that operate only in environments such as those described above. Rather, this background is only provided to illustrate one example technology area where some implementations described herein may be practiced.

SUMMARY

In some embodiments, an IV catheter system may include a catheter adapter having a proximal end and a distal end. In some embodiments, the IV catheter system may also include a cannula extending through the catheter adapter. In some embodiments, a proximal end of the cannula may include a notch. In some embodiments, the IV catheter system may also include a needle hub, which may be coupled to the proximal end of the catheter adapter. In some embodiments, the needle hub may include an elongated visualization channel, which may be in fluid communication with the notch when the IV catheter system is in an insertion configuration. In some embodiments, the visualization channel and other elements described later in further detail may facilitate visualization of blood flashback by a user of the IV catheter system.

In some embodiments, a portion of the catheter adapter may be constructed of a first material and another portion of the catheter adapter may be constructed of a second material. In some embodiments, the second material may have a lower durometer than the first material and may be more soft or flexible. In some embodiments, the second material may improve contact of the IV catheter system with skin of the patient and provide other advantages, which will be explained later in further detail.

In some embodiments, the catheter adapter may include one or more stabilization features, such as, for example, ribs or another type of protrusion, which may reduce a distance between a septum canister housing a septum of the IV catheter system. In some embodiments, the stabilization ribs may provide increased securement of the septum canister and septum within the catheter adapter, as will be explained later in further detail.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 3C is a cross-sectional view of another example catheter system, illustrating an example secondary flashback chamber, according to some embodiments;

FIG. 4A is an upper perspective view of an example retention feature of an example needle hub, according to some embodiments;

FIG. 4B is an upper perspective view of an example corresponding retention feature of an example sleeve, according to some embodiments;

DESCRIPTION OF EMBODIMENTS

FIGS. 1A-19C may describe various catheter systems 10, according to some embodiments. In some embodiments, the catheter systems 10 may include IV catheter systems or PIVC systems. In some embodiments, a particular catheter system 10 may include one or more components or features from one or more of FIGS. 1A-19C.

Figure 1A:
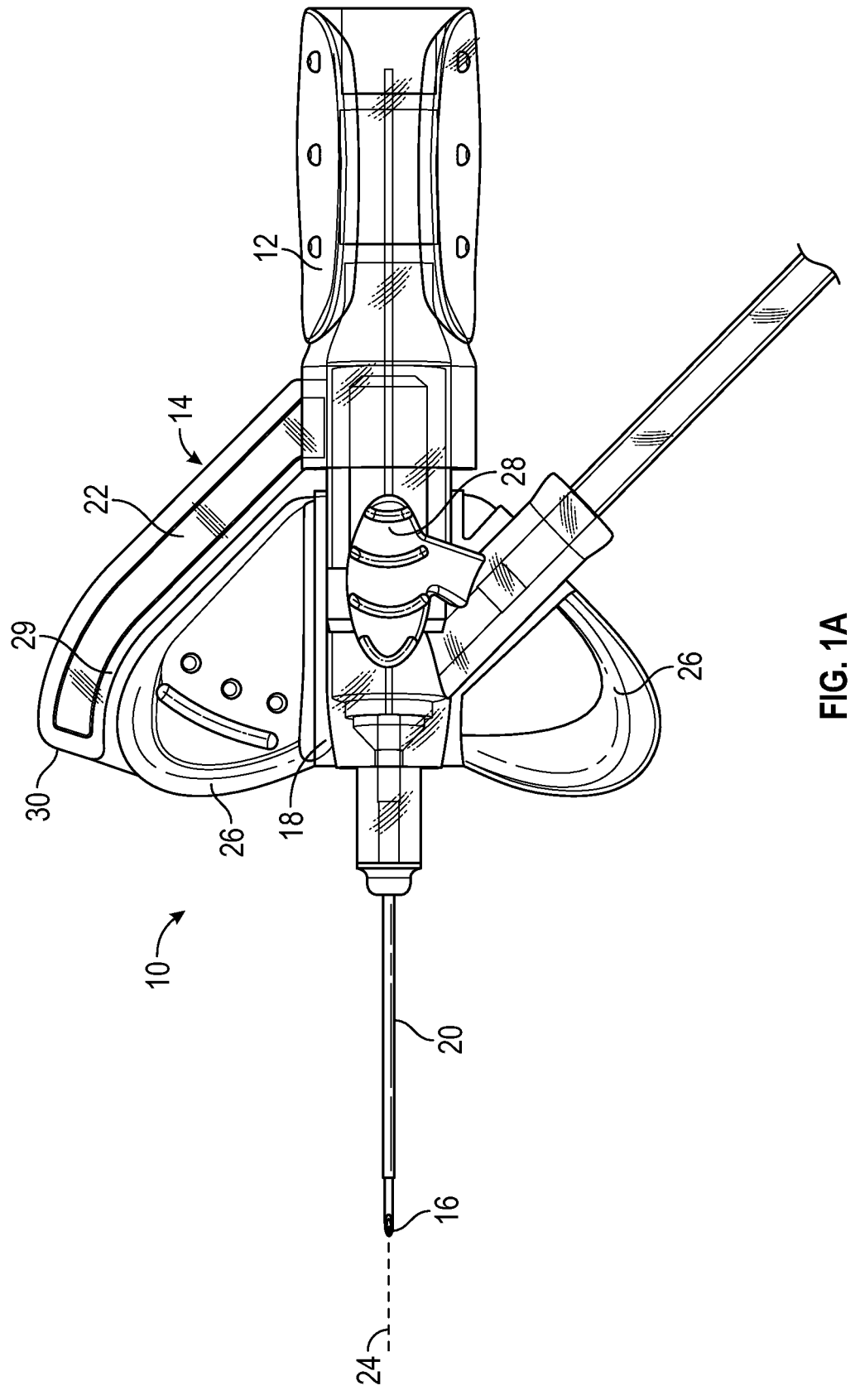
FIG. 1A is a top view of an example catheter system, according to some embodiments.
Figure 1B:
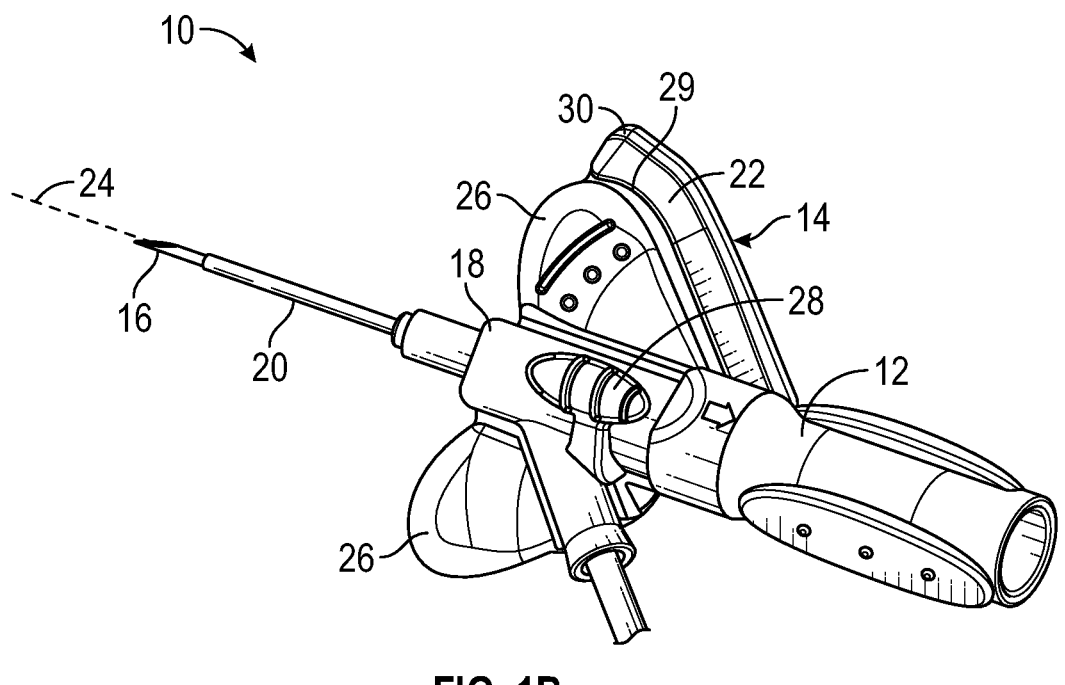
FIG. 1B is an upper perspective view of the catheter system of FIG. 1A, according to some embodiments.
Figure 1C:
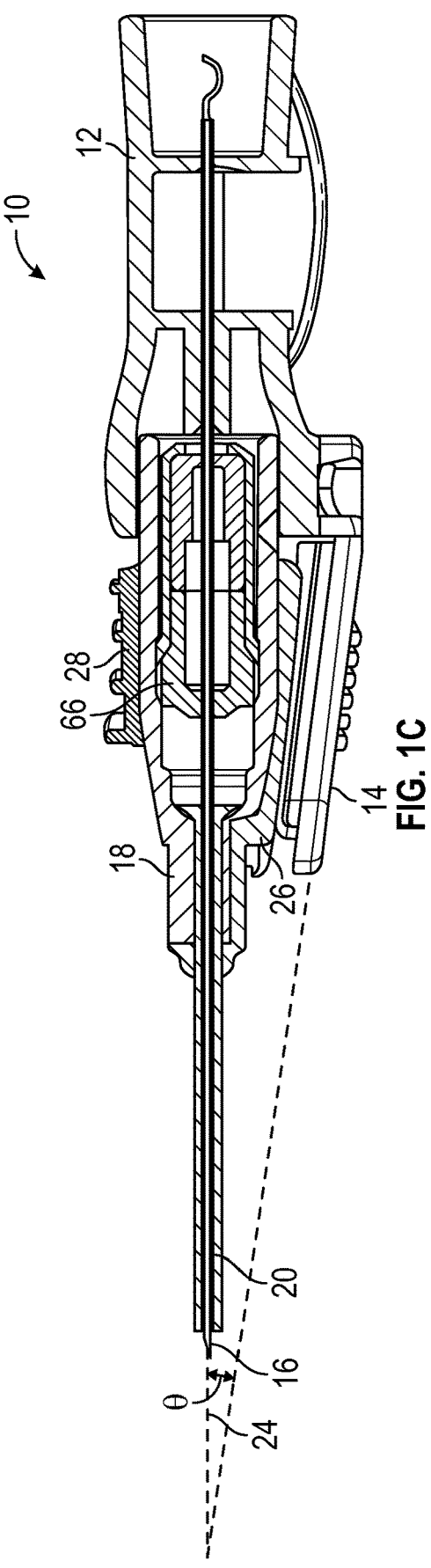
FIG. 1C is a cross-sectional view of the catheter system of FIG. 1A, according to some embodiments.

Referring now to FIGS. 1A-1C, in some embodiments, a catheter system 10 may include a needle hub 12 and a grip 14. In some embodiments, the needle hub 12 and the grip 14 may be a single component and integrally formed. In some embodiments, the needle hub 12 and the grip 14 may be monolithically formed as a single unit. In some embodiments, the grip 14 may extend outwardly from the needle hub 12. In some embodiments, the grip 14 may include a paddle grip.

In some embodiments, a cannula 16 of the catheter system 10 may include a notch (not illustrated in FIGS. 1A-1C) towards a distal end of the cannula 16, which may provide primary flashback indicating that a catheter 20 of the catheter system 10 has been properly placed within a vein of the patient. In some embodiments, the cannula 16 may include an introducer needle having a sharp distal tip. In some embodiments, the proximal end of the cannula 16 may be secured to and/or within the needle hub 12.

In some embodiments, the needle hub 12 and/or the grip 14 may be transparent. In some embodiments, the needle hub 12 and/or the grip 14 may be non-transparent. In some embodiments, a catheter adapter 18 of the catheter system 10 may be transparent to allow the user to observe primary flashback. In some embodiments, it may be preferred that the needle hub 12 and/or the grip 14 are white, which may provide a color contrast with blood to facilitate visualization of primary flashback by the user. In some embodiments, the grip may include a wing 22, which may extend outwardly from the needle hub 12.

As illustrated in FIG. 1C, in some embodiments, a longitudinal or center axis 24 of a catheter 20 extending distally from the catheter adapter 18 may be angled with respect to a bottom surface of the grip 14 and/or a bottom surface of a securement platform 26, which may minimize a transition between a distal nose of the catheter adapter 18 and the vein, once the catheter system 10 is inserted within the vein. In some embodiments, the center axis 24 of the catheter 20 may be angled with respect to the bottom surface of the grip 14 and/or the bottom surface of the securement platform 26 at an angle θ between approximately 0 and 15 degrees. In some embodiments, the angle θ may be approximately 6 degrees.

In some embodiments, a proximal end of a cannula 16 of the catheter system 10 may be accessible during assembly of the catheter system 10, which may allow for lie distance adjustment. In some embodiments, the proximal end of the cannula 10 may be crimped and/or glued in a well near a rear of the needle hub 12, which may provide additional mechanical retention of the cannula 16.

In some embodiments, the catheter adapter 18 may include one or more push tab features 28. In some embodiments, the push tab features 28 may be connected to the securement platform 26 on one or more sides of the catheter adapter 18, which may improve mold filling. In some embodiments, a distal portion of the wing 22 which may be disposed below the securement platform 26 of the catheter system 10, may include an edge 30 that may be rounded and/or tapered to facilitate taping of a dressing to the skin of the patient and/or reduce trapped air. In some embodiments, the edge 30 may include a transitional profile that guides a thumb of a user to facilitate gripping. In some embodiments, the distal portion of the wing 22 may include the edge 30, as illustrated, for example, in FIG. 1A. In some embodiments, the wing 22 may include a ridge 29, which may abut the securement platform 26.

Figure 1D:
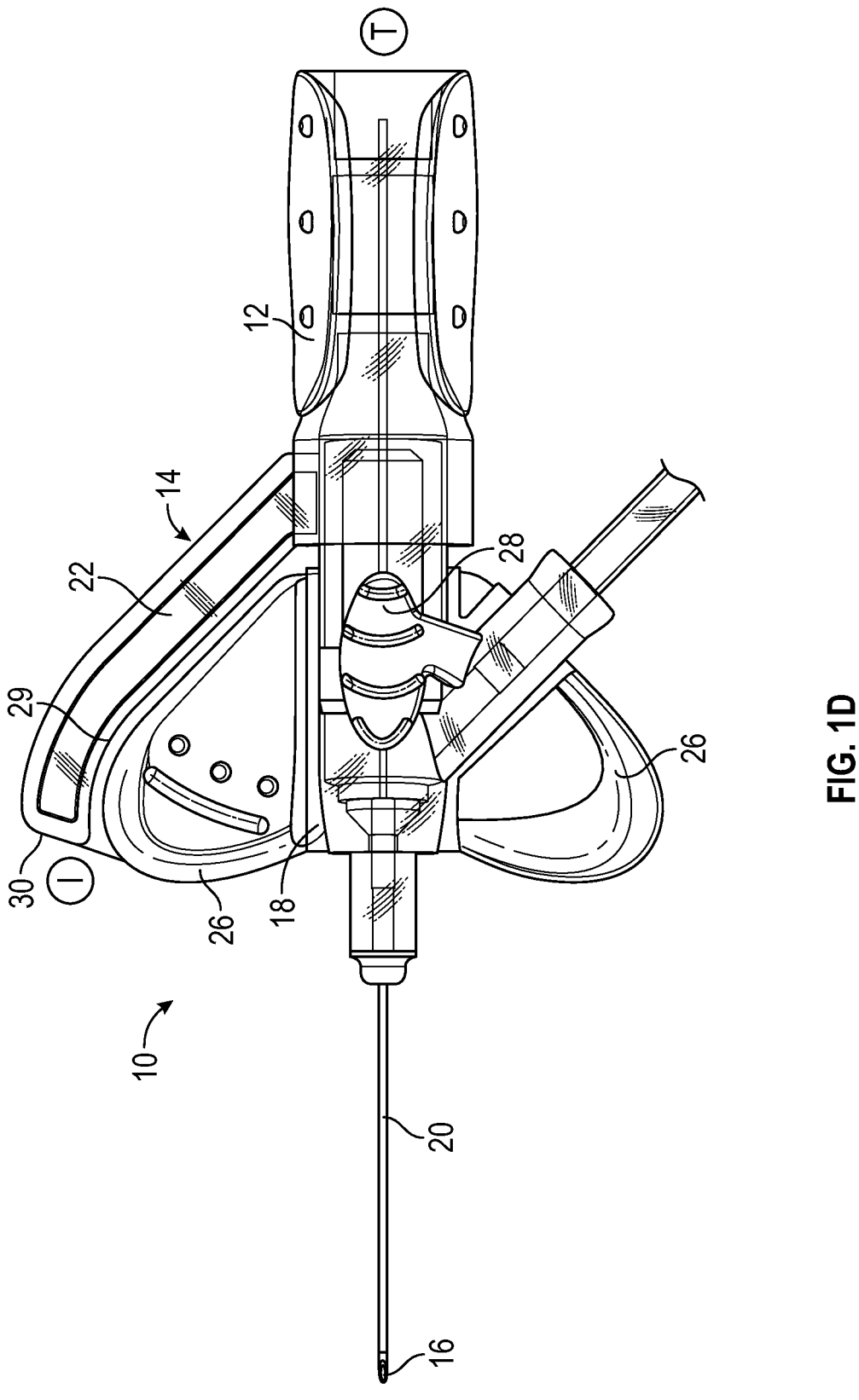
FIG. 1D is a top view of the catheter system of FIG. 1A, held in a first grip, according to some embodiments.
Figure 1E:
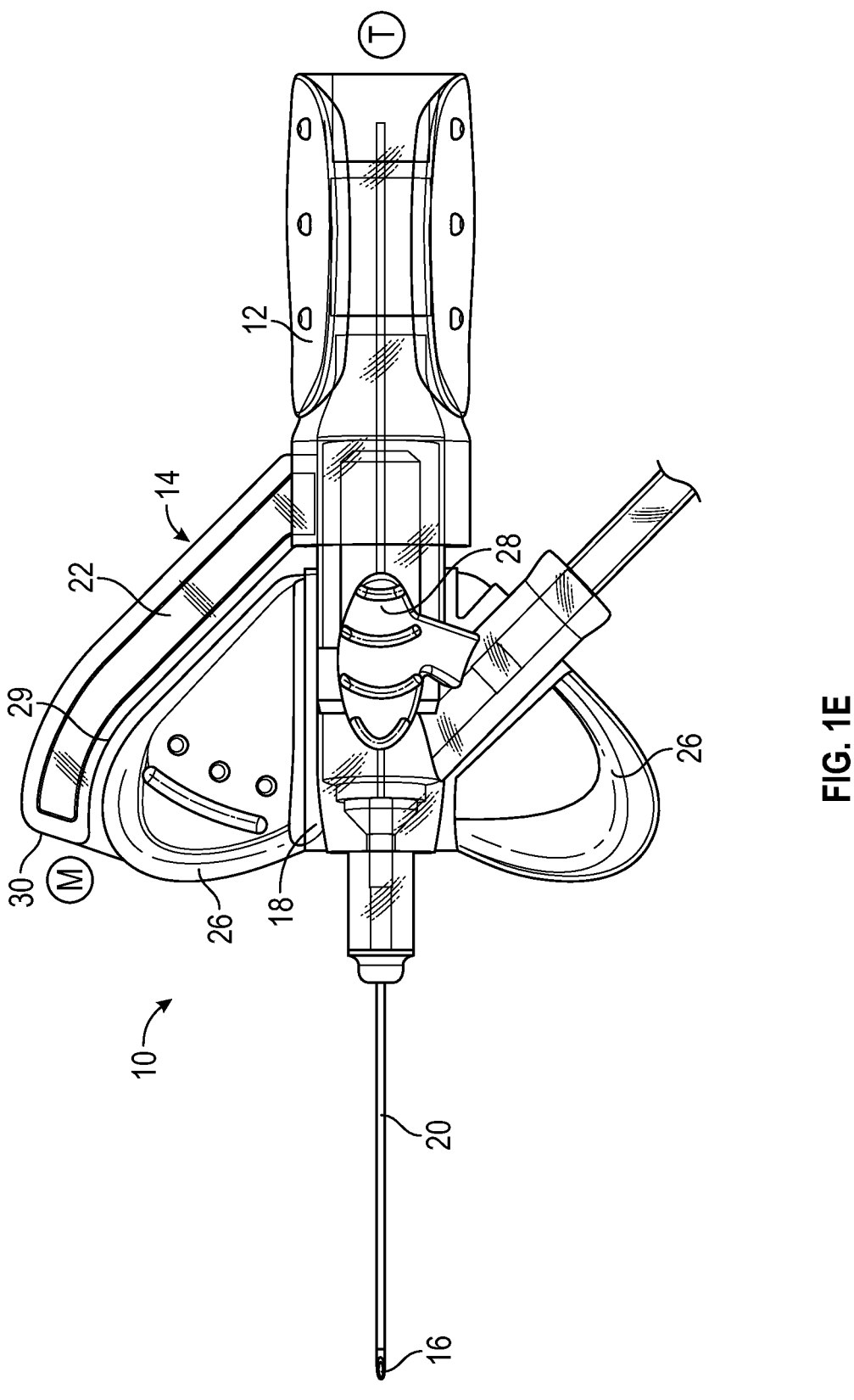
FIG. 1E is a top view of the catheter system of FIG. 1A, held in a second grip, according to some embodiments.

Referring now to FIGS. 1D-1E, in some embodiments, I, T, and M refer to the index finger, thumb, and middle finger of the user, respectively, and indicate approximate positions of the I, T, and M, respectively. For example, the thumb may be disposed proximate the proximal end of the needle hub 12. FIGS. 1D-1E illustrate modified ported grip techniques. In some embodiments, the edge 30, which may have an angled or tapered upper surface, may facilitate use of these modified ported grip techniques by the user.

Figure 2:
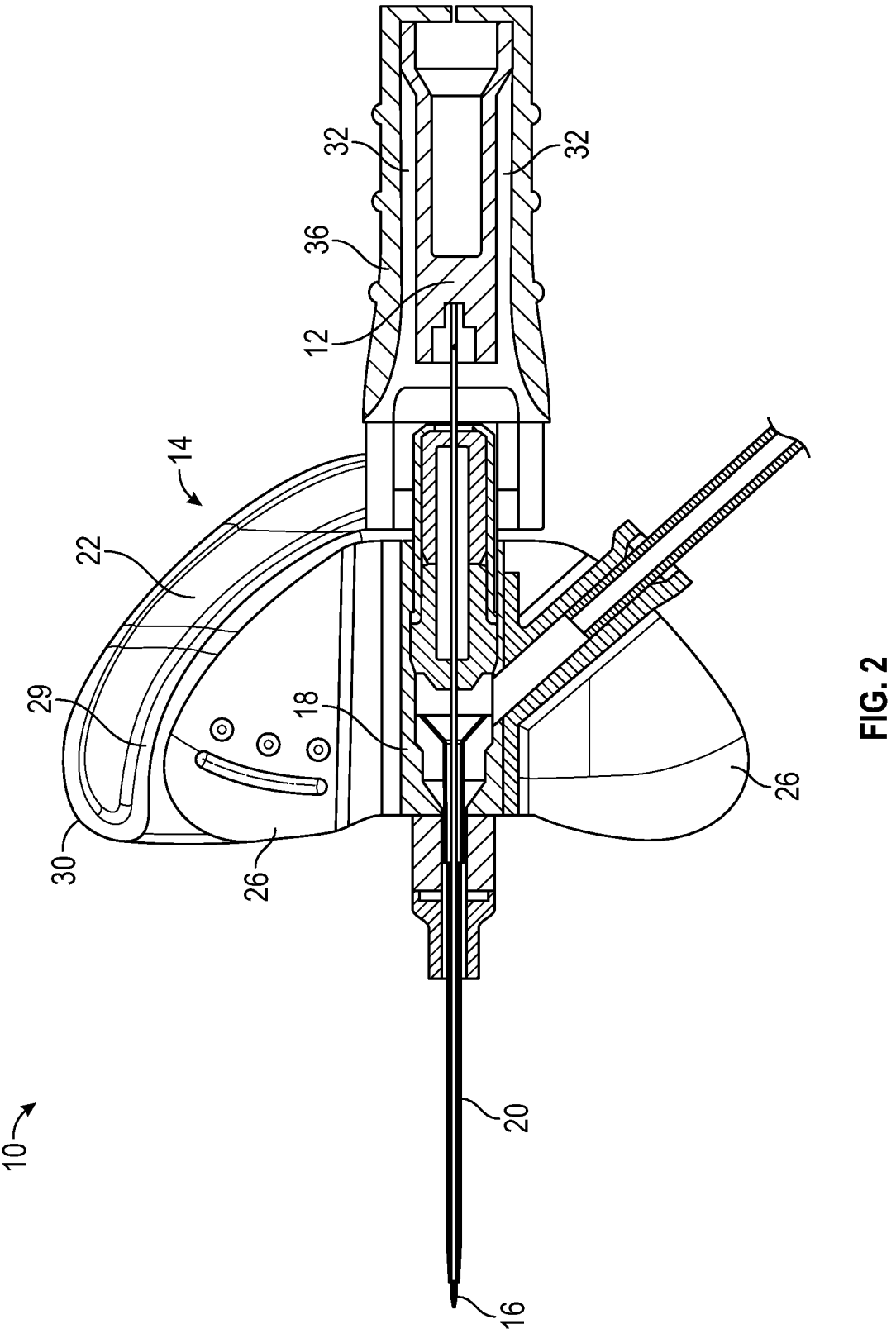
FIG. 2 is a cross-sectional view of another example catheter system, illustrating a secondary flashback chamber, according to some embodiments.

Referring now to FIG. 2, the catheter system 10 is illustrated according to some embodiments. In some embodiments, the grip 14 and the needle hub 12 may be a single component and integrally formed. In some embodiments, the grip 14 and the needle hub 12 may be monolithically formed as a single unit. In some embodiments, a sleeve 36 of the needle hub 12 may be removable from the grip 14 and/or the needle hub 12. In some embodiments, one or more of the sleeve 36, the needle hub 12, and the grip 14 may be a single component and integrally formed. In some embodiments, one or more of the sleeve 36, the needle hub 12, and the grip 14 may be monolithically formed as a single unit.

In some embodiments, a flashback chamber 32 may be provided within or proximate the needle hub 12 of the catheter system 10. In some embodiments, the flashback chamber 32 may be disposed between the sleeve 36 and the needle hub 12. In some embodiments, the cannula 16 may include a notch disposed towards a proximal end of the cannula 16, which may allow blood to flow into the flashback chamber 32. In some embodiments, the flashback chamber 32 may be a secondary flashback chamber in fluid communication with the notch disposed towards the proximal end of the cannula 16 and/or an opening of the proximal end of the cannula 16.

In some embodiments, the needle hub 12 may include or correspond to a vent plug. In some embodiments, the needle hub 12 and/or the sleeve 36 may include a filter or vent permeable to air but not blood. In some embodiments, the plug 27 may be placed into a proximal end of the sleeve 36 to form an interface with the flashback chamber 32. In some embodiments, the flashback chamber 32 may include a visualization channel, as will be explained later in further detail. In some embodiments, the plug 27 may be white or another non-transparent color, which may enhance contrast of blood in the visualization channel for better visibility. In some embodiments, the sleeve 36 may be transparent.

Figure 3A:
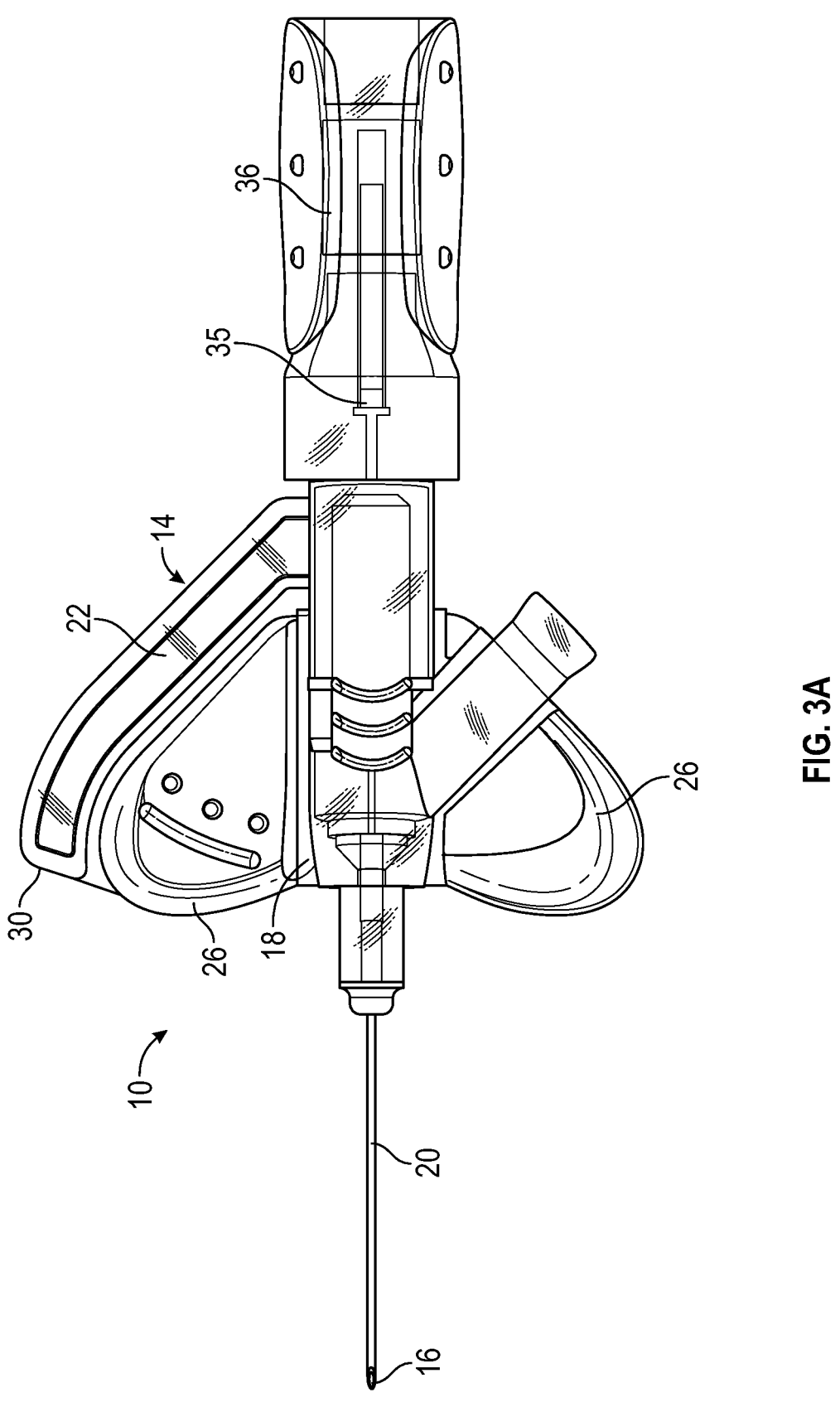
FIG. 3A is an upper perspective view of another example catheter system, illustrating an example sleeve, according to some embodiments.
Figure 3B:
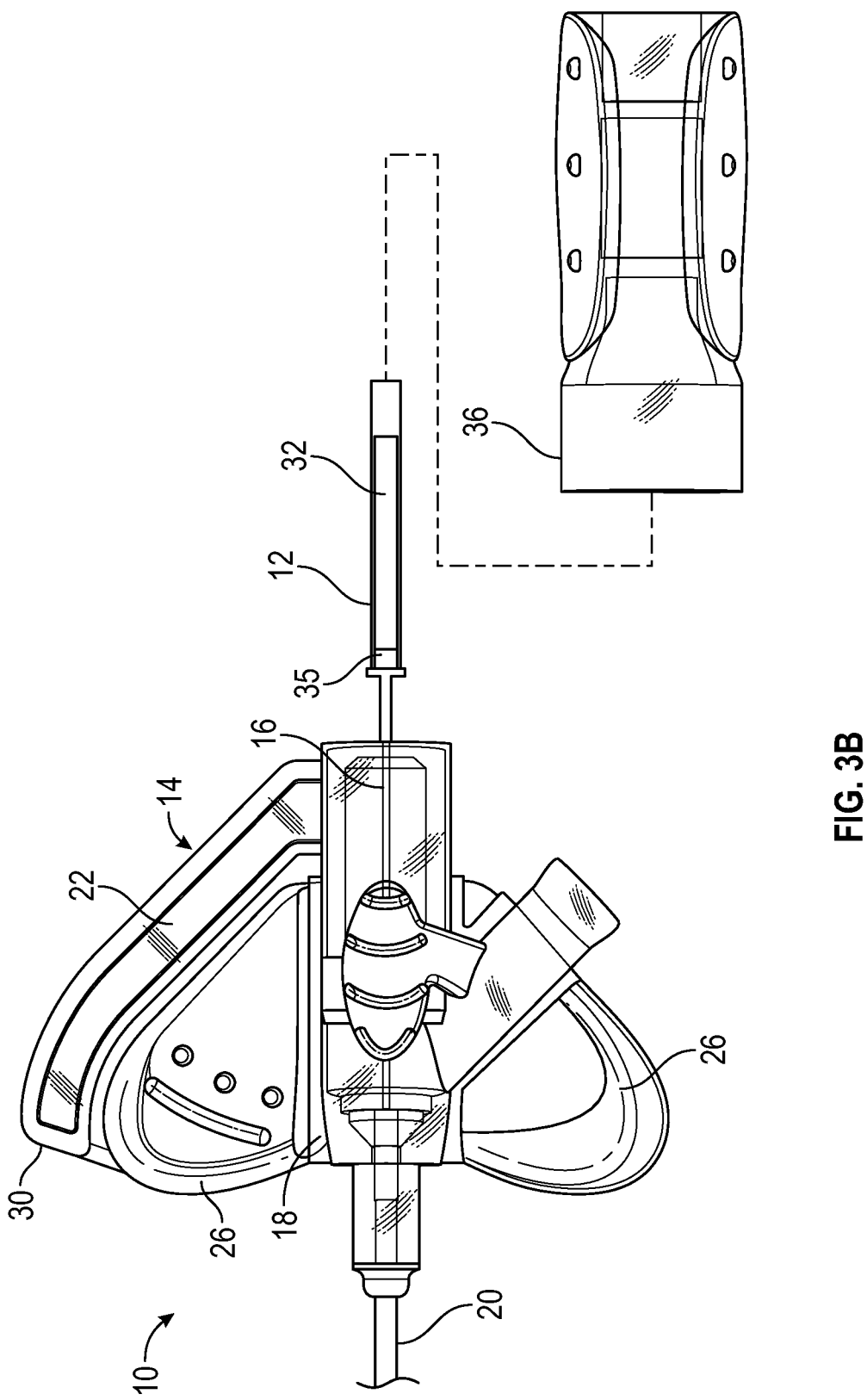
FIG. 3B is an upper perspective view of the catheter system of FIG. 3A, illustrating the sleeve removed, according to some embodiments.

Referring now to FIG. 3A-3C, in some embodiments, the catheter system 10 may include the sleeve 36 that may include an additional gripping surface 33. In some embodiments, the sleeve 36 may be coupled to the needle hub 12 and provide a fluid-tight seal around the flash chamber 32. In some embodiments, the sleeve 36 may be transparent or clear, which may allow the user to view blood 35 within the flashback chamber 32, which may be disposed between the sleeve 36 and the needle hub 12. In some embodiments, the needle hub 12 and/or the grip 14 may be white, which may be a most familiar color for catheter components in the market. In some embodiments, the needle hub 12 may include the visualization channel, and the sleeve 36 may tightly cover the visualization channel to provide a fluid-tight seal and prevent blood received from the cannula 16 into the visualization channel from exiting the visualization channel.

In some embodiments, the sleeve 36 may be universal for all catheter gauge sizes. In some embodiments, all catheter gauge size dependent features may be disposed in the needle hub 12 and/or the grip 14, while the sleeve 36 may remain standard across all catheter gauge sizes. FIG. 3C illustrates a possible configuration of the catheter system 10 with the sleeve 36, according to some embodiments.

As illustrated in FIG. 3C, in some embodiments, a proximal end of the cannula 16 may be secured in the needle hub 12 via an adhesive or another suitable mechanism. In some embodiments, the cannula 16 may include a notch 37 towards the proximal end of the cannula 16, and the notch 37 may be in fluid communication with the flash chamber 32. In some embodiments, the flash chamber 32 may be disposed between the sleeve 36 and the needle hub 12. In some embodiments, in response to insertion of the cannula 16 into the vein of the patient, the blood may flow into the cannula 16 and out the notch 37 into the flash chamber 32. In some embodiments, a venting channel 39 may be disposed proximate the flash chamber 32 and may be permeable to air but not blood.

Figure 4C:
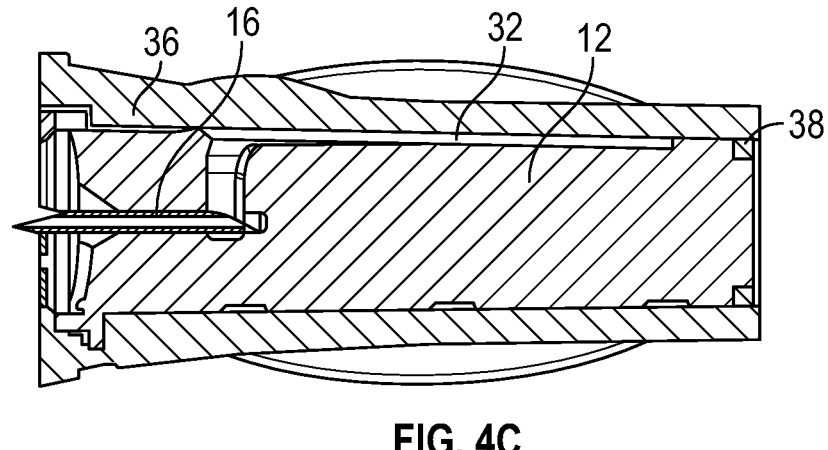
FIG. 4C is a cross-sectional view of an example potting ring, according to some embodiments.

Referring now to FIGS. 4A-4C, in some embodiments, the needle hub 12 may be secured to the sleeve 36 to prevent separation of the needle hub 12 and the sleeve 36 when the sleeve 36 is gripped by the user. In some embodiments, one or more mechanisms may be used to couple the needle hub 12 and the sleeve 36 together. For example, the needle hub 12 and the sleeve 36 may be coupled together via an interference fit. As another example, a mechanical lock and/or a snap feature may be used to couple the needle hub 12 and the sleeve 36 together. As a further example, an adhesive may be disposed in a cavity at an interface of the needle hub 12 and the sleeve 36 to couple the needle hub 12 and the sleeve 36 together. FIGS. 4A and 4B illustrate example retention features of the needle hub 12 and the sleeve 36, respectively. In further detail, in some embodiments, a retention feature 34a of the needle hub 12 may be configured to engage in a snap fit with a corresponding retention feature 34b of the sleeve 36. In some embodiments, the retention feature 34a may be disposed on an outer surface of the needle hub, and the corresponding retention feature 34b may be disposed on an inner surface of the sleeve 36. FIG. 4C illustrates an example potting ring 38, which may include an adhesive to glue the needle hub 12 and the sleeve 36 together.

Figure 5A:
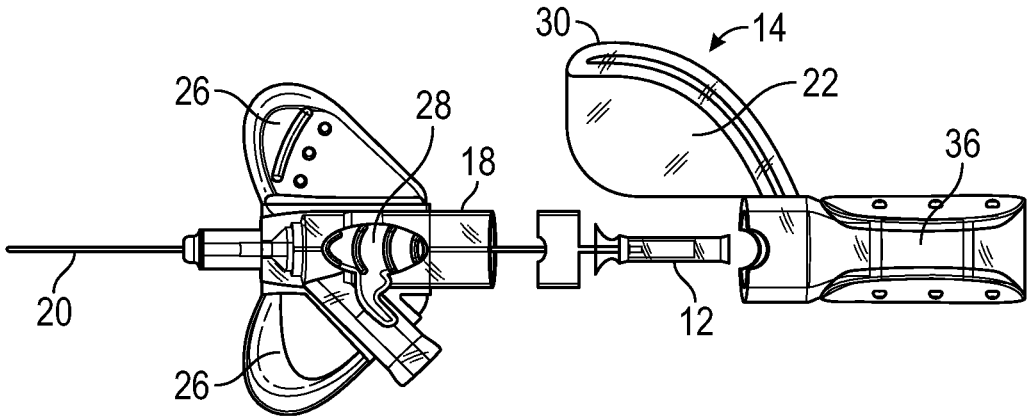
FIG. 5A is a top view illustrating an example needle hub partially withdrawn from an example catheter adapter and an example sleeve removed from the needle hub, according to some embodiments.
Figure 5B:
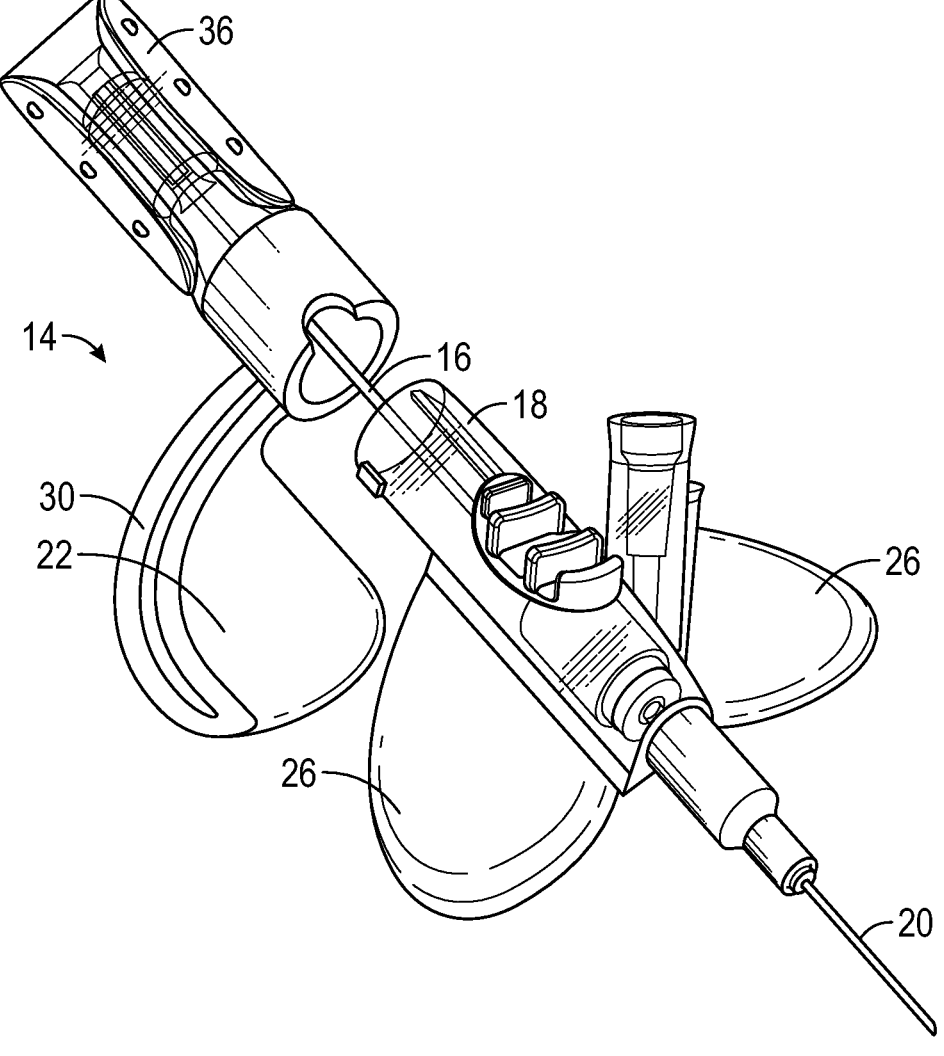
FIG. 5B is a upper perspective view illustrating the needle hub of FIG. 5A partially withdrawn from the catheter adapter and the sleeve coupled to the needle hub, according to some embodiments.

Referring now to FIGS. 5A-5B, in some embodiments, the sleeve 36 and the grip 14 may be a single component and integrally formed. In some embodiments, the sleeve 36 may be generally cylindrical. In some embodiments, the sleeve 36 may surround and/or encapsulate the needle hub 12. In some embodiments, the needle hub 12 may be coupled to the sleeve 36 and the grip 14 via the one or more mechanisms discussed with respect to FIG. 4. In some embodiments, a portion of the needle hub 12 may be coupled directly to the proximal end of the catheter adapter 18. In some embodiments, coupling of the sleeve 36 to the proximal end of the catheter adapter 18 may include an interference fit or another type of coupling.

Figure 6A:
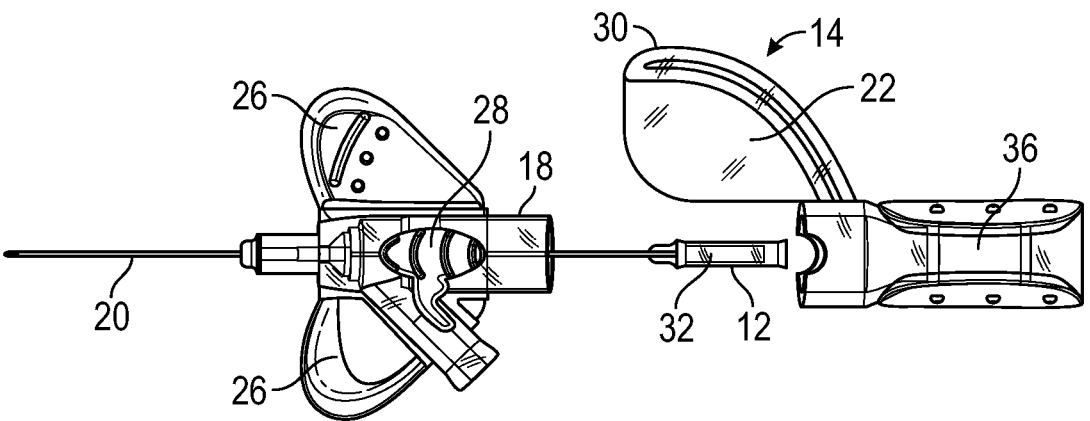
FIG. 6A is a top view illustrating an example needle hub partially withdrawn from an example catheter adapter and an example sleeve removed from the catheter adapter, according to some embodiments.
Figure 6B:
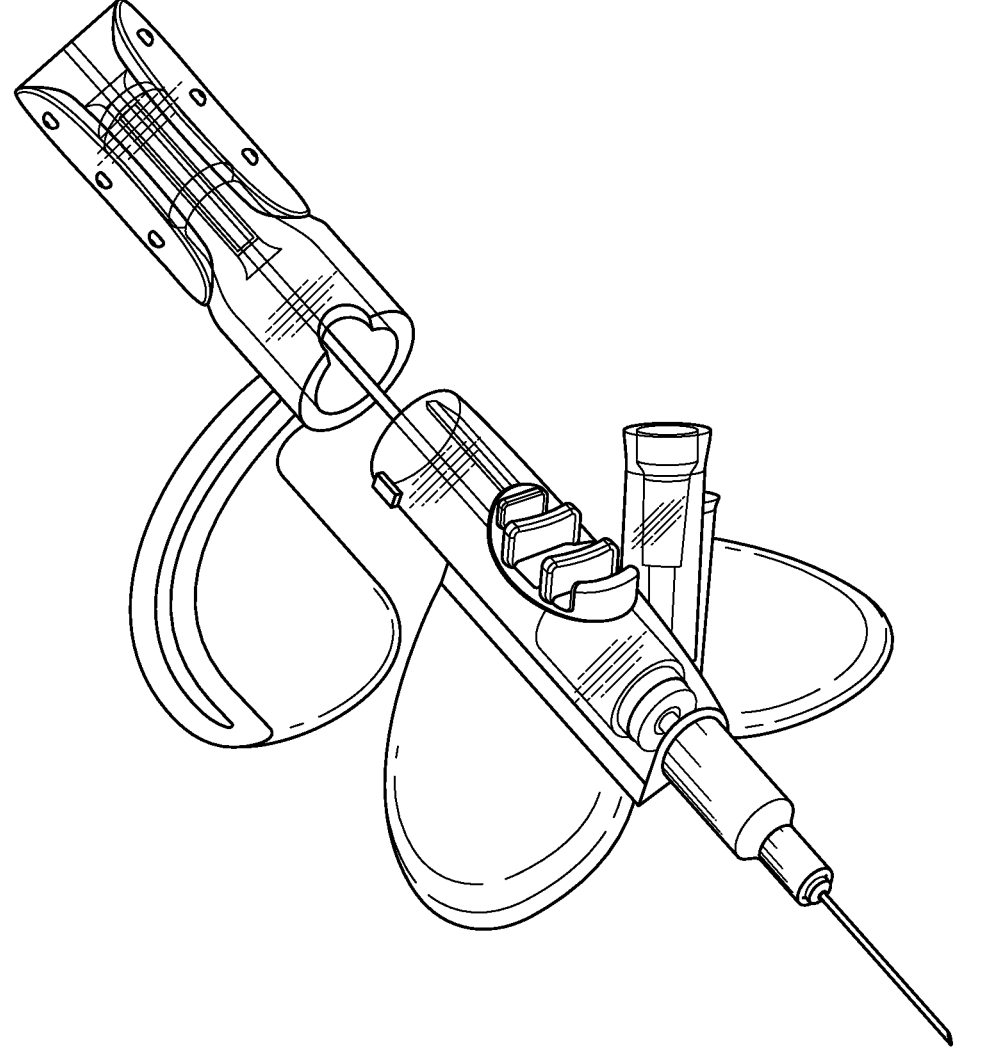
FIG. 6B is a upper perspective view illustrating the needle hub of FIG. 6A partially withdrawn from the catheter adapter and the sleeve coupled to the needle hub, according to some embodiments.

Referring now to FIGS. 6A-6B, in some embodiments, the needle hub 12 may be white. In some embodiments, the grip 14 and/or sleeve 36 may be transparent or clear. In some embodiments, the sleeve 36 may be coupled directly to the proximal end of the catheter adapter 18. In some embodiments, coupling of the sleeve 36 to the proximal end of the catheter adapter 18 may include an interference fit or another type of coupling.

In some embodiments, the catheter system 10 may enhance vein confirmation in vascular access systems featuring blood flashback. In some embodiments, the catheter system 10 may provide improved visualization timing, optical amplification, continuous motion optimization, and fluid management. In some embodiments, the catheter system 10 may provide a reduction in time for blood to appear in the flashback chamber 32, accommodate pre-priming that may otherwise flood another flashback chamber, and meter a flowrate in the visualization channel.

In some embodiments, the catheter system 10 may provide fluid confinement to guide incoming flow through the flash chamber 32, which may feature a high surface-to-volume ratio. In some embodiments, the catheter system 10 may provide an overflow pattern that compensates for various excess fluid conditions. In some embodiments, the catheter system may provide means of an unobstructed, sharp-contrast, real-time visualization of blood flashback throughout a duration of vein access. In some embodiments, the catheter system 10 may provide immediate signaling and amplification upon low-abundance blood presence.

Figure 7A:
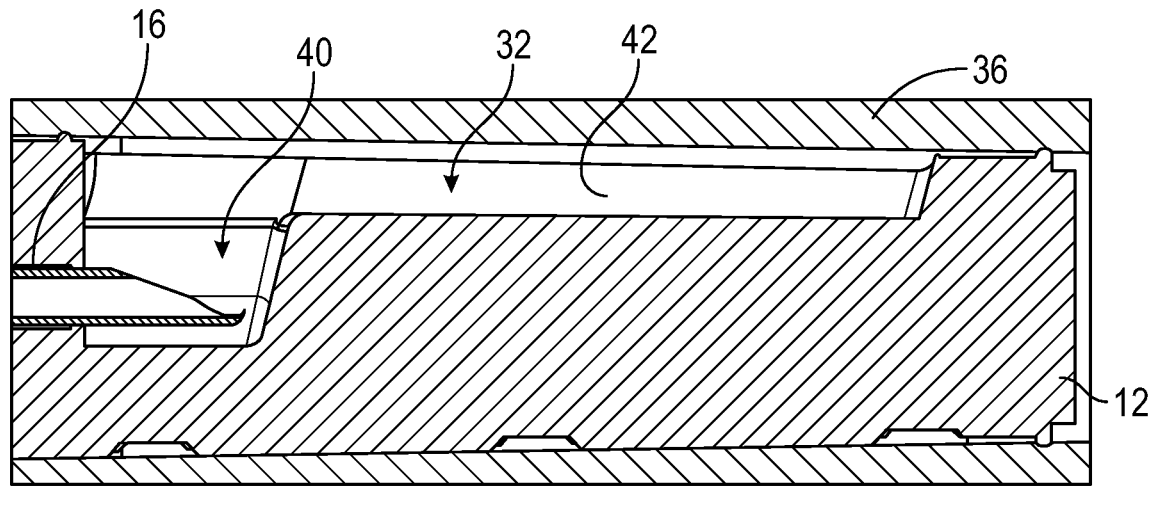
FIG. 7A is a cross-sectional view of an example needle hub and visualization channel, according to some embodiments.
Figure 7B:
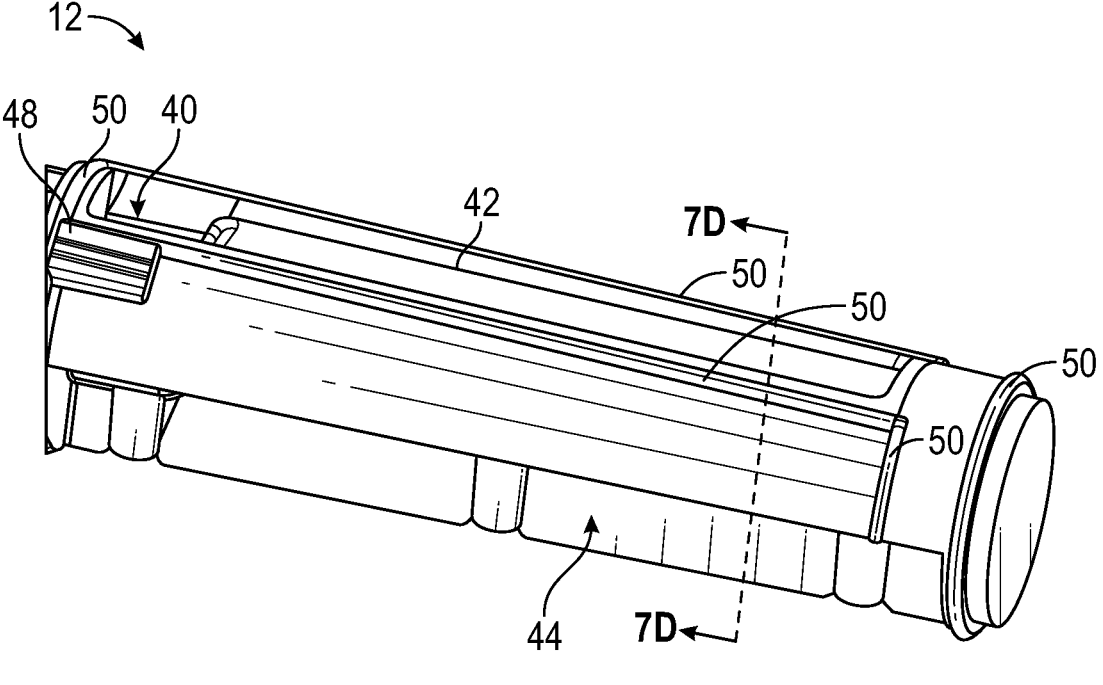
FIG. 7B is an upper perspective view of the needle hub of FIG. 7A, illustrating an example reservoir, according to some embodiments.

Referring now to FIGS. 7A-7B, in some embodiments, the flashback chamber 32 may include a pocket 40, which may house the proximal end of the cannula 16. In some embodiments, the pocket 40 may be proximate and/or in fluid communication with the visualization channel 42. In some embodiments, the visualization channel 42 may be disposed at an outer and/or upper portion of the needle hub 12 such that the user may observe the secondary flashback without obstruction. In some embodiments, secondary flashback may refer to flashback proximate the needle hub 12, while primary flashback may refer to flashback proximate the catheter 20 and/or the catheter adapter 18. In some embodiments, the pocket 40 may include an inverse cone shape. In some embodiments, a top of the pocket 40 is widened for better visualization of a blood droplet that comes out of the proximal end of the cannula 16 and/or the notch disposed towards the proximal end of the cannula 16.

In some embodiments, walls of the pocket 40 may include an outward draft that may transduce a portion of the pocket-filling motion to an in-plane liquid movement noticeable by the user. In some embodiments, a volume of the pocket 40 may be reduced for small gauges and/or a cannula-hosting hole may be piloted into the pocket 40, as illustrated, for example, in FIG. 7A, which may shorten a time between blood coming out of the notch and/or proximal end of the cannula 16 and starting to flow through the flashback chamber 32.

In some embodiments, the visualization channel 42 may include a high surface-to-volume aspect ratio, which may create an enhanced visualization signal with a small volume of blood. The aspect ratio of the visualization channel 42 may translate a volumetric flow rate to a steady meniscus velocity that can be easily captured by human eyes. In some embodiments, the longitudinal continuous motion of blood flowing through the visualization channel 42 may provide a clear thermometer-like signal of vein access. In some embodiments, the visualization channel 42 may include a length that may dictate duration of the continuous motion in accordance with a typical catheter insertion process. As such, in some embodiments, extended vein confirmation throughout insertion may be provided.

As illustrated in FIG. 7B, in some embodiments, the flashback chamber 32 may include a cavity or reservoir 44.

In some embodiments, the reservoir 44 may be disposed underneath the visualization channel 42 when the needle hub 12 is assembled with the sleeve 36. In some embodiments, the reservoir 44 may be molded in the needle hub 12 and/or connected to the visualization channel 42 via a drain channel 46 disposed at a proximal end of the visualization channel 42. In some embodiments, a volume of the reservoir 44 may be greater than or equal to approximately 20 microliters in order to contain excess fluid prior to blood flowing through the visualization channel 42.

In some embodiments, the catheter system 10 may include a vent 48, which may be disposed on the needle hub 12. In some embodiments, the vent 48 may be formed by one or more micro-grooves on the needle hub 12. In some embodiments, the vent 48 may be located at an end of an entire fluid path through the flashback chamber 32. For example, the reservoir 44 may be disposed proximate a front flange of the needle hub 12 and/or above the reservoir 44. In some embodiments, the vent 48 may throttle movement of fluid during pre-priming (in which saline may be infused inside the catheter system to purge out air) and flashback (in which blood may be driven into the flashback chamber) to reduce excess saline volume without significant compromise on time to visualize blood in the visualization channel 42 for large gauges. In some embodiments, the vent 48 may serve as a barrier to prevent fluid from leaking out of the catheter system 10.

In some embodiments, the catheter system 10 may include one or more ribs 50, which may be disposed on the needle hub 12. In some embodiments, the ribs 50 may be molded with the visualization channel 42. In some embodiments, the ribs 50 may facilitate fluid path confinement. In some embodiments, the ribs 50 may be disposed at both distal and proximal ends or flanges of the needle hub 12. In some embodiments, the ribs 50 may be disposed along longitudinal edges of the visualization channel 42. In some embodiments, the ribs 50 may interfere with and/or contact an interior of the sleeve 36 of the catheter system 10.

Figure 7C:
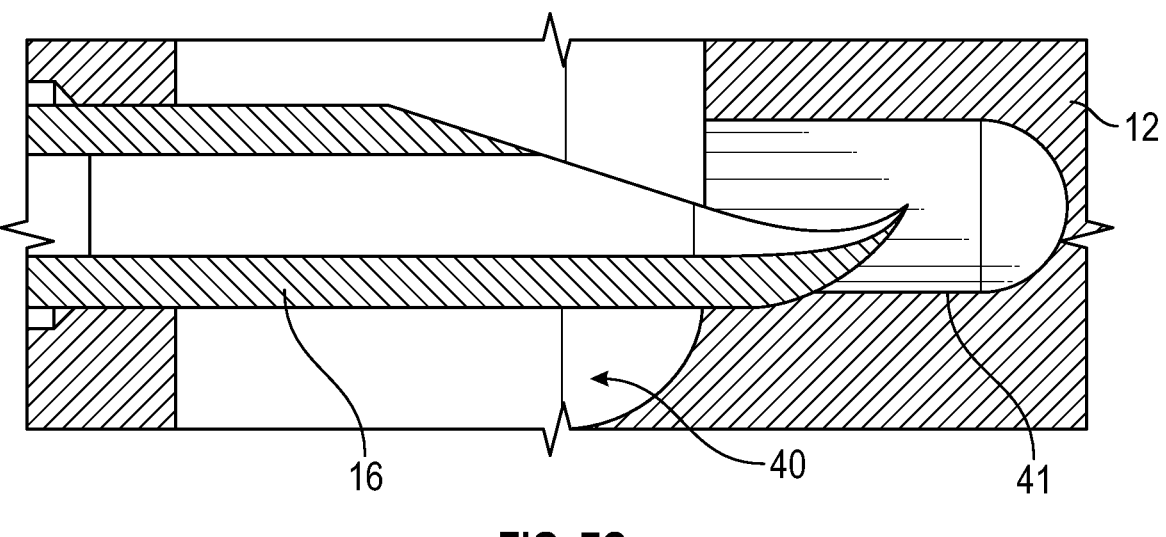
FIG. 7C is a cross-sectional view of an example tunnel that may be disposed in the needle hub of FIG. 7A, according to some embodiments.
Figure 7D:
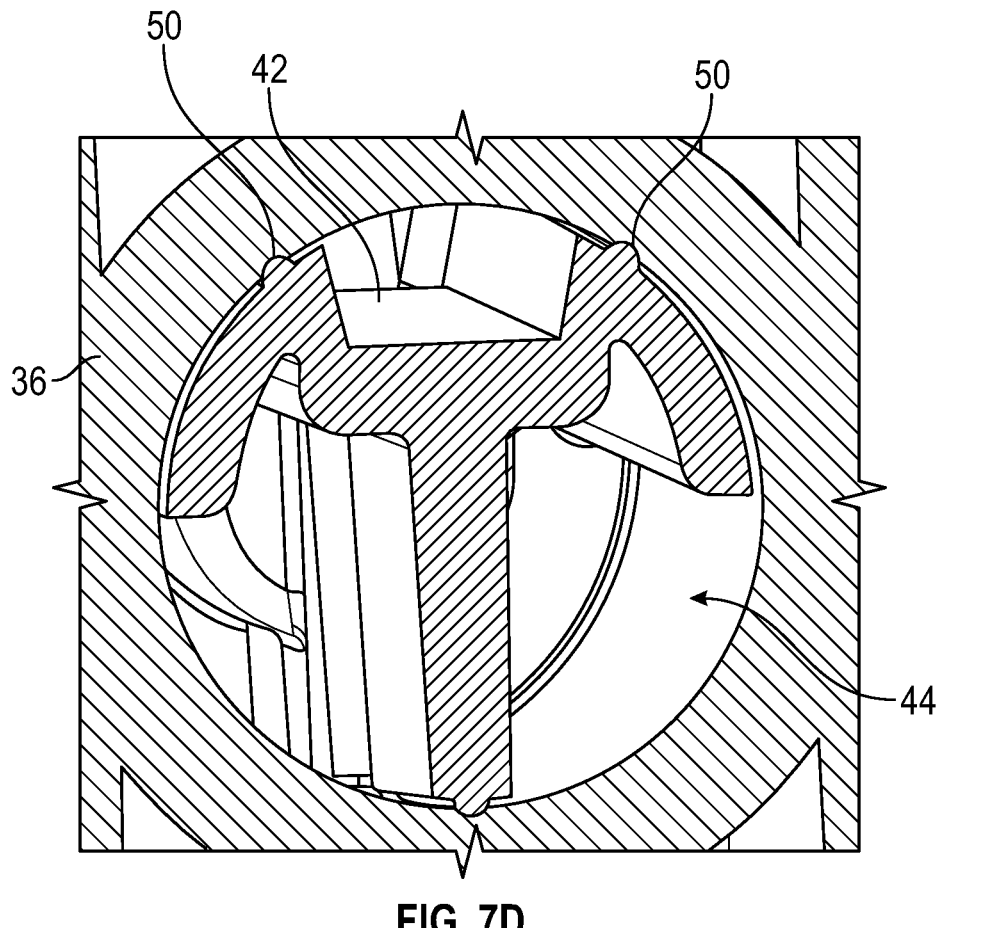
FIG. 7D is a cross-sectional view of the needle hub of FIG. 7B along the line 7D-7D of FIG. 7B, illustrating the needle hub disposed within an example sleeve, according to some embodiments.

Referring now to FIG. 7C, in some embodiments, the pocket 40 may include a tunnel portion 41, which may include and/or protect a proximal end of the cannula 16. Referring now to FIG. 7D, in some embodiments, the reservoir 44 may be disposed on one or both sides of the needle hub 12. FIG. 7C illustrates the reservoir 44 disposed on both sides of the needle hub 12.

In some embodiments, a depth of the visualization channel 42 may be dependent on a gauge of the cannula 16. For example, the depth of the visualization channel 42 may be less when the gauge size is smaller and greater when the gauge size is bigger. Thus, in some embodiments, the visualization channel 42 may be formed in a gauge-specific manner in order to have a consistent duration of the continuous motion and such that the meniscus velocity is well within human recognition domain.

Figure 8A:
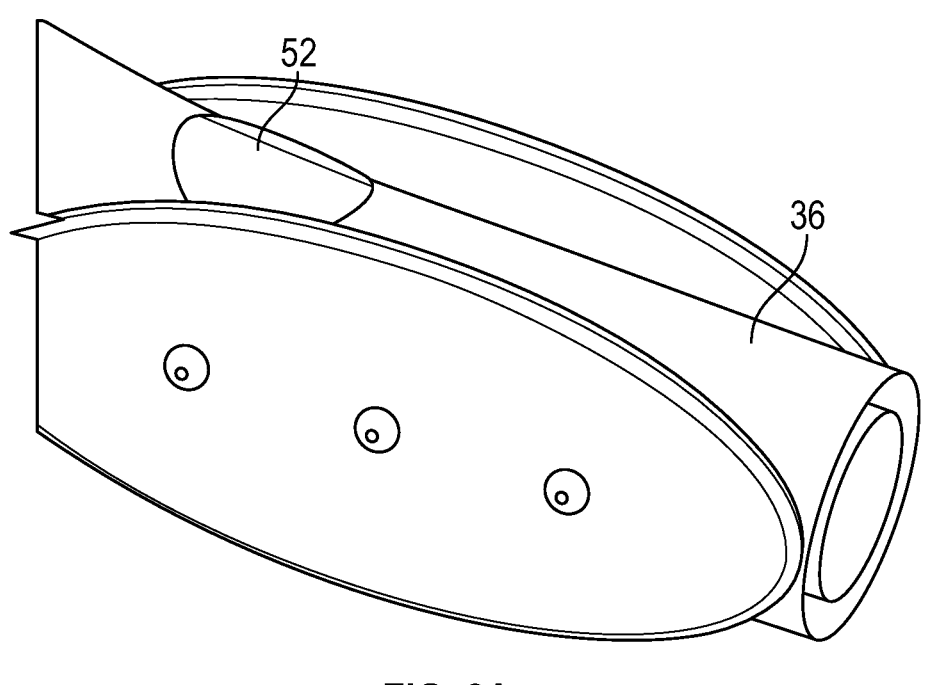
FIG. 8A is an upper perspective view of an example lens, according to some embodiments.
Figure 8B:
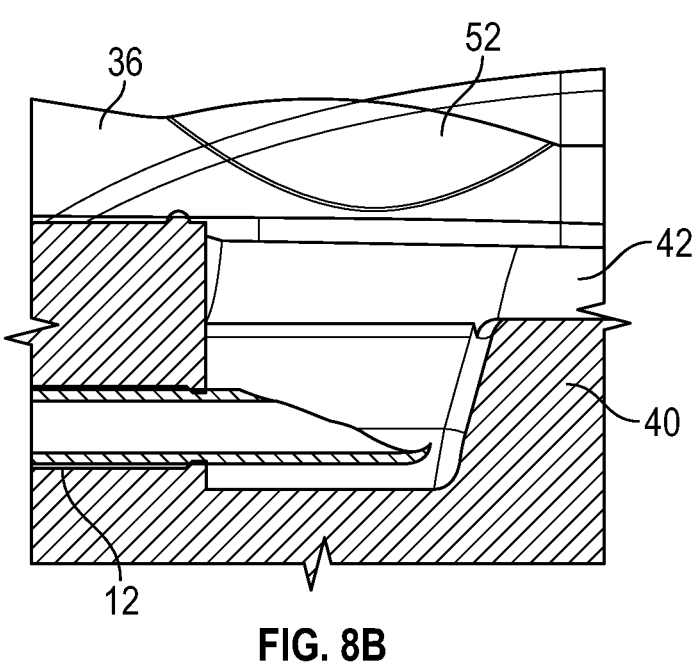
FIG. 8B is a cross-sectional view of the lens of FIG. 8A, according to some embodiments.

Referring now to FIGS. 8A-8B, in some embodiments, a lens 52 may be disposed in the sleeve 36 or another component of the catheter system 10. In some embodiments, the lens 52 may include a single-sided convex lens. In some embodiments, the lens 52 may be built into the sleeve 36 to minimize impact on manufacturing. In some embodiments, the lens 52 may be disposed above the pocket 40 and/or above the proximal end of the cannula 16 to capture presence of blood in the flashback chamber 32 immediately. In some embodiments, the lens 52 may be disposed above the pocket 40 and/or the visualization channel 42. In some embodiments, the lens 52 may span across a top of the sleeve 36, which may provide an adequate viewing angle. In some embodiments, a shape of the lens 52 with respect to an exterior surface of the sleeve 36 may reduce impact of the lens 52 on use techniques.

In some embodiments, the lens 52 may include various shapes, sizes, and curvatures dependent on the particular catheter system 10. For example, the lens 52 may include a double-sided convex lens or an asymmetrical shape with directional distortion. In some embodiments, the lens 52 can be any size that may be integrated on an exterior profile of a component in the catheter system 10. In some embodiments, the lens 52 may be conformal or non-conformal to the exterior profile. In some embodiments, a particular non-conformal lens 52 may be disposed on a stand-out platform on the exterior profile. In some embodiments, the lens 52 may be integrated into an interior of the component. In some embodiments, the lens 52 may be translucent or partially clear. In a preferred embodiment, the lens 52 may be clear. In some embodiments, the lens 52 may be integrated or molded into the sleeve 36.

In some embodiments, the lens 52 may be integrated at various locations in the fluid path for optical amplification. For example, the lens 52 may be on top of the catheter adapter 18 to better visualize blood entering the catheter adapter 18 after primary flashback.

Figure 8C:
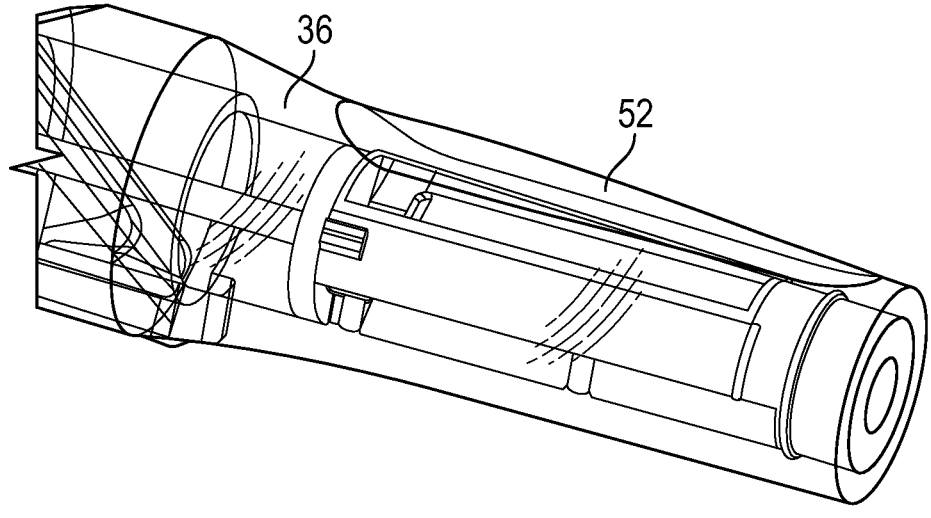
FIG. 8C is an upper perspective view of another example lens, according to some embodiments.

Referring now to FIG. 8C, in some embodiments, the lens 52 may be longitudinally extended along all or a portion of the visualization channel 42, which may provide better view of blood flowing through the visualization channel 42. In some embodiments, multiple lenses 52 may be disposed along the visualization channel 42.

Figure 8D:
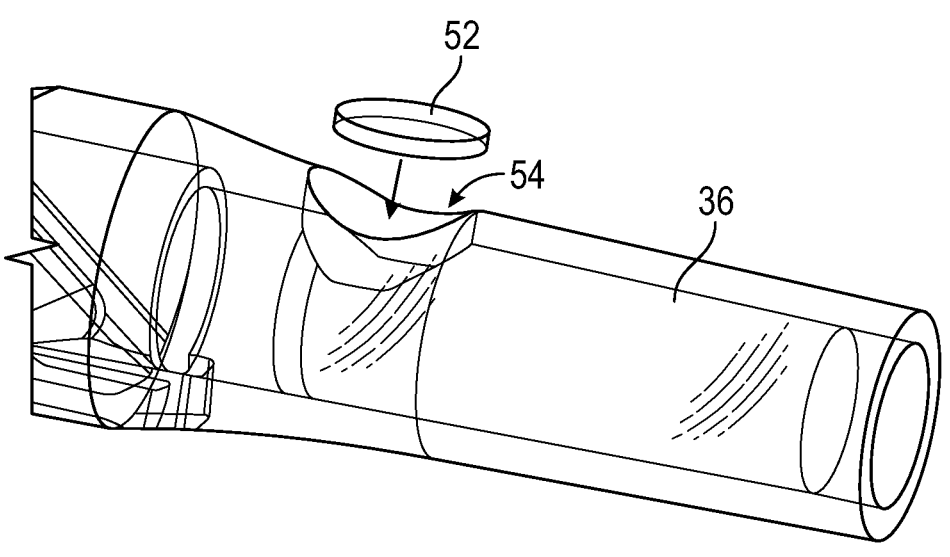
FIG. 8D is an upper perspective view of another example lens, according to some embodiments.

Referring now to FIG. 8D, in some embodiments, the sleeve 36 may be molded to include a cavity or hole 54 in an inner wall of the sleeve 36. In some embodiments, the lens 52 may be inserted into the cavity during assembly, as illustrated in FIG. 8D. As such, in some embodiments, inconsistent wall thickness at a location of the lens 52 may be addressed, and the lens 52 can be independent from restrictions of molding material and geometry.

The catheter system 10 may be compatible with a wide variety of fluid conditions, including overflow conditions. In some embodiments, fluid comes in from the cannula 16 and enters the visualization channel 42. The fluid may then be drained into the reservoir 44 before the fluid is finally held off by the vent 48.

The catheter system 10 may provide various advantages. In some embodiments, the catheter system 10 may provide immediate visualization of blood once it comes out of the proximal end of the cannula 16 or the notch disposed towards the proximal end of the cannula 16. In some embodiments, the catheter system 10 may provide continuous motion of blood flowing through the visualization channel 42 at a steady meniscus velocity of greater than or equal to approximately 0.25 mm/s axially. In some embodiments, the meniscus may flow through an entire length of the flashback chamber 32 in between approximately 5 and 20 seconds. The continuous motion provides a real-time vein confirmation, as opposed to a more static signal, within a duration that covers the catheter insertion process.

In some embodiments, the catheter system 10 may provide enhanced visualization of blood flashback. In some embodiments, blood entering the flash chamber 32 may be forced to a ceiling of the flash chamber 32, e.g., the visualization channel 42 on top of the needle hub 12, which may provide an unobstructed view for the user. In some embodiments, the visualization channel 42 provides a large, substantially flat visualization area, which is a stronger signal than prior art devices in which blood falls to a bottom of a chamber and accumulates in the chamber before a noticeable signal can be generated. In some embodiments, the needle hub 12 is white, which may provide a sharp background contrast upon blood presence of blood in the flashback chamber 32, which may be formed by the needle hub 12 and/or the sleeve 36. In some embodiments, the notch disposed towards the proximal end of the cannula 16 and/or the proximal end of the cannula 16 may be visible within the pocket 40.

In some embodiments, a top portion of the pocket 40 may have a larger diameter than a bottom portion of the pocket 40 and/or the pocket 40 may include drafted walls, facilitating a fast signal when blood presents. In some embodiments, the lens 52 may provide optical amplification of blood disposed within the flashback chamber 32, including the pocket 40 and/or the visualization channel 42. This may be particularly useful for small gauge cannulas and/or catheters. In some embodiments, the catheter system 10 may allow an effective signal for vein confirmation with less than 10 microliters of blood. Prior art devices may require 50-500 microliters to generate an effective signal.

In some embodiments, the catheter system 10 may provide a means of extended vein confirmation that can cover a lengthy period corresponding to the insertion of the catheter 20 within the vein. In some embodiments, the flashback chamber 32 may be used in combination with a primary flashback feature to facilitate vein confirmation throughout various phases of the catheter insertion process. In some embodiments, the various phases may include cannula penetration, "hooding" in which the cannula may be retracted by approximately 2 mm to reduce a risk of transfixing the vein, catheter advancement, and cannula retraction.

In some embodiments, the enhanced flashback visualization features outlined in the present disclosure may be used with any vascular access device that includes a flash chamber. For example, the enhanced flashback visualization features outlined in the present disclosure may be used with a standard or modified plug without an additional component or manufacturing step.

In some embodiments, the visualization channel 42 may be disposed in various locations within a particular catheter system 10. For example, the visualization channel 42 may be disposed on an interior of the sleeve 36 and/or the needle hub 12 may serve to seal the visualization channel 42. As another example and referring now to FIG. 9A, the visualization channel 42 may be co-axial with the cannula 16, which may reduce the volume of the pocket 40.

Figure 9A:
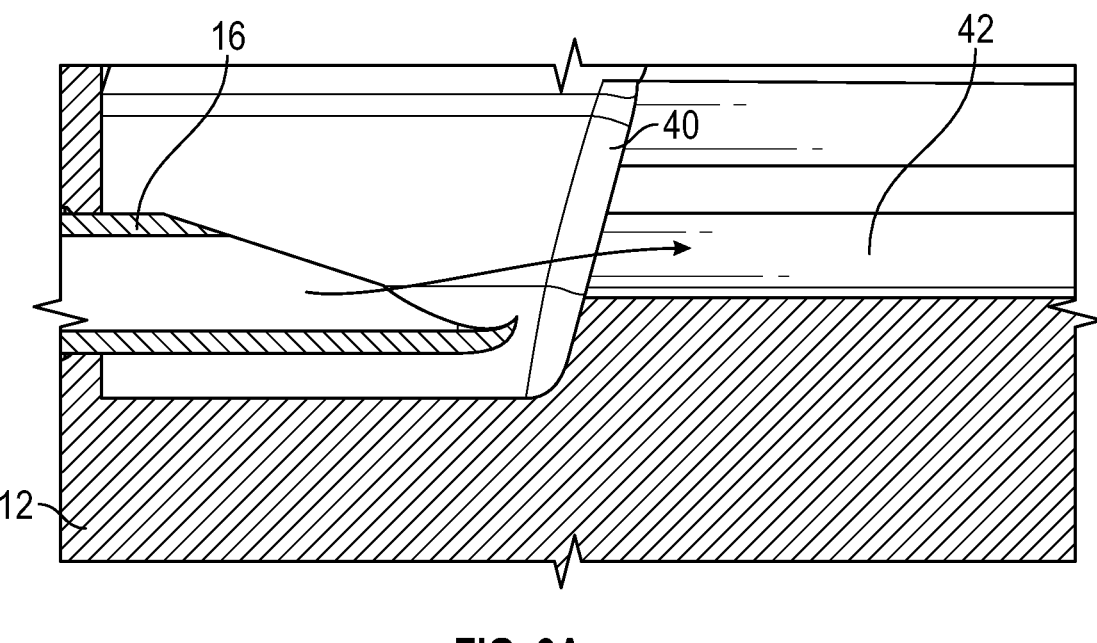
FIG. 9A is a cross-sectional view of a portion of an example visualization channel, according to some embodiments.
Figure 9B:
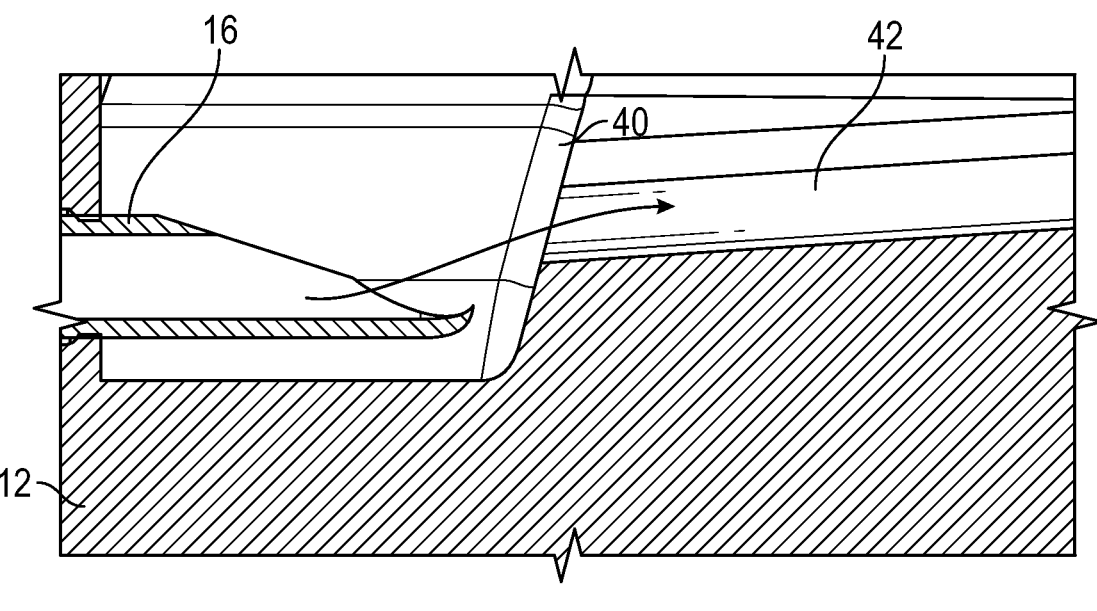
FIG. 9B is a cross-sectional view of a portion of another example visualization channel, according to some embodiments.
Figure 9C:
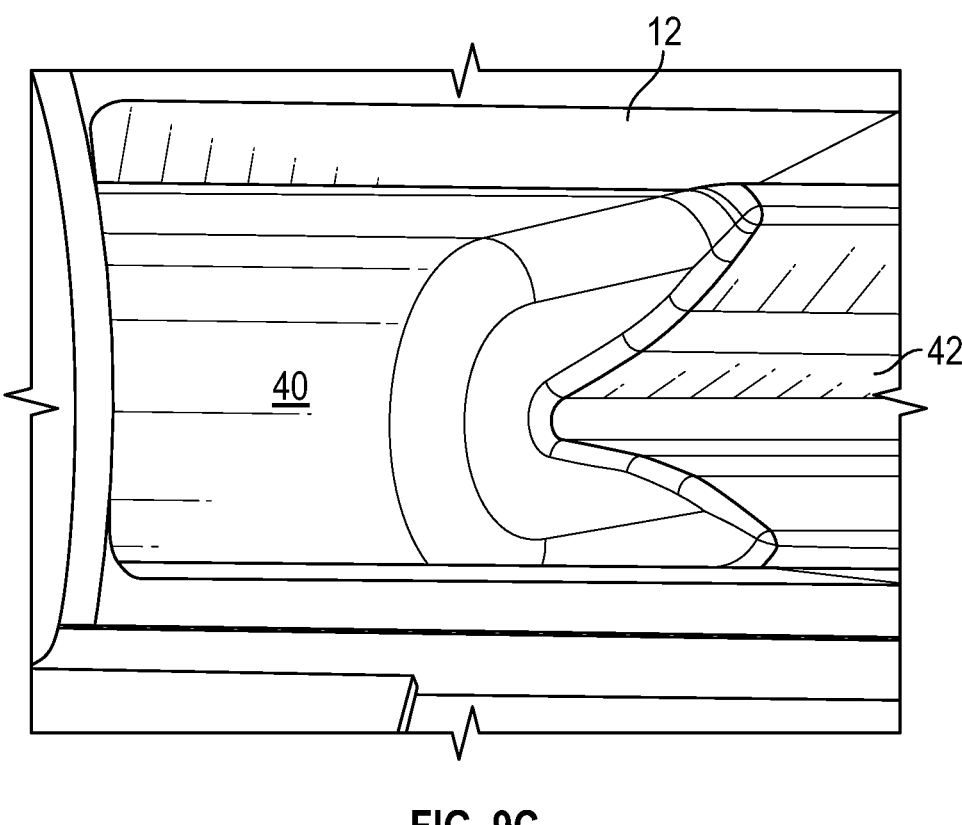
FIG. 9C is a top view of another example visualization channel, according to some embodiments.

Referring now to FIG. 9B, in some embodiments, a center axis of the visualization channel 42 may be transitional between the cannula 16 and a top of the needle hub 12. In these and other embodiments, the visualization channel 42 may be slanted towards the top of the needle hub 12. Referring now to FIG. 9C, in some embodiments, the visualization channel 42 may be tapered. The visualization channel 42 of FIG. 9C may correspond to any of the visualization channels 42 discussed with respect to the present disclosure. As further illustrated in FIG. 9D, in some embodiments, the flashback chamber 32 may be lower and closer to the center axis of the cannula 16, which may generate a steady meniscus velocity. In some embodiments, at least a portion the sleeve 36 disposed above the visualization channel 42 may be transparent.

Figure 9D:
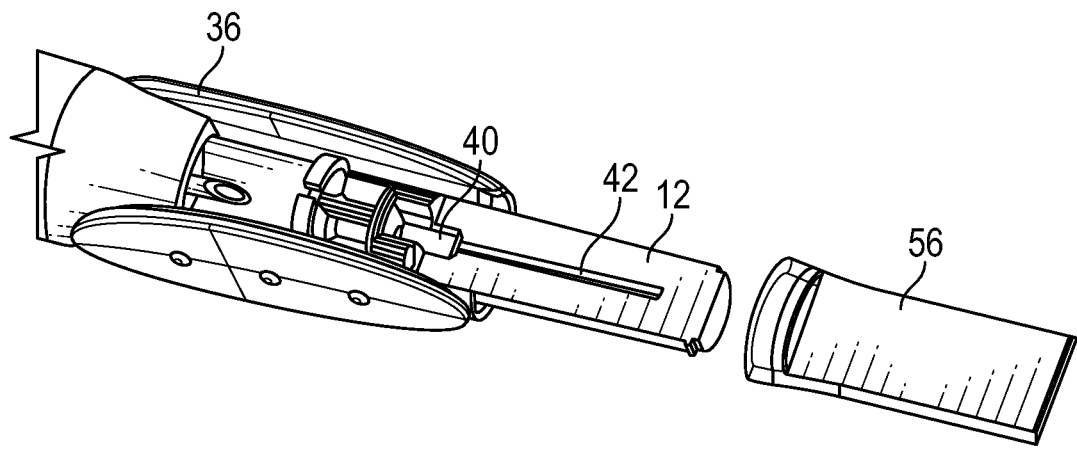
FIG. 9D is an upper perspective view of an example needle hub partially removed from an example sleeve, and an example cover removed from the sleeve, according to some embodiments.
Figure 9E:
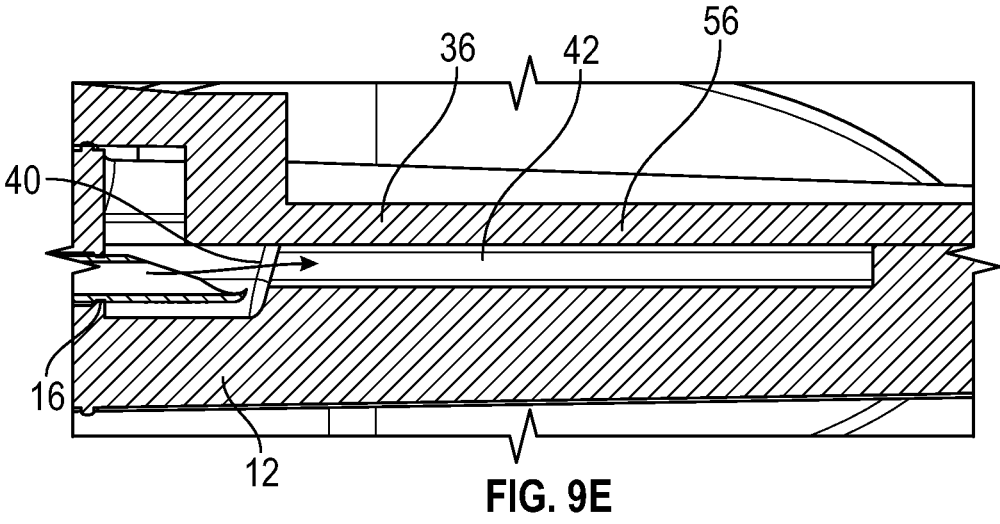
FIG. 9E is a cross-sectional view of the needle hub and cover of FIG. 9D secured within the sleeve, for insertion of the catheter system into the patient, according to some embodiments.

Referring to FIGS. 9D-9E, in some embodiments, a top of the sleeve 36 may include a separate component, such as, for example, a cover 56. In some embodiments, the cover 56 may be transparent or clear. In these and other embodiments, a portion of the sleeve 36 other than the cover 56 may not be limited to any particular material. In some embodiments, an outer diameter of the needle hub 12 and an inner diameter of the sleeve 36 are disposed in a tight geometric tolerance fit. In some embodiments, the cover 56 may be coupled to the sleeve 36 in any number of ways, including, for example, gluing, a mechanical snap fit, etc. Hence, in some embodiments, the coupling of the cover to the sleeve 36 may not depend on a tight geometric tolerance fit between the needle hub 12 and the sleeve 36.

In some embodiments, the visualization channel 42 can include various geometries and locations. In some embodiments, the visualization channel 42 may be straight. In some embodiments, the visualization channel 42 may include a serpentine, curved, or jagged portion to increase a length of the visualization channel 42. In some embodiments, multiple visualization channels 42 may be used in conjunction. In some embodiments, the multiple visualization channels 42 may be parallel. In some embodiments, the visualization channel 42 may be integrated into sides of the needle hub 12 to accommodate grip techniques (e.g., central grip or conventional ported grip) that may partially obstruct a top view of the catheter system 10. In some embodiments, instead of a visualization channel 42, the catheter system 10 may include a visualization area that is an open space for a larger volume of blood to flow through larger cannula gauges. In some embodiments, the open space may include an annular space between the needle hub 12 and the sleeve 36 or an empty chamber separate from the needle hub 12.

Figure 10A:
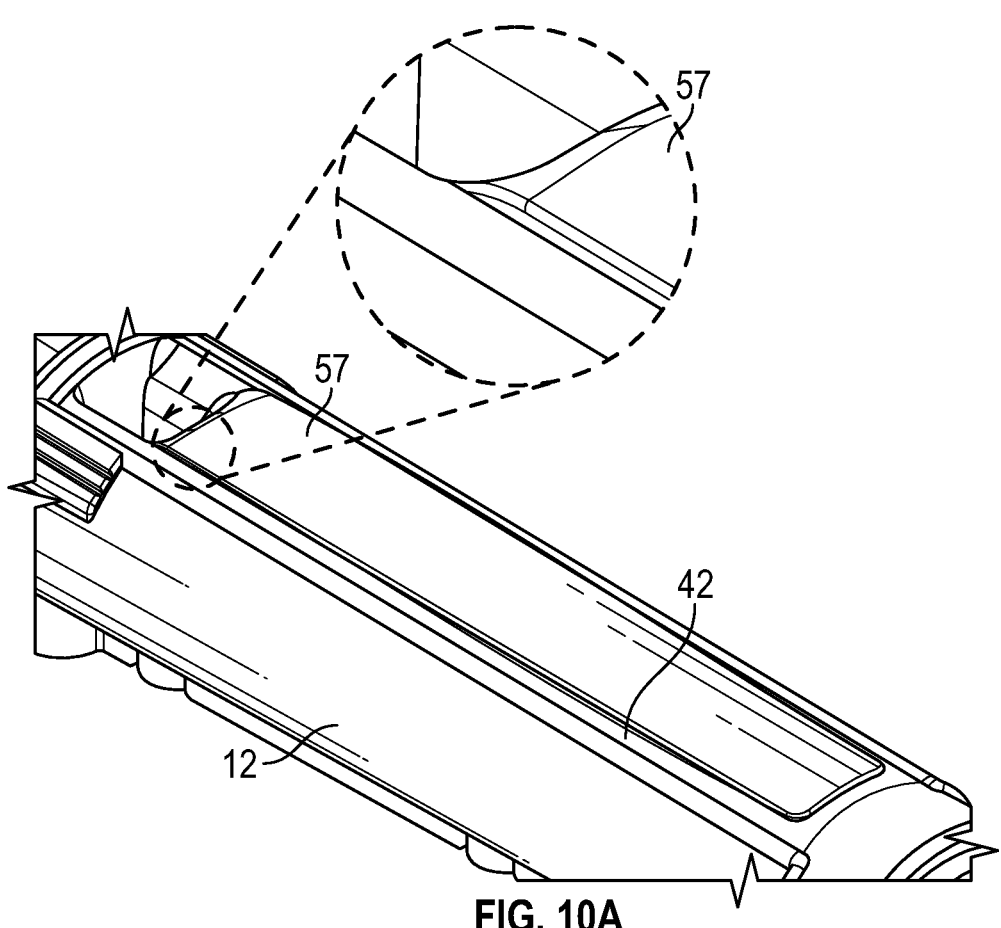
FIG. 10A is an upper perspective view of an example bump, according to some embodiments.

Referring now to FIG. 10A, in some embodiments, a height of the visualization channel 42, or a distance between a bottom and ceiling of the visualization channel 42, may be within sub-millimeter range to trigger capillary effect and/or accelerate blood flow through the visualization when the visualization channel 42 is pre-wetted. In some embodiments, the needle hub 12 may include a bump 57, which may form a microscale gap corresponding to the visualization channel 42 when the needle hub 12 is assembled with the sleeve 36.

Figure 10B:
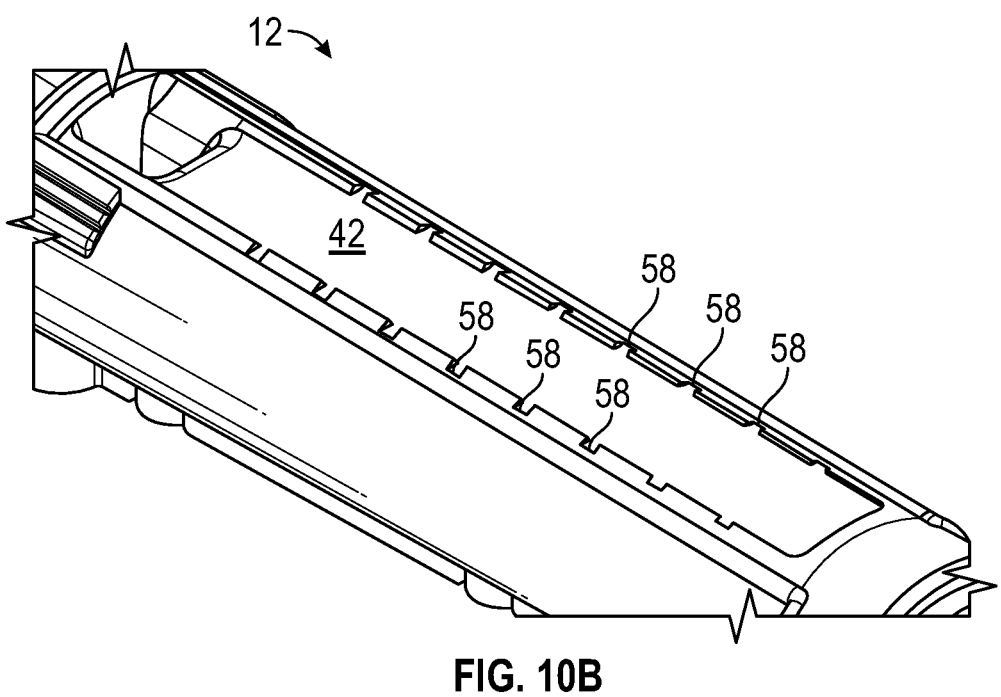
FIG. 10B is an upper perspective view of example indents, according to some embodiments.

Referring now to FIG. 10B, in some embodiments, one or more marks or indents 58 may be integrated along the longitudinal edges of the visualization channel 42 to provide a better indication of travel distance of blood flow within the visualization channel 42. In some embodiments, the marks 58 may be spaced apart. In some embodiments, when blood flows through the visualization channel 42, the blood may color the marks 58 sequentially. In some embodiments, the marks 58 may be molded into the needle hub 12.

Figure 10C:
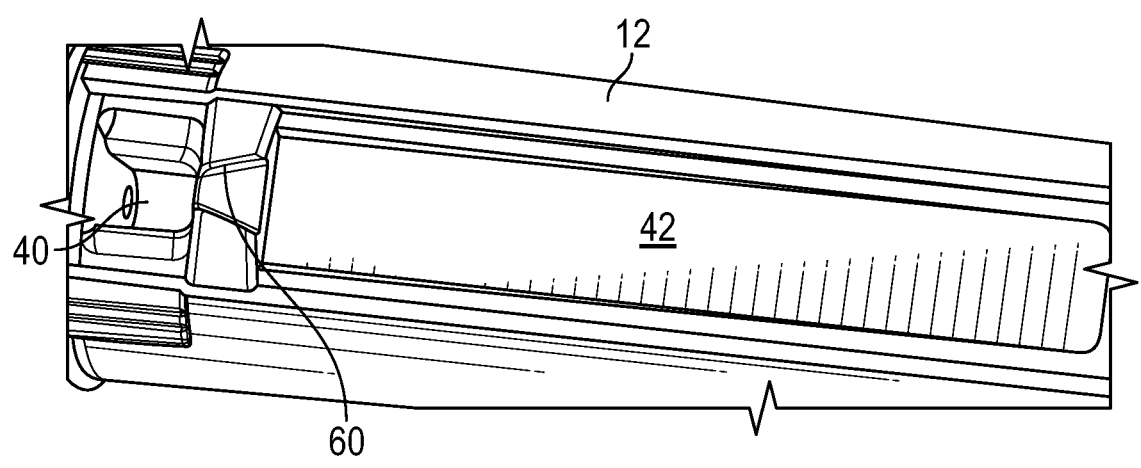
FIG. 10C is an upper perspective view of an example nozzle, according to some embodiments.

Referring now to FIG. 10C, in some embodiments, one or more functional structures may be integrated into the needle hub 12 to provide localized fluid manipulation. For example, a diverging diffuser or nozzle 60 may be molded into the needle hub 12 a distal end of the visualization channel 42 to buffer transient pressure spikes. In some embodiments, a shape of the nozzle 60 may be increase a diameter of the fluid pathway as the blood flows proximally.

Figure 10D:
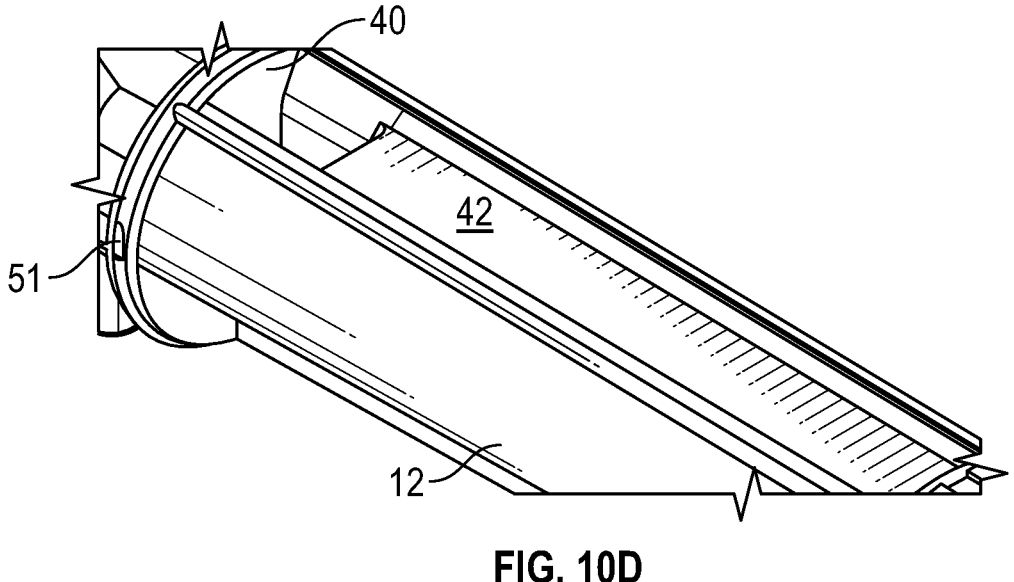
FIG. 10D is an upper perspective view of an example vent, according to some embodiments.
Figure 10E:
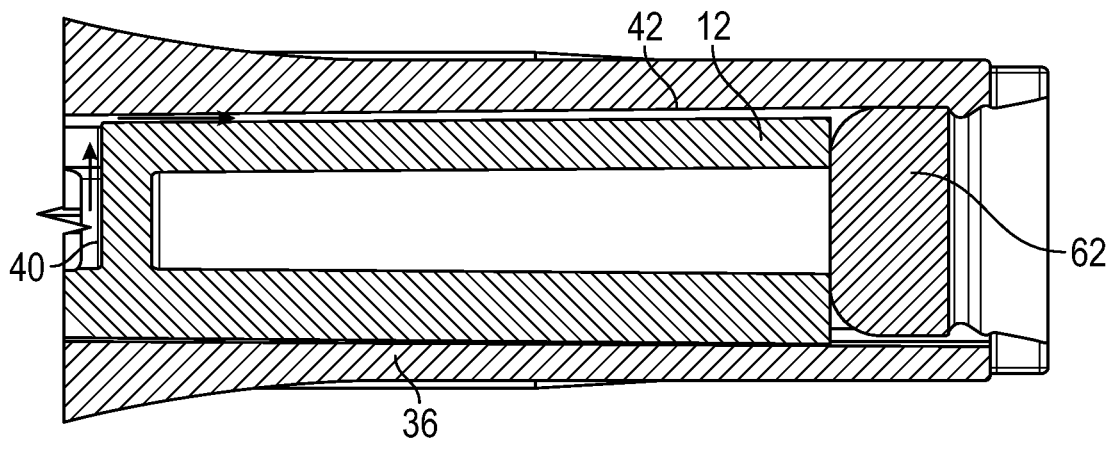
FIG. 10E is a cross-sectional view of an example vent plug, according to some embodiments.
Figure 10F:
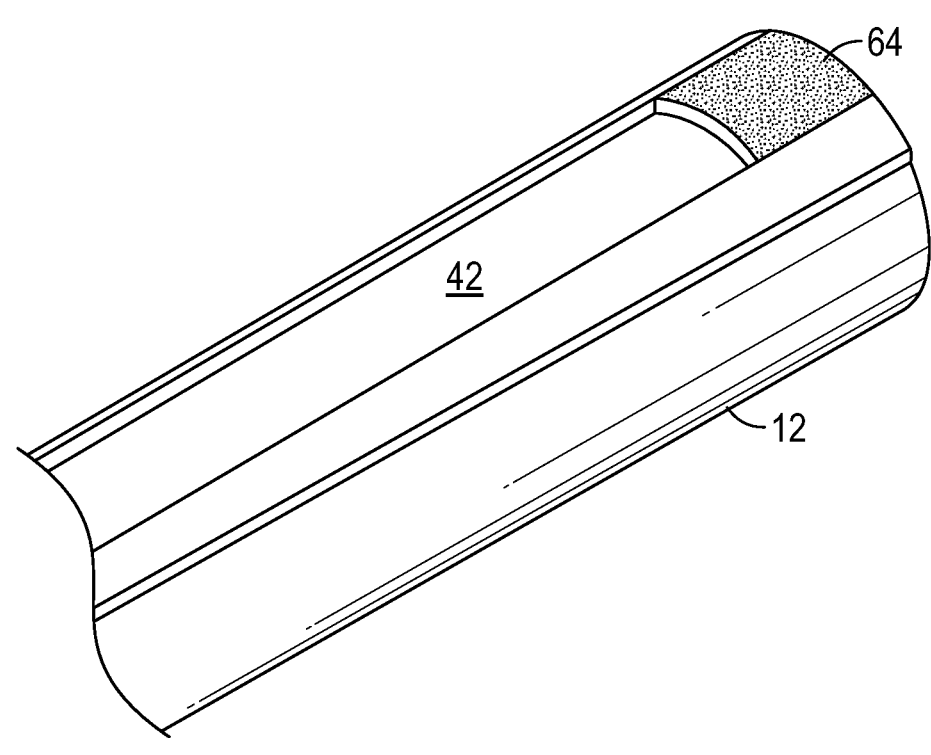
FIG. 10F is an upper perspective view of an example porous material, according to some embodiments.

Referring now to FIG. 10D-10F, in some embodiments, one or more vents may be integrated in the catheter system 10 at multiple locations. In some embodiments, the vents may include the vent 48 discussed with respect to FIG. 7B. In some embodiments, a particular vent 51 may be integrated proximate an exit of the visualization channel 42 for additional fluid restriction and/or throttling for large gauges.

In some embodiments, the vents may be configured to allow air but not fluid to pass. The vents may be created in various ways including, for example, one or more of the following: grooves molded in the needle hub 12, a small cut at a rib 50 (see, e.g., FIG. 10D), a separate porous vent plug 62 proximate a proximal end of the visualization channel 42 (see, e.g., FIG. 10E), and a porous material 64 deposited in at least a portion of the visualization channel 42 (see, e.g., FIG. 10F). In some embodiments, the small cut at the sealing rib 50 may be disposed on a parting line to intentionally compensate molding mismatch. In some embodiments, the porous material 64 may be deposited via over-molding, spun-coating, stamping, etc. In some embodiments, the vents 48 may have mechanical geometries that allow air to pass but prevent fluid from passing. In some embodiments, the vents 48 may be created by paper, fiber, membrane, or other materials with a porosity that allow air to escape while limiting fluid from escaping.

In some embodiments, the catheter system 10 may include various types of catheter adapters 18, regardless of grip technique or type of securement platform 26 (if any). In some embodiments, the catheter system 10 may include straight, integrated, or ported catheter adapters. In some embodiments, the catheter system 10 may include a luer accessible vascular access device with a flow control plug.

In some embodiments, the catheter system 10 may not include primary flashback. However, in some embodiments, the catheter system 10 is compatible with various primary flashback features, such as, for example BD INSTA-FLASH™ technology featuring a notch on the cannula 16 towards a bevel of the cannula 16, a separate fluid path featuring a groove on an exterior of the cannula 16, a double-notch of the cannula 16, a vented extension tube, or another primary flashback feature.

Figure 11A:
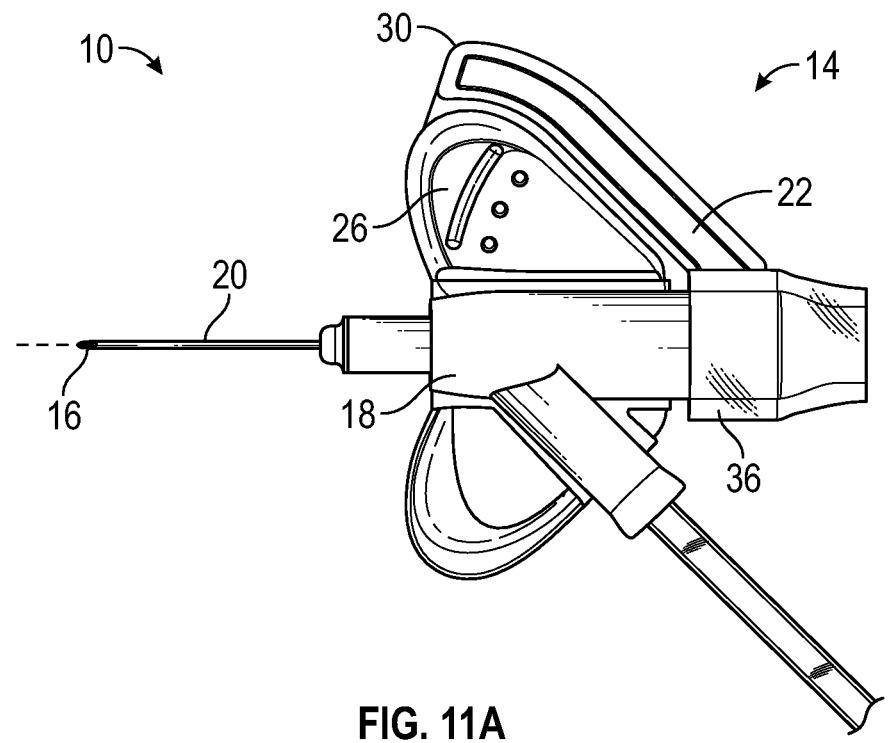
FIG. 11A is a top view of an example catheter system with a shortened sleeve, according to some embodiments.

Referring now to FIG. 11A, in some embodiments, the catheter adapter 18 may not include a central grip area such as the push tab feature 28. In these and other embodiments, the needle hub 12 and/or the sleeve 36 may be shortened significantly, as illustrated, for example, in FIG. 11A. In some embodiments, the catheter adapter 18 may be a two shot or single shot catheter adapter 18. In some embodiments, the catheter adapter 18 may be constructed of a flexible material, such as, for example, one or more of the following: polypropylene, high-density polyethylene, low-density polyethylene, copolyester, polycarbonate, and another polymer material. In some embodiments, the flexible material may allow a securement platform 26 with a foldable hinge.

It is understood that the catheter 20 of the catheter system 10 may include one or more diffuser holes near the distal tip of the catheter 20 for improved flow rates. It is further understood that the one or more components of the catheter system 10 may include an antimicrobial or anti-pathogenic agent. In some embodiments, the antimicrobial or anti-pathogenic agent may include a coating or a component in a fluid pathway of the catheter system 10. In some embodiments, the antimicrobial or anti-pathogenic agent may include an eluting coating or an additive.

Figure 11B:
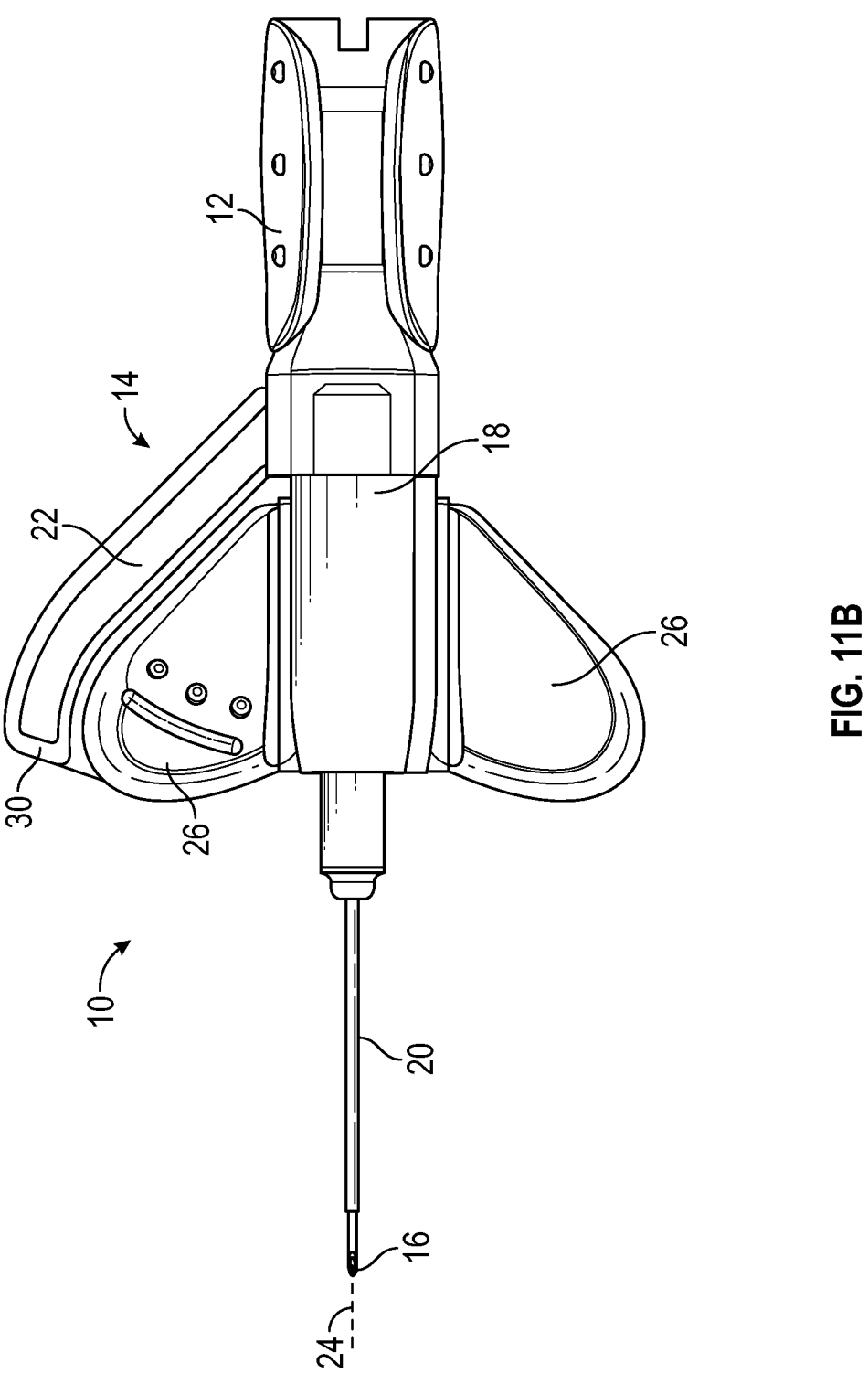
FIG. 11B is a top view of an example catheter system in a non-integrated configuration without extension tubing, according to some embodiments.
Figures 11C, 11D:
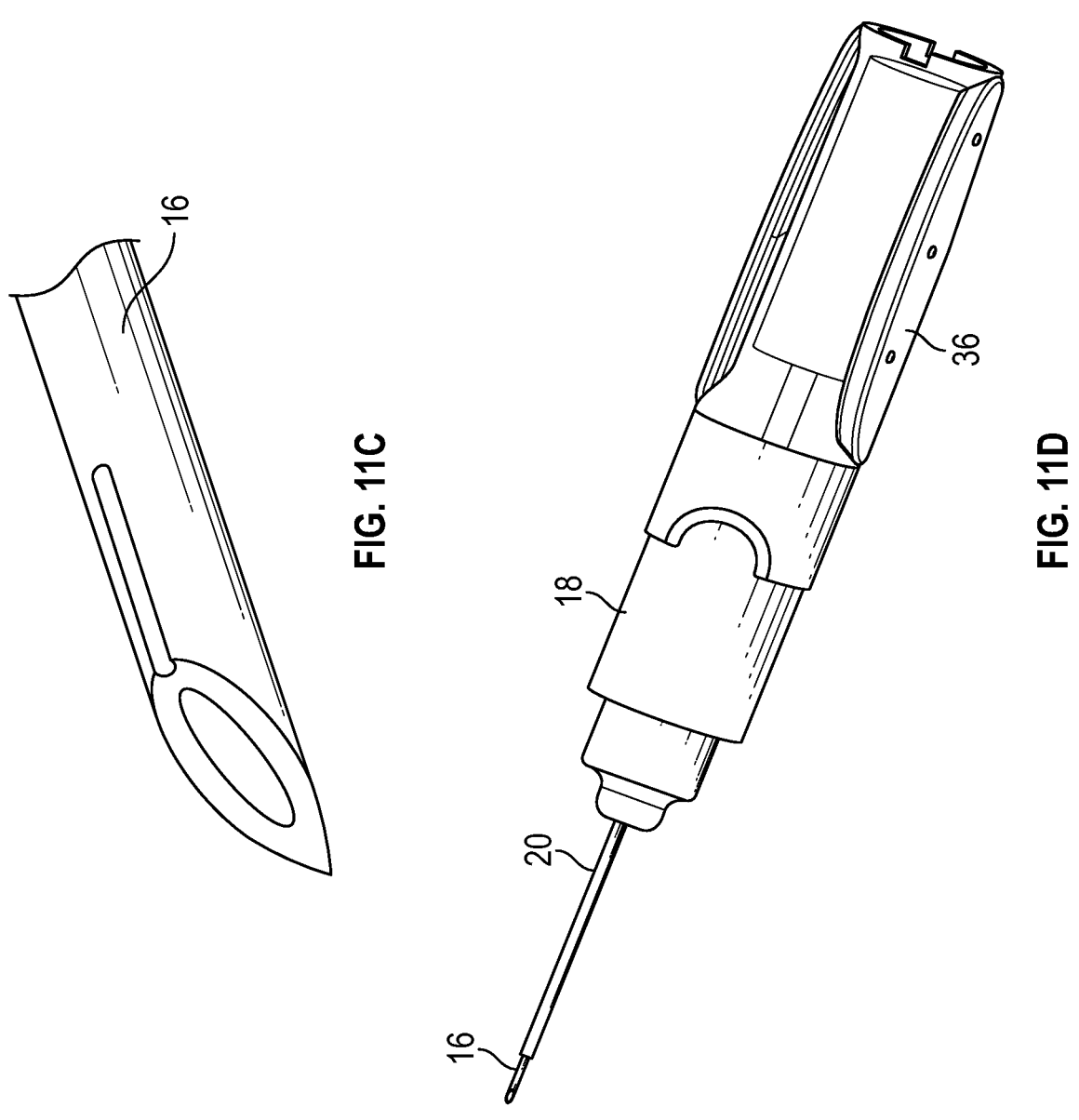
FIG. 11C is an upper perspective view of an example cannula having an external groove, according to some embodiments.
FIG. 11D is an upper perspective view of another catheter system having a non-grip configuration, according to some embodiments.

It is understood that the catheter system 10 may include a single or multi-use blood control valve system. In some embodiments, the blood control valve system may be disposed in one or more luer ports on an end of an extension tube. Referring now to FIG. 11B, in some embodiments, the blood control valve system may be disposed in a non-integrated configuration without extension tubing. Referring now to FIG. 11C, in some embodiments, the catheter system 10 may include an external groove in the cannula 16 for blood visualization. In further detail, in some embodiments, the external groove may allow primary flashback between the cannula 16 and the catheter 20, which may be transparent.

Referring now to FIG. 11D, in some embodiments, the catheter system 10 may have a non-grip or non-paddle grip configuration such that the user does not hold the catheter system 10 using the grip 14. In these and other embodiments, the sleeve 36 may accommodate a number of grip styles, including, for example, a "straight grip" style or a "ported grip" style. The "straight grip" style, in which the thumb and middle finger are on either side of the device and the index finger is used to advance the catheter adapter, is illustrated in FIG. 11D.

Referring now to FIG. 12A-12K, catheter adapters 18 are most often manufactured using a single material for reasons of simplicity and cost. Due to functional constraints placed on the chosen material, catheter adapters 18 comprised of a single material often exhibit tradeoffs in one or more areas. Consider high pressure capability as an example. A catheter adapter 18 designed to support high pressure capability will often reflect a high level of structural rigidity. This rigidity characteristic is in direct contrast with product attributes including patient comfort, user ease-of-use, efficient assembly processes, and part tolerance accommodation.

In some embodiments described in the present disclosure, a second material is introduced into the catheter adapter 18 via an integrated manufacturing process such as two-shot injection molding that allows improvement of a wider range of product attributes. In some embodiments, key catheter-specific fluid path geometry may be produced with an appropriate first material while attributes such as product stabilization, patient comfort, user grip style and flexible product integrity may be improved using the second material. In some embodiments, due to the integrated nature of the assembly process, the addition of the second material may not induce a notable increase in cost or assembly complexity.

Portions of the catheter system illustrated in FIGS. 12A-12K that may optionally include the second material are illustrated with a stippled shading. In some embodiments, the second material may be disposed at locations of the catheter system 10 other than the areas with the stippled shading. Portions of the catheter system 10 that may include the first material are illustrated with a cross-hatched shading. In some embodiments, the first material may be disposed at locations of the catheter system 10 other than the areas with the cross-hatched shading. In some embodiments, areas that include the second material may only partially be constructed of the second material. FIGS. 12A-12F illustrate various catheter adapter 18, according to some embodiments. It should be understood that the embodiments illustrated in FIGS. 12A-12F may be combined, and a particular catheter adapter 18 may include features from one or more of FIGS. 12A-12F.

In some embodiments, the second material is a softer material designed to optimize patient comfort, product stabilization, user grip compatibility, catheter kink resistance, securement compatibility, and component assembly flexibility. In some embodiments, the second material may be flexible or semi-flexible. These improvements are enabled by a multi-material catheter adapter 18 produced in using a highly-integrated manufacturing approach. In some embodiments, the second material may be useful with respect to skin sensitivity and biocompatibility.

In some embodiments, the second material is softer in nature with a lower durometer than the first material. In some embodiments, the introduction of the second material enables the patient comfort improvements via a softer and larger contact area 72 with the skin of the patient. An example contact area 72 constructed of the second material are illustrated in FIG. 12B, according to some embodiments. In some embodiments, a particular contact area 72 may extend to the proximal end of the catheter adapter 18 or beyond the proximal end of the catheter adapter 18, which may further enhance patient comfort and safety as well as play a supporting role in the stability of the adapter 18.

In some embodiments, the securement platform 26 may include the first material and/or the second material. In some embodiments, a profile of a perimeter of the second material may be independent of a perimeter of the first material. For example, the second material perimeter may extend beyond the surface area of the first material or the first material perimeter 70 may extend beyond the surface area of the second material.

Figure 12A:
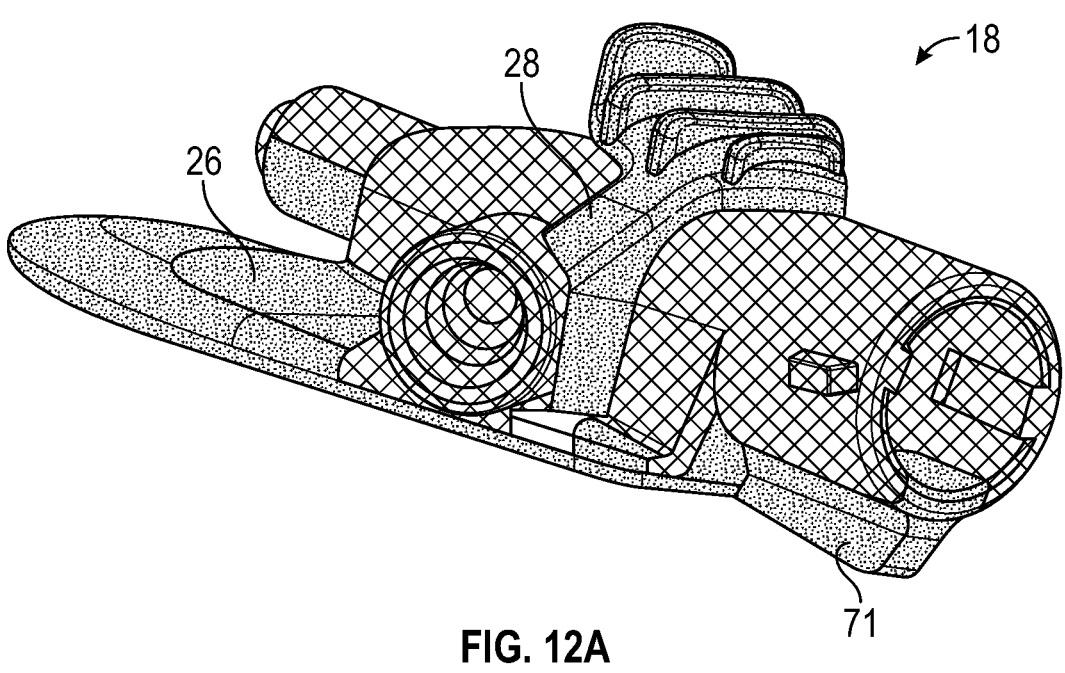
FIG. 12A is an upper perspective view of an example catheter adapter having an example ridge constructed of a second material, according to some embodiments.
Figure 12B:
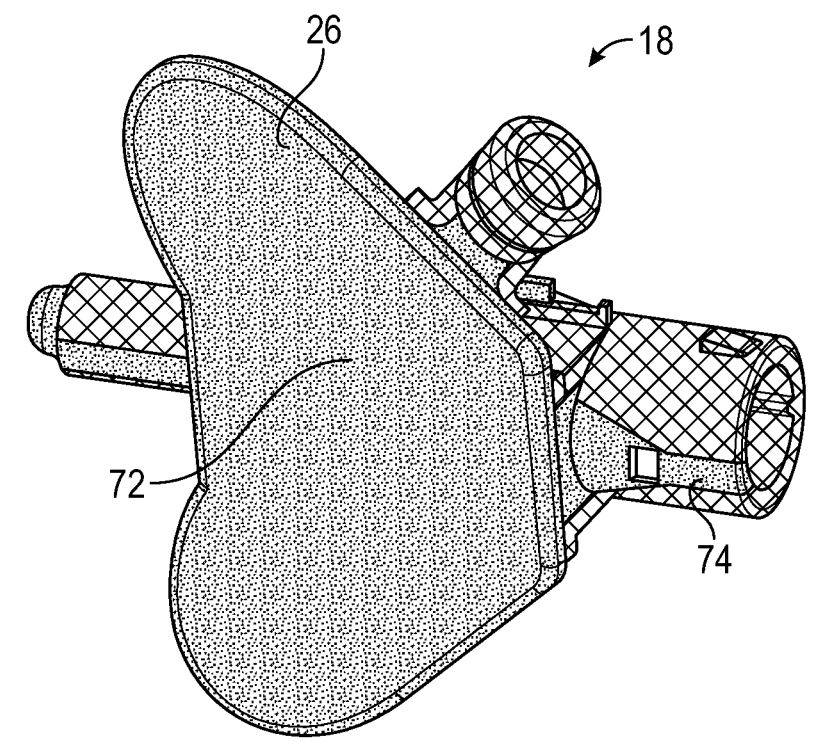
FIG. 12B is a lower perspective view of another example catheter adapter having an example flexible region, according to some embodiments.

As illustrated in FIG. 12A, in some embodiments, a proximal end of the catheter adapter 18 may include a ridge 71, which may be configured to contact the skin of the patient when the catheter system 10 is inserted into the vasculature of the patient.

Figure 12C:
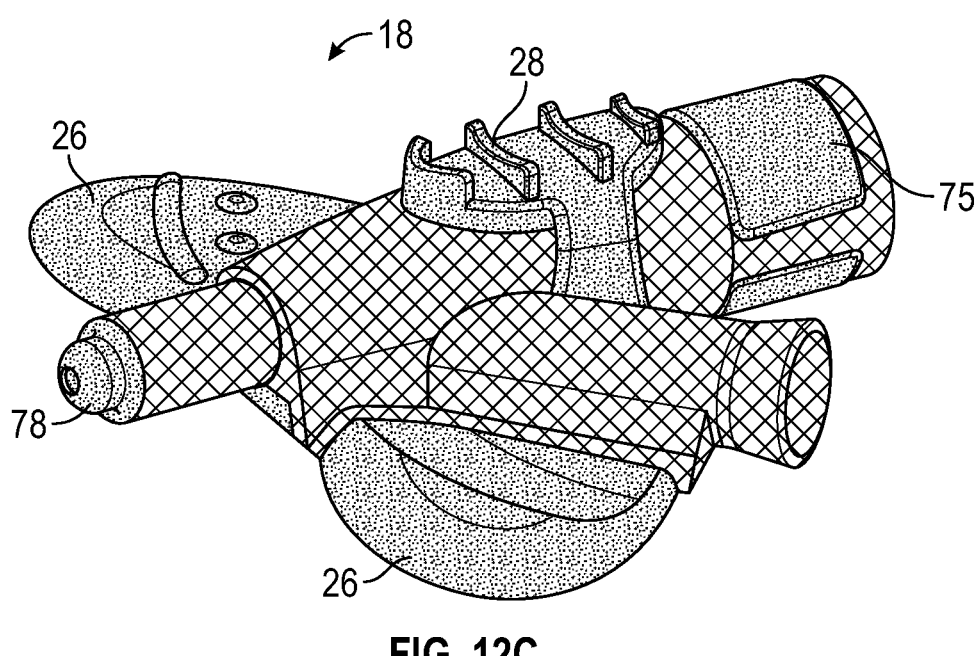
FIG. 12C is an upper perspective view of another example catheter adapter having an example strain relief feature, according to some embodiments.

As illustrated in FIG. 12B, in some embodiments, the introduction of the second material may also facilitate improved post-dressing product stabilization via a softer and larger contact area 72 with the skin and, in some embodiments, a flexible region 74 (see, e.g., FIG. 12B-12C) proximal to the septum 66 (illustrated, for example, in FIG. 1C) designed to deflect under the pressure applied from the dressing. An example of a flexible region 74 and contact area 72 constructed of the second material are illustrated in FIG. 12B. As illustrated in FIG. 12C, in some embodiments, the proximal end of the catheter adapter 18 may include another flexible region 75 disposed at least partially on an upper portion of the catheter adapter 18. In some embodiments, part tolerances may be loosened slightly due to an accommodating nature of the second material.

Figure 12D:
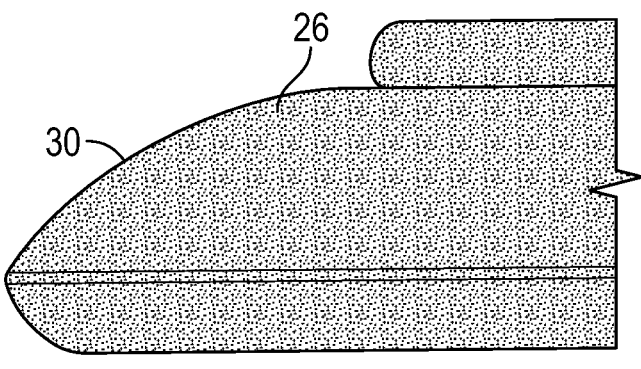
FIG. 12D is a front view of a portion of an example securement platform, according to some embodiments.

In some embodiments, the introduction of the second material also provides improved dressing stabilization via specific features located on the perimeter of the product. For example, the edge 30 of the securement platform 26 may include a tapered upper surface, as illustrated in FIG. 12D. In some embodiments, the tapered round profile may reduce the air gap between securement tape, which may be used to secure the catheter system 10 to the patient, and the catheter adapter 18.

In some embodiments, the benefits of the specific features may not be tied to material durometer. In some embodiments, the introduction of the second material may also provide user grip compatibility via the introduction of a flexible central push tab feature 28 and/or a flexible securement platform 26 to accommodate a traditional winged insertion style. Examples of the flexible central grip area or push tab feature 28 and the flexible securement platform 26 constructed of the second material are illustrated in FIG. 12A.

Figure 12E:
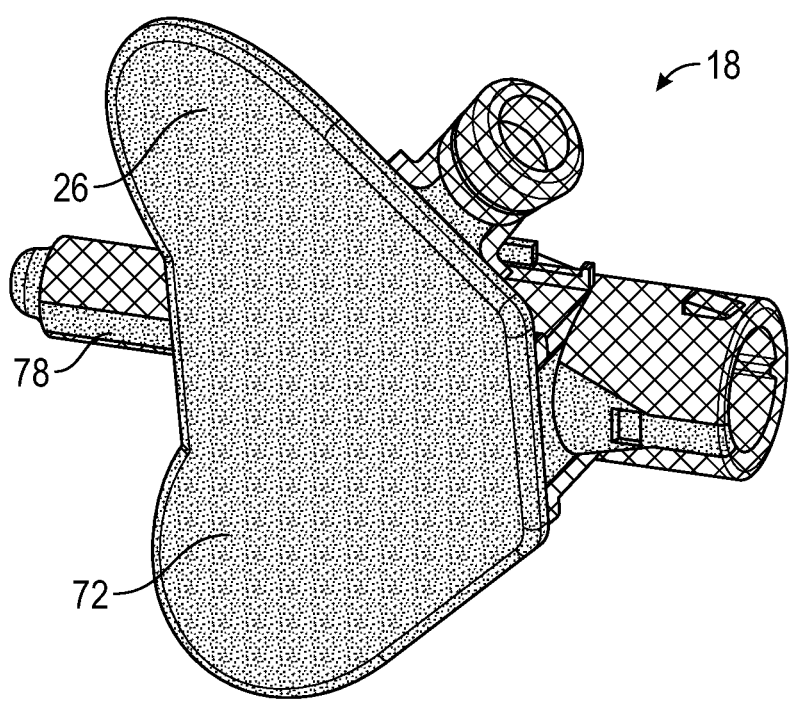
FIG. 12E is a lower perspective view of another example catheter adapter having an another example strain relief feature, according to some embodiments.

As illustrated in FIG. 12E, in some embodiments, the introduction of the second material provides improved catheter 20 kink resistance via the introduction of a strain relief feature 78 at the distal end of the catheter adapter 18. An example strain relief feature 78 constructed of the second material is illustrated in FIG. 12E. In some embodiments, the strain relief 78 may be designed to be as short as possible to avoid negatively influencing system stiffness. In some embodiments, the effectiveness of this shortened design is a byproduct of the second material flow path via a wide channel that also deflects under catheter loading.

Figure 12F:
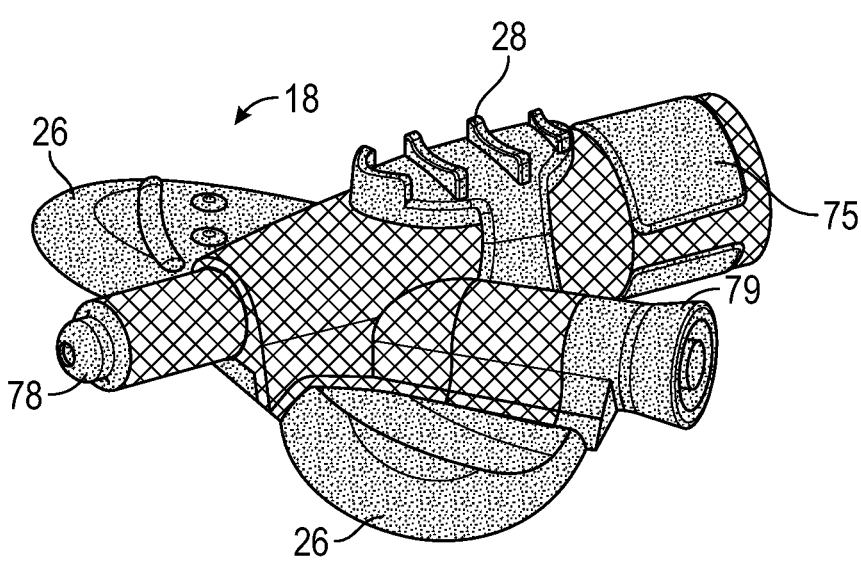
FIG. 12F is an upper perspective view of another example catheter adapter having another example flexible region, according to some embodiments.

In some embodiments, the introduction of the second material may provide improved extension tube kink resistance via the introduction of a strain relief feature 78 at a junction coupling the extension tube to the catheter adapter. An example of the strain relief feature 68 at the junction and constructed of the second material is illustrated in FIG. 12F. In some embodiments, the strain relief feature 78 may be further described in U.S. patent application Ser. No. 15/286, 212, filed Oct. 5, 2016, entitled "Extension Tubing Strain Relief," which is incorporated by reference. In some embodiments, securement features added to an extension tube port, for example, may improve a lay of the dressing visually and/or by providing strain relief. As example, FIG. 12F illustrates a side port that includes a strain relief feature 79.

Figure 12G:
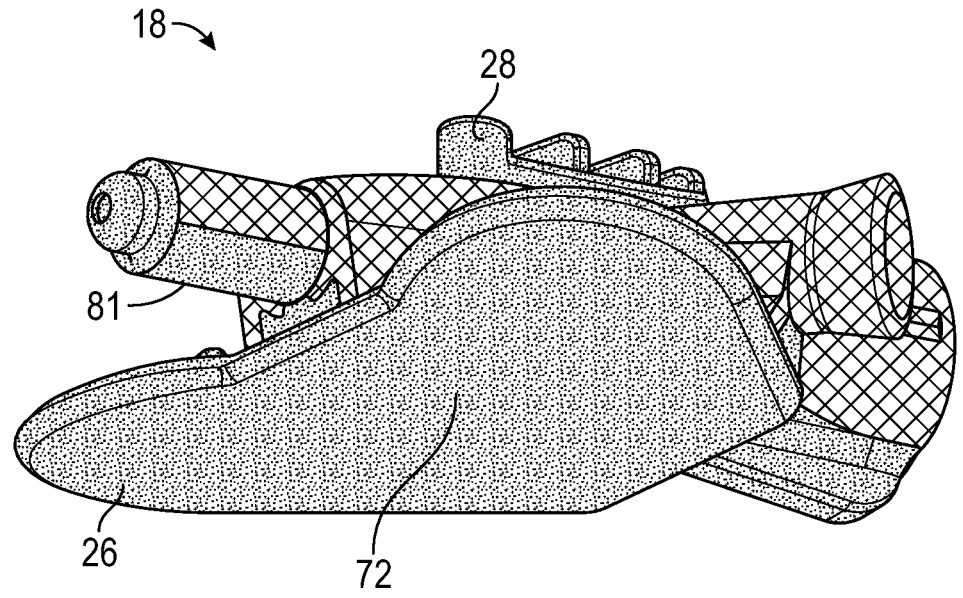
FIG. 12G is a lower perspective view of another example catheter adapter having an another example strain relief feature, according to some embodiments.

As illustrated in FIG. 12G, in some embodiments, the second material, which may be lower-durometer, may be formed to mimic a semi-circular shape 81 to target stress reduction in off-axis areas, potentially accommodating a wider array of loading scenarios. In some embodiments, the second material may include a surface layer of the catheter adapter 18. In some embodiments, the second material may extend all the way through a wall of the catheter adapter 18.

Figure 12H:
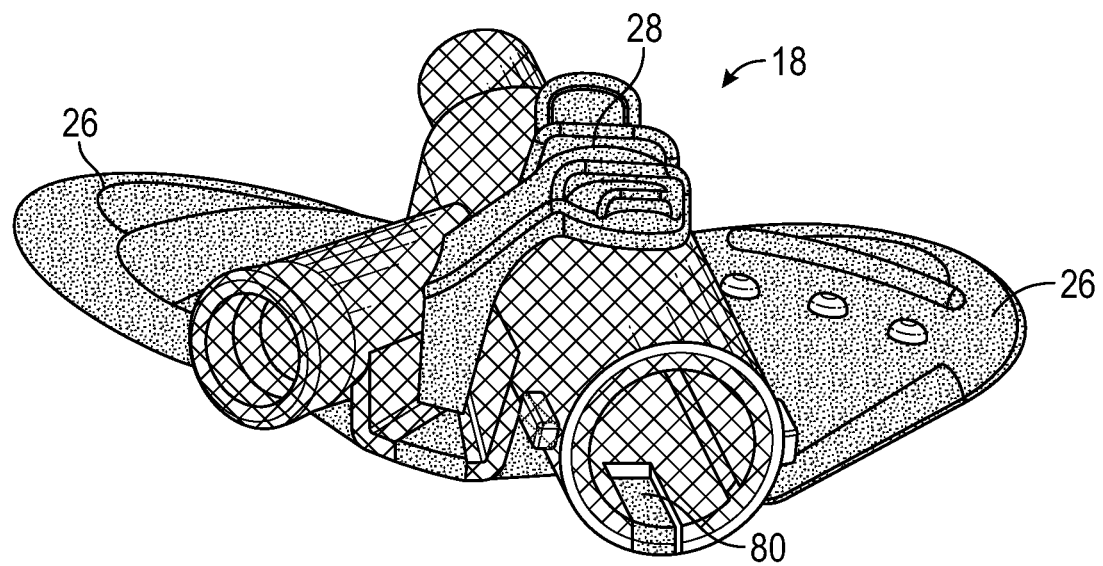
FIG. 12H is a rear view of another catheter adapter having an example notch constructed of the second material, according to some embodiments.

In some embodiments, the second material may allow reduced assembly complexity of, for example, safety mechanism components. In some embodiments, under the force of assembly, the deflection of the second material at a location proximate a safety mechanism component, such as, for example, a notch 80 that may be configured to contact a needle safety clip. An example notch is illustrated in FIG. 12H. second material In some embodiments, the second material may be coupled to the first material in a highly integrated manufacturing sequence such as two-shot injection molding. In some embodiments, the first material and second material may be formulated to enable chemical-level bonding as opposed to purely mechanical bonding via geometric features. In some embodiments, the second material is a lower-durometer material in the approximately 50 A to 95 A range, depending on product and application. In some embodiments, the second material may include a lower-durometer material in the approximately 10 A to 95 A range. In some embodiments, certain additives may be compounded to the base material of the second material to improve characteristics such as comfort against skin and improved lubricity. In some embodiments, the catheter adapter 18 utilizes the second material to improve many aspects of the product including, not limited to, patient comfort, user grip comfort and compatibility, catheter kink resistance, improved securement and stabilization, and reduced cost burden due to ease of assembly and looser part tolerances.

In some embodiments, the first material may be rigid or semi-rigid. In some embodiments, the first material may be flexible. In some embodiments, the first material may be more stiff or hard than the second material. In some embodiments, the first material and/or the second material may include plastic, an elastomer such as silicone rubber, or another suitable material. In some embodiments, the first material may be disposed proximal to the septum 66. In some embodiments, the catheter system 10 may include the second material, but there may be no current integration of ease of assembly and looser part tolerance-specific features.

Figure 12I:
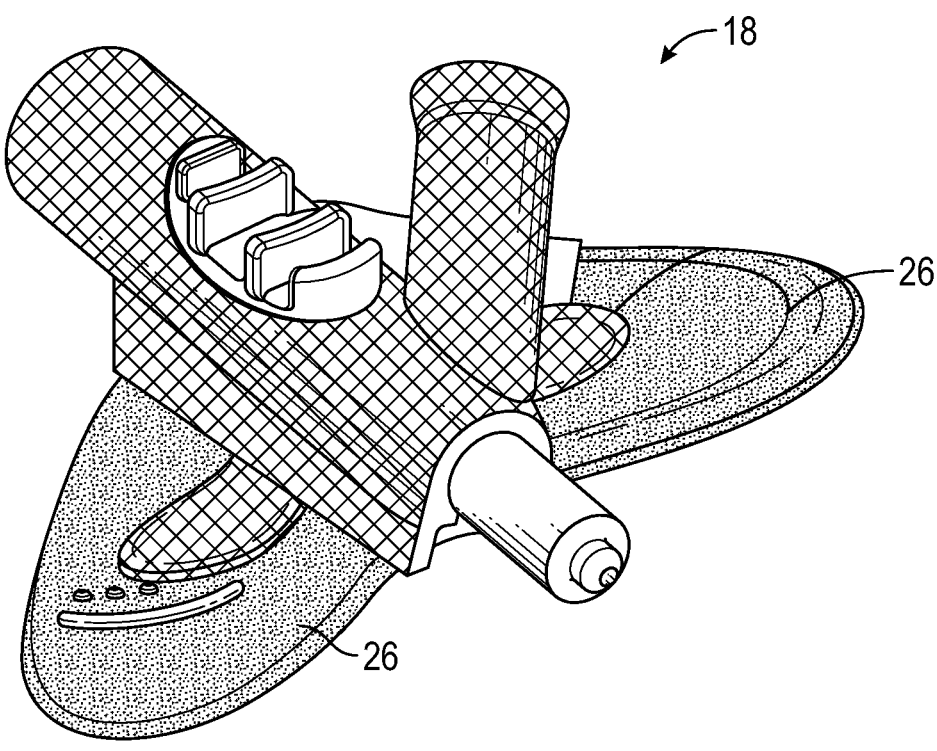
FIG. 12I is a partial cutaway view of another catheter adapter, illustrating a first material disposed within the securement platform 26 proximate the second material, according to some embodiments.
Figure 12J:
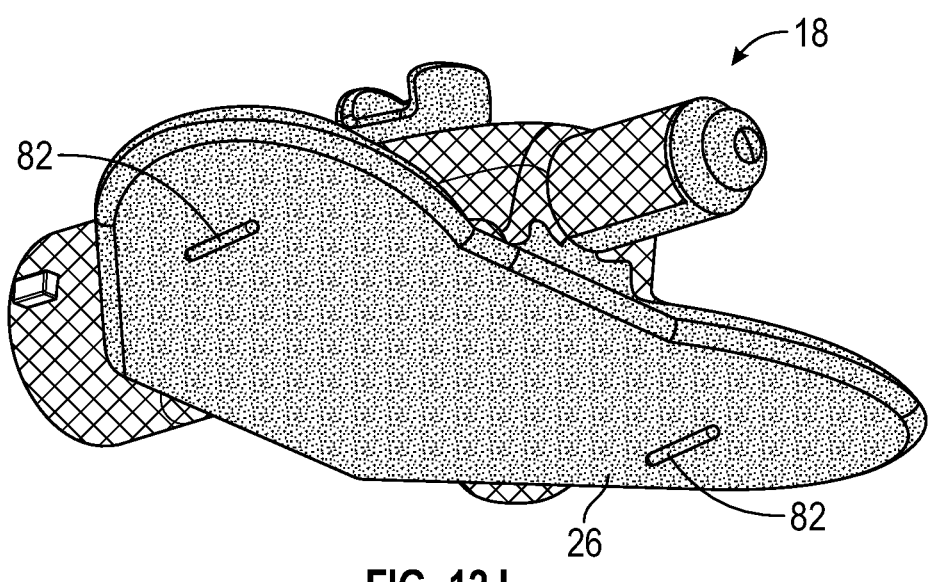
FIG. 12J is a lower perspective view of an example friction reducer, according to some embodiments.

As illustrated in FIG. 12I, in some embodiments, the first material may extend into the second material to provide shape and/or support. In these and other embodiments, the first material may not be outwardly visible. In some embodiments, the first material may extend beyond surfaces of the second material in order to improve product functionality. In these and other embodiments, the first material may act as one or more interface friction reducers 82, as illustrated, for example, in FIG. 12J. In some embodiments, the friction reducers 82 may decrease friction between the catheter system 10 and the skin of the patient and/or the wing 22. In some embodiments, one or more of the interface friction reducers 82 may include a protrusion.

Figure 12K:
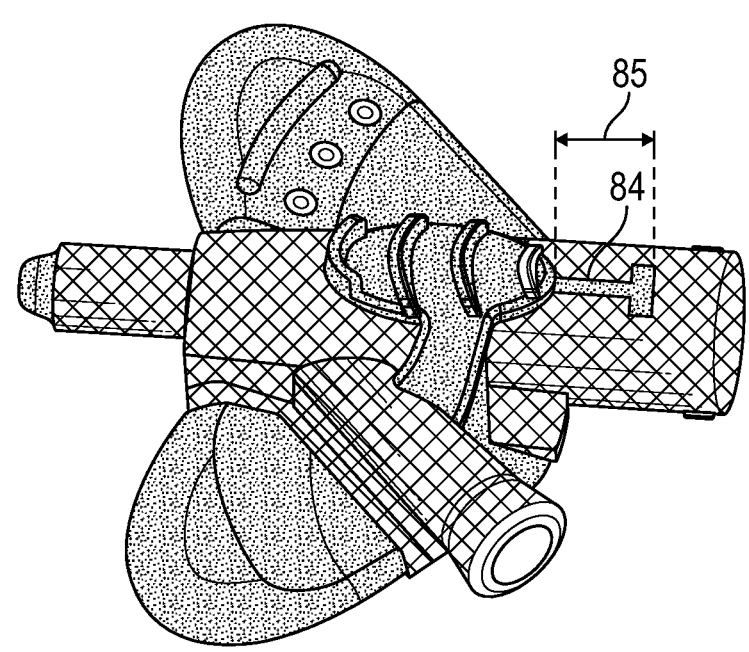
FIG. 12K is an upper perspective view of an example withdrawal indicator feature, according to some embodiments.

Referring now to FIG. 12K, in some embodiments, the second material may be used for additional purposes such as adding a withdrawal indicator feature 84. A length 85 of the withdrawal indicator feature 84 may vary. In some embodiments, the withdrawal indicator feature 84 may be about 2 mm.

Figure 13:
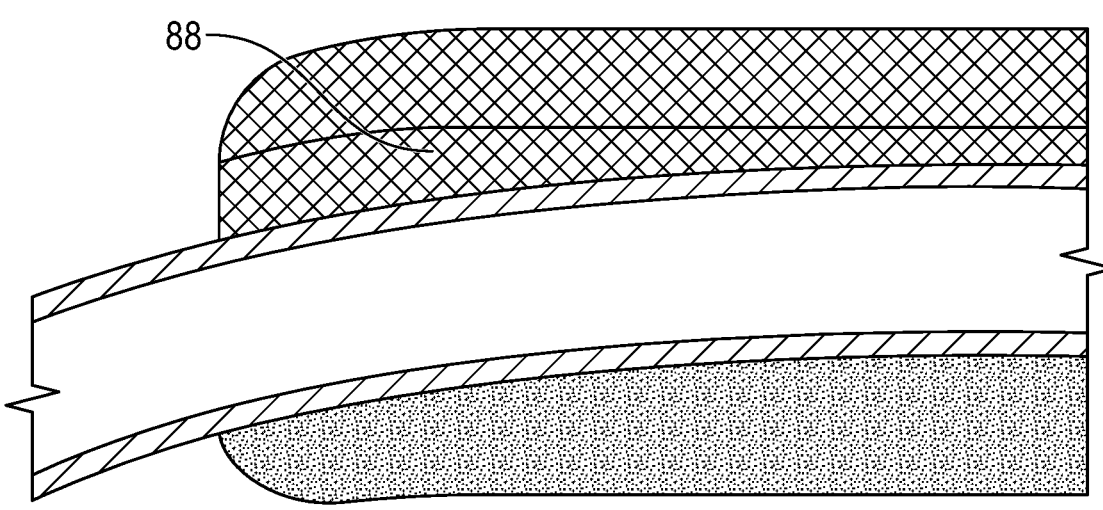
FIG. 13 is a cross-sectional view of an example strain relief feature, according to some embodiments.

FIG. 13 illustrates an example strain relief feature 86, which may include or correspond to any of the strain relief features 78 and/or 79 described with respect to FIG. 12. In some embodiments, the strain relief feature 86 may be integrated into the catheter system 10 via the second material and/or may be as short as possible for various reasons. In some embodiments, the strain relief feature 86 may form a channel 88. In some embodiments, an underside of a distal end of the channel 88 closest to the skin of the patient may include the second material, which may enable deflection based on loads placed on the catheter 20. In some embodiments, placement of the channel 88 may reduce potential stress concentrations between the first material and the second material in an area of significant and direct loading. In some embodiments, in response to a 0.5 inch deflection applied at a single node at the distal end of the catheter, a single material catheter adapter 18 may experience peak stresses at the distal end of the single material catheter adapter 18 in a range 10-50% higher than peak stresses at an equivalent location on another multi-material catheter adapter 18 that includes the strain relief feature 86 with the second material.

In some embodiments, the strain relief feature 86 at least partially constructed of the second material may impact a bend profile of the catheter 20 as the catheter 20 rests against the skin of the patient. In some embodiments, the strain relief feature 86 having the second material leads to a larger bend radius in the catheter 20 and a reduced insertion angle into the vein of the patient.

In some embodiments, the strain relief feature 86 may be designed to work within a specific angular range depending on product requirements, for example. As illustrated in FIG. 13, in some embodiments, the strain relief feature 86 includes both the first material and the second that extend to the distal end of the catheter adapter 18 to limit an impact of the strain relief function. As illustrated in FIG. 13, in some embodiments, the strain relief feature 86 may include a mix of the primary and second materials depending on, for example, desired performance characteristics. In some embodiments, the strain relief feature 86 may include an antimicrobial agent to improve the indwell of the catheter 20. In some embodiments, the antimicrobial agent may be an additive in the first material and/or the second material. In some embodiments, the antimicrobial agent may include a coating applied to the strain relief feature 86.

Figure 14:
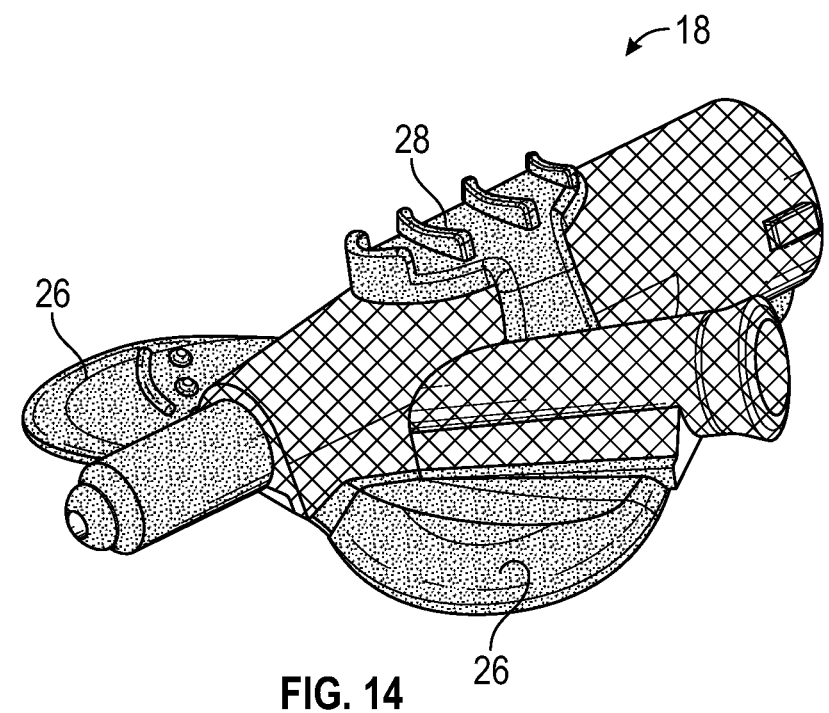
FIG. 14 is an upper perspective view of another catheter adapter having a distal end constructed of the second material, according to some embodiments.

As illustrated in FIG. 14, in some embodiments, the second material may encompass a full diameter at the distal end of the catheter adapter 18, providing strain relief. In some embodiments, the entire distal end of the catheter adapter 18 may be constructed of the second material.

The catheter insertion process may require a high level of skill. Persons challenged with building and supporting an insertion skill set often develop preferences and techniques based on the equipment they work with. In the case of peripheral IV catheters, a number of insertion grip styles have evolved. Through manipulation of geometry and materials, catheter system 10 designs have changed to better support the refinement and mastering of these grip styles.

One of the more widely used grips involves a pinching action between the thumb and forefinger. In some embodiments, a hub component 31 of the catheter system 10 may include the needle hub 12 and/or the sleeve 36, which may separate from the catheter adapter 18. In some embodiments, the hub component 31 may include a wing-like feature (which may be referred to in the present disclosure as "wing 22") to act as a point-of-contact for catheter insertion as well as cannula withdrawal and removal. In some embodiments, the wing 22 may be captured between the thumb and forefinger to further describe the pinching action. During the insertion process, the wing 22 may act as a grip stabilizer and control feature.

In some embodiments, the catheter adapter 18 may include one or more stabilization features to benefit patients and users. In some embodiments, the stabilization features may extend medially and/or laterally from the catheter adapter 18. In some embodiments, the stabilization features may include one or more wings 33, which may be part of the securement platform 26 and/or extend outwardly from the catheter adapter 18. In some embodiments, combining a catheter adapter 18 with a stabilization feature and the hub component 31 with the wing 22 yields a more complex interface between the catheter adapter 18 and the hub component 31. In some embodiments, as opposed to pinching solely the wing 22 on the needle hub 12 during insertion, the interface may allow the user to pinch the wing 22 in combination with the stabilization feature on the catheter adapter 18.

Upon completion of a successful initial insertion of the catheter 20, the user may then separate the hub component 31 from the catheter adapter 18 prior to securing the catheter adapter 18 to the patient. In some embodiments, the catheter system 10 described in the present disclosure may facilitate separating of the respective geometric features of the hub component 31 and the catheter adapter 18.

Figure 15A:
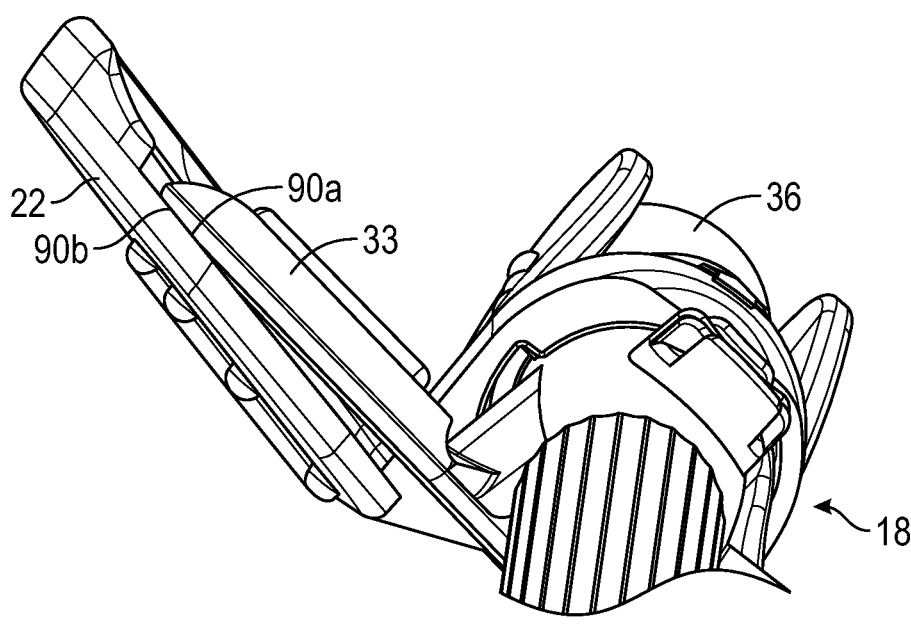
FIG. 15A is a front view of example interface surfaces, according to some embodiments.
Figure 15B:
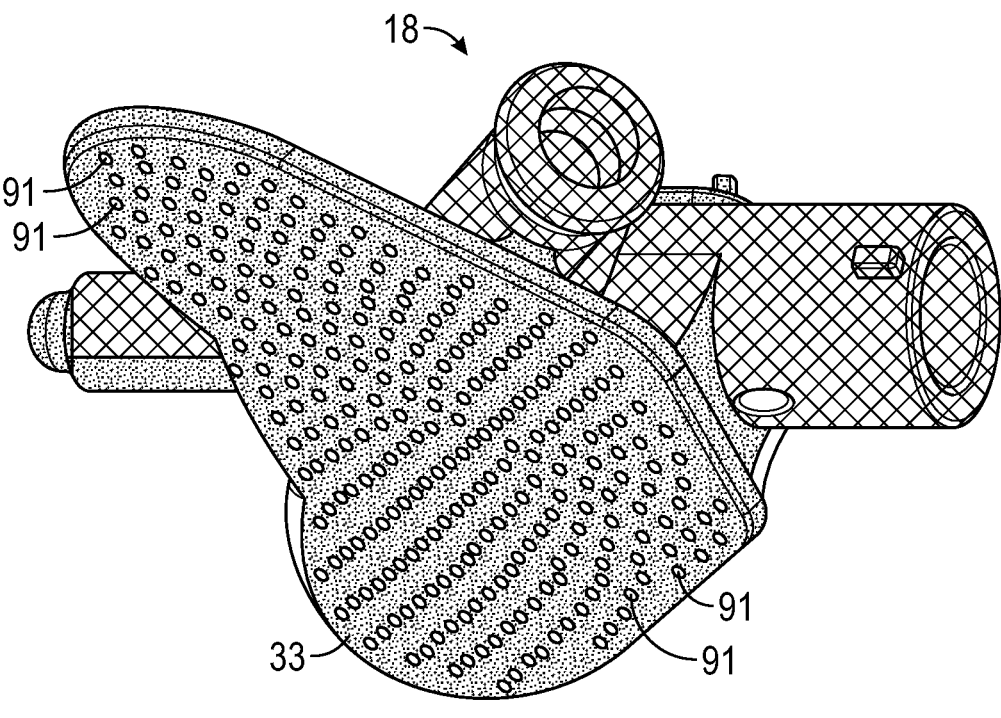
FIG. 15B is a lower perspective view of example protrusions disposed on an example interface surface, according to some embodiments.

Referring now to FIGS. 15A-15B, in some embodiments, the interface between the wing 22 and the wing 33 may allow easy and efficient part separation under a range of potential pinch forces. This separation ease may be accomplished through various technological means. For example, materials used to create interface surfaces 90 on the wing 22 and/or the wing 33 may be modified on the bulk level (e.g., pre-pellet) to include additives or chemical compound modifiers designed to enhance a specific effect. In some embodiments, the interface surfaces 90 may include surfaces of the wing 22 and/or the wing 33. In some embodiments, interface surfaces 90a of the wing 33 may contact or interface with interface surfaces 90b of the wing 22 (the interface surfaces 90a and the interface surfaces 90b may be referred to collectively herein as "interface surfaces 90"). In some embodiments, the interface surface 90a may interface with or contact the interface surface 90b when the catheter system 10 is in an insertion configuration for insertion into the patient.

In some embodiments, the interface surfaces 90 may include a lower surface of the wing 33 and an upper surface of the wing 22. In some embodiments, the second material on the catheter adapter 18 may be modified to increase lubricity against a co-polyester mating component. This may be a preferred approach due to the elimination of at least one additional manufacturing operation. Additionally, product-to-product functional variation may be reduced.

As another example, contact surfaces on the respective interface surfaces 90 may be geometrically modified to improve certain characteristics such as effective coefficients of friction. In some embodiments, contact surfaces of the interface surfaces 90 may be textured on the micro or nano scale; the interface surfaces 90 may contain geometric patterns in forms and depths that provide ideal interface characteristics. In these and other embodiments, a micro-scale texture may be applied to one or more of the interface surfaces 90. This modification represents only one of many possible modifications.

As a further example, a third material may be added to one or more of the interface surfaces 90 to serve as an agent in reducing variables such as coefficient-of-friction. The third material may take many forms. In some embodiments, the third material may include one or more powders, such as, for example, talc or starch. In some embodiments, the third material may include one or more lubes that may be used in different phase states. In some embodiments, the third material may include one or more additive mechanical components such as, for example, a tape or similar adhesive component. In some embodiments, the third material may include one or more insert-molded components.

As yet another example, a geometry on one or both of the interface surfaces 90 may contain features to accept and promote force vectors in a direction of separation. The interface surfaces 90 may take many forms but they may be generally opposed in the assembly layout to ease separation difficulty.

With regard to the specifics of the interface between the wing 22 and the wing 33, any reasonable material combination may be used to improve or highlight certain characteristics. In some embodiments, the interface surfaces 90 may be constructed using polymers. In some embodiments, materials utilized to construct the interface surfaces 90 may include one or more of the following: polycarbonate, co-polyester, polyester, polypropylene, acrylonitrile butadiene styrene (ABS), acetal, polyethylene, nylon, any of the various sub-categories of thermoplastic elastometers (TPE), silicones, and other suitable materials. In some embodiments, the third material may be applied on top of the material utilized to construct the interface surfaces 90.

In some embodiments, a sub-component may be insert-molded into one or both of the interface surfaces 90. In some embodiments, the sub-component may be metallic, polymeric or ceramic or a combination of these classifications. In some embodiments, the sub-component may include intentional surface modifications such as texturing on a certain size scale. Referring now to FIG. 15B, in some embodiments, the sub-component may include protrusions 91 and/or grooves. In some embodiments, the protrusions 91 may be disposed on the interface surface 90a and/or additional portions of the bottom of the securement platform 26, which may contact skin of the patient or the hand of the user.

In some embodiments, the material used to create the securement platform 26, which may include the wing 33, may be modified at the bulk level to improve characteristics related to the interface, which may include a wing-to-wing interface. As illustrated in FIG. 15B, in some embodiments, one or more of the interface surfaces 90 may include surface texture variation to reduce a coefficient of friction between the interface surfaces 90 during separation. In some embodiments, the third material may be applied on one or more of the interface surfaces 90.

Figure 15C:
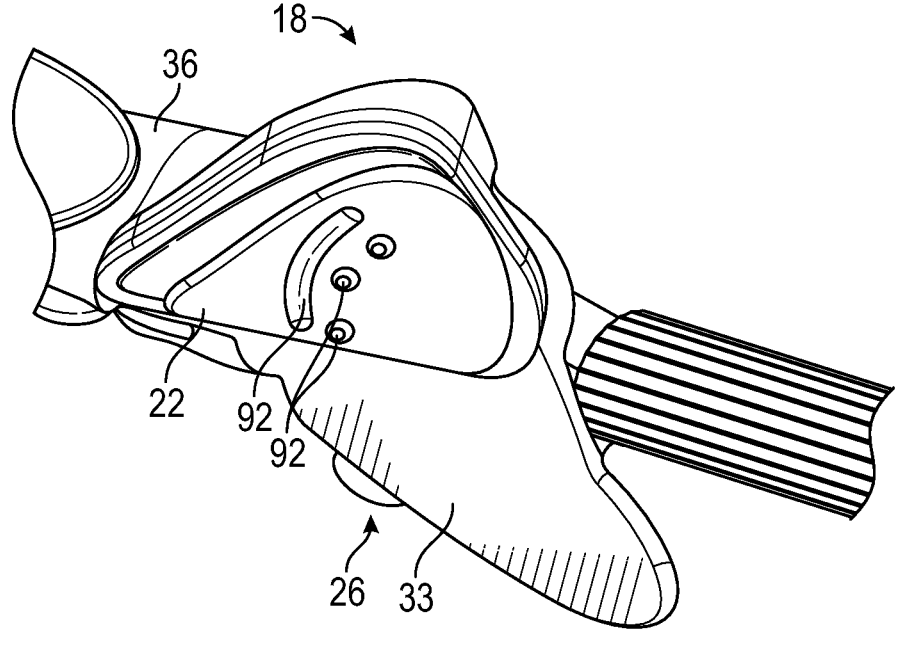
FIG. 15C is a lower perspective view of example geometry features, according to some embodiments.
Figure 15D:
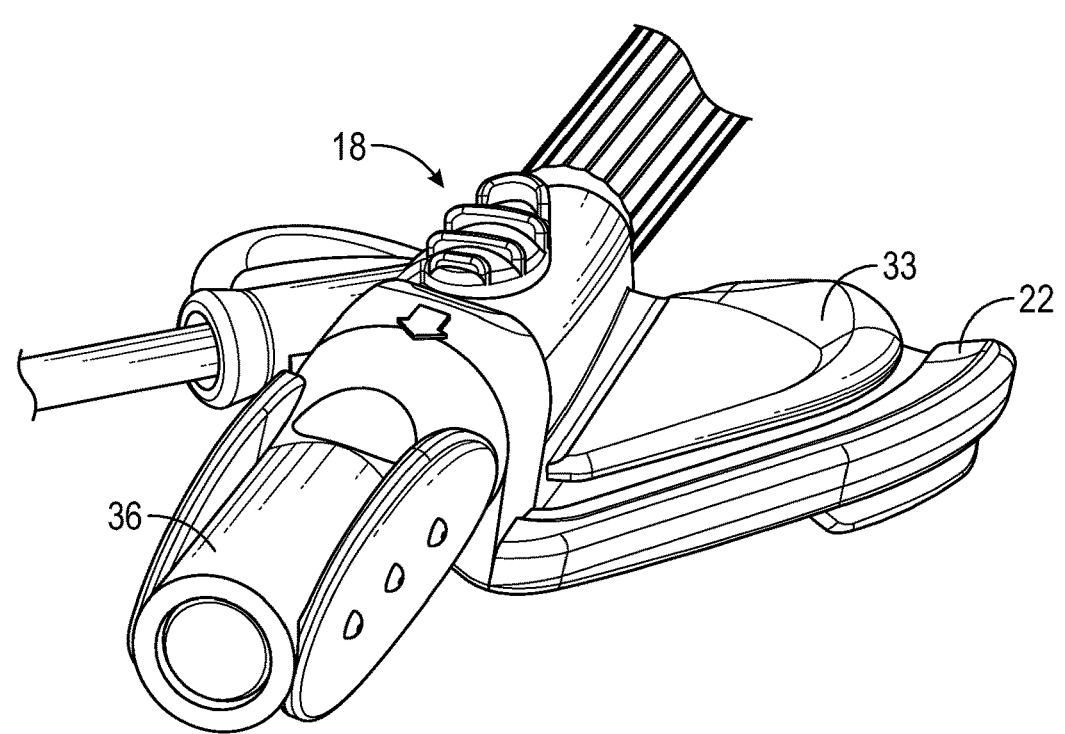
FIG. 15D is an upper perspective view of example wings prior to separation, according to some embodiments.
Figure 15E:
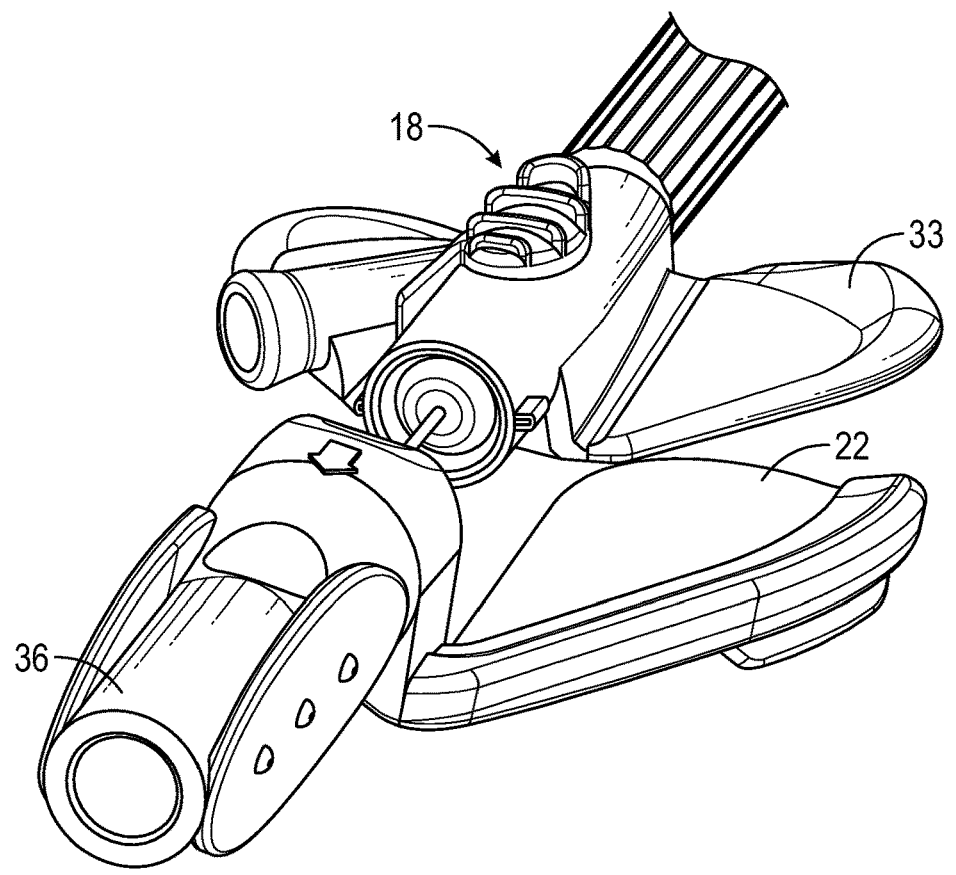
FIG. 15E is an upper perspective view of the example wings of FIG. 15D after separation, according to some embodiments.

Referring now to FIG. 15C, in some embodiments, one or more geometry features 92 may be disposed on a surface configured to contact a hand of the user and/or the skin of the patient, such as a bottom surface of the wing 22, for example. In some embodiments, the geometry features 92 may include protrusions or indents. In some embodiments, the geometry features 92 may promote force vectors in the direction of separation. The geometry features 92 may include various shapes and sizes. In some embodiments, the geometry features 92 may be placed in opposing locations to ease separation difficulty. FIGS. 15D-15E illustrate the wing 22 and the wing 33 prior to and after separation, respectively, according to some embodiments.

In some embodiments, the catheter system 10 may combine a robustly-stabilized catheter adapter 18 with benefits of a winged grip insertion technique. In some embodiments, the interface surfaces 90 between the wing 33 and the wing 22 may enable a more efficient, single-handed separation and withdrawal opportunity. In some embodiments, while pinching the overlapping wings 33, 22, moving the fingers involved in the pinch in opposite directions parallel or near-parallel with a central axis of the catheter 20 may quickly and efficiently initiate cannula withdrawal.

In some embodiments, the securement platform 26 may be added to an integrated catheter (e.g, BD NEXIVA™ Closed IV Catheter System) as a step toward an improved product experience for patients. In some embodiments, the securement platform 26 is compatible with a "central grip" insertion style and/or to some degree a "ported grip" insertion style. The "winged grip" insertion style is not accounted for in the current state-of-the-art. In some embodiments, addition of the wing 22 below the wing 33 results in an improved integrated catheter for users who prefer the winged grip insertion technique. In some embodiments, the wing 22 disposed below the wing 33, and having the wing 22 and the wing 33 slidable with respect to each other, enables a product with a similar insertion experience to a traditional winged product such as, e.g., BD INTIMA II™ IV Catheter, along with the patient benefits of a securement platform 26.

In some embodiments, the interface surfaces 90 may be de-coupled and/or slid past each other in a quick and controlled manner as soon as the initial insertion concludes. The ease of de-coupling is critical and one or more of the following techniques may be employed to optimize this ease of de-coupling: modification of a bulk material(s) used for construction of the interface surfaces 90 via introduction of a compounded additive; surface texture variation on one or more areas of one or more of the interface components; addition of a component or medium such as a lube or tape applied to one or more areas of one or more of the interface surfaces 90; and creation of geometry to minimize finger-based pinch force vector application perpendicular or near-perpendicular to the primary direction of part separation.

In some embodiments, the catheter adapter 18 may include one or more particular wings 33 that may be somewhat symmetrically-placed relative to a longitudinal axis of the catheter 20. In some embodiments, the wings 33 may create a seamless securement platform 26 to rest against the patient's skin. In some embodiments, the securement platform 26 may include a lower-durometer material relative to a material of the hub component 31 and a material of a body of catheter adapter 18 through which a lumen may extend. In some embodiments, the lower-durometer material may be in the range of 50 A to 95 A durometer.

In some embodiments, the hub component 31 may include the wing 22 asymmetrically opposed to the extension tube port on the catheter adapter 18. In some embodiments, the wing 22 may be constructed of a harder, stiffer material relative to the securement platform 26 of the catheter adapter 18. In some embodiments, the wing 22 includes geometry for gripping with the fingers of the right hand.

Figure 15F:
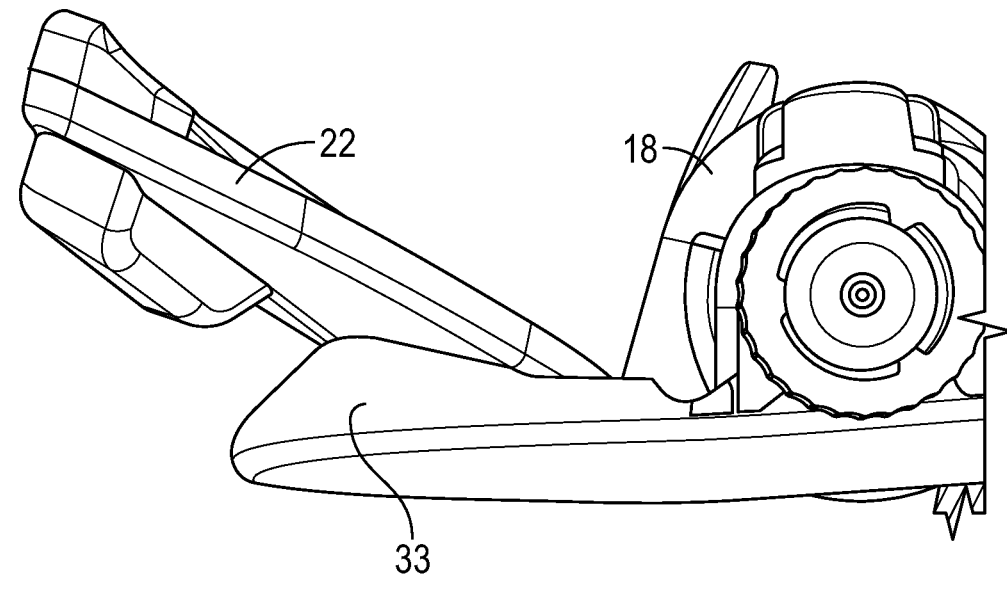
FIG. 15F is a rear view of a portion of another example catheter adapter, illustrating a rotating example grip.

In some embodiments, in a fully-assembled configuration, the wing 33 nests directly against the profile of the wing 22. In some embodiments, in the context of typical gripping orientations and forces, very little deformation may occur in the wing 33 due to the load transfer through the stiffer wing 22. Referring now to FIG. 15F, in some embodiments, the hub component 31 may rotate around the catheter axis relative to the catheter adapter 18 to accommodate certain insertion grip styles. In some embodiments, under pinch-based force application, the overlapping wings 22, 33 captured in the pinch enable a stiffer system for an improved insertion. In these and other embodiments, the wing 22 may rest on top of the wing 33 as opposed to the wing 33 resting on top of the wing 22. In these embodiments, the thumb of the user may contact or rest on top of the wing 22 and may move proximally in order to hood the cannula 16 and/or withdraw the needle hub 12 from the catheter adapter 18.

In some embodiments, when the user is ready to withdraw the cannula 16, the fingers of the right hand used to pinch the wing 22 and the wing 33 are moved in an opposing direction near-parallel to the axis of the catheter 20. Typically the thumb will move distally along with the wing 33 while the opposing finger (the forefinger in some cases) moves proximally along with the wing 22. In some embodiments, the wing 22 and the wing 33 may move relative to each other with a coefficient of friction of approximately 0.2 in a preferred range of 0.1 to 0.5. In some embodiments, the coefficient of friction may range from approximately 0.1 to 1.0 depending on, for example, markets and target performance characteristics. In some embodiments, the coefficient of friction may range from 0.1 to 1.5.

In some embodiments, the wing 33 may rest on a top surface of the wing 22. In some embodiments, the thumb may contact the wing 33. In some embodiments, at a time of withdrawal, the catheter adapter 18 moves distally with respect to the hub component 31. In some embodiments, the hub component 31 rotates in a range of 0 to 45 degrees around the catheter axis relative to the catheter adapter 18. In some embodiments, the durometer of the wing 33 is approximately 70 A.

In some embodiments, the interface surfaces 90 between the wing 33 and the wing 22 may include medial and/or lateral locations of the catheter system 10. Additionally or alternatively, in some embodiments, the interface surfaces 90 may include central locations. In some embodiments, the interface surfaces 90 may include elements of the catheter system 10 other than the wing 33 and the wing 22. In some embodiments, a particular interface surface 90, such as, for example, the wing 33, may reside against a bottom surface of the wing 22.

In some embodiments, mechanics of the wing 33 and the wing 22 geometry and the unique catheter system 10 layout may be rooted in usability studies. Separating the catheter adapter 18 from the hub component 31 at the conclusion of the initial insertion into the vasculature of the patient behaves largely according to the $F=\mu N$ equation where F represents the force required to separate the components, $\mu$ represents the effective coefficient of friction between the wing 33 and the wing 22, and N represents the surface normal force generated by pinching.

In some embodiments, $\mu$ may be reduced while N may be controlled and directed without introducing excessive cost into the manufacturing and assembly of the catheter system 10. In some embodiments, $\mu$ may be reduced via the material used to create the interface surfaces 90, geometric modifications of the interface surfaces 90 to improve coefficients of friction, and addition of a third material, as previously described, for example. In some embodiments, controlling N may be accomplished by geometries on the interface surfaces 90 to promote force vectors in the direction of separation, as previously described, for example.

In the pursuit of a reduced coefficient of friction, early prototypes utilized scotch tape as a surface modifier. The tape was placed on the underside of the wing 33 so that the downward facing, adhesive-free side of the tape interfaced with the wing 22. In this configuration, the coefficient of friction was effectively minimized; the tape worked very well.

Attempts were made to add the tape to the wing 22 instead of the wing 33. In this arrangement the upward-facing, adhesive-free side of the tape interfaced directly with the underside of the wing 33. This configuration did not yield any notable reduction in the coefficient of friction. This was a surprising result.

The same experiments were performed substituting various lubes in place of the tape. Similar results occurred with lubes. Applying the lube directly to the underside of the wing 33 may yields a better reduction in coefficient of friction relative to a lube application on the wing 22. The wing 33 was notably lower in durometer than the wing 22 for these evaluations.

Methods for coupling catheter adapters 18 to septum sub-assemblies, which may include the septum 66 and/or a septum canister, may include press fits, snapping, adhesive bonding, welding, etc. Secure attachment between the catheter adapter 18 and the septum sub-assembly may prevent failure of the catheter system 10 under high injection pressures, such as, for example, 300 psi. However, processes such as bonding and welding may add cost and complexity to the manufacturing process, and snapping may typically be used as an assembly method.

Figure 16A:
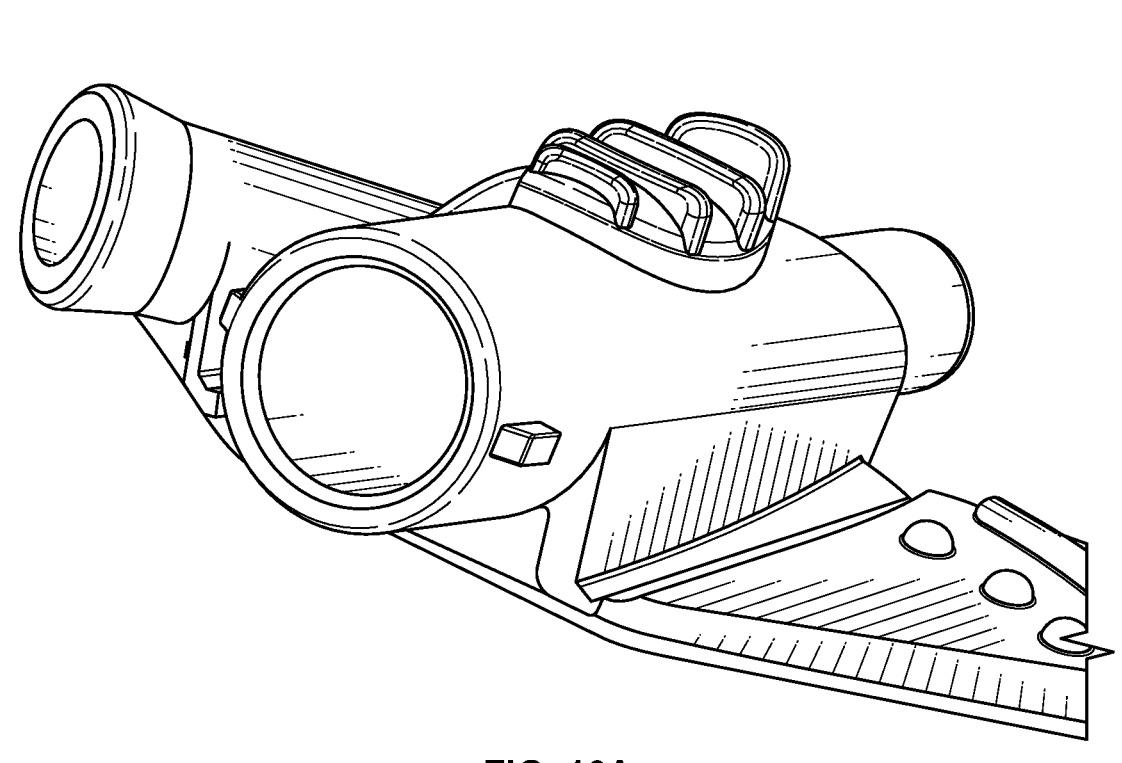
FIG. 16A is an upper perspective view of an example catheter adapter without stabilization ribs, according to some embodiments.
Figure 16B:
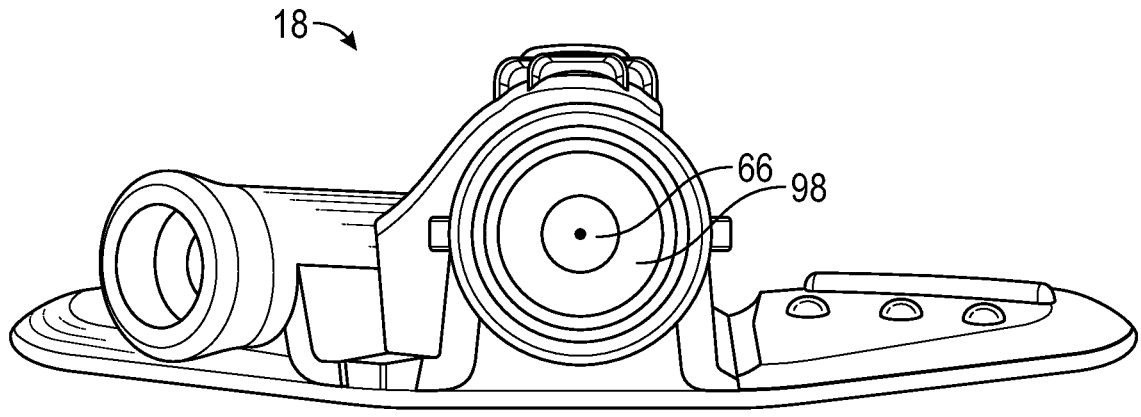
FIG. 16B is a rear view of the catheter adapter of FIG. 16A, according to some embodiments.

Referring now to FIGS. 16A-16B, FIG. 16A illustrates the catheter adapter 18 without any stabilization ribs, according to some embodiments, and FIG. 16B is a rear or proximal view of the catheter adapter 18 of FIG. 16A. In some embodiments, the catheter adapter 18 includes the septum 66, which may be disposed within a septum canister 98.

Figure 17A:
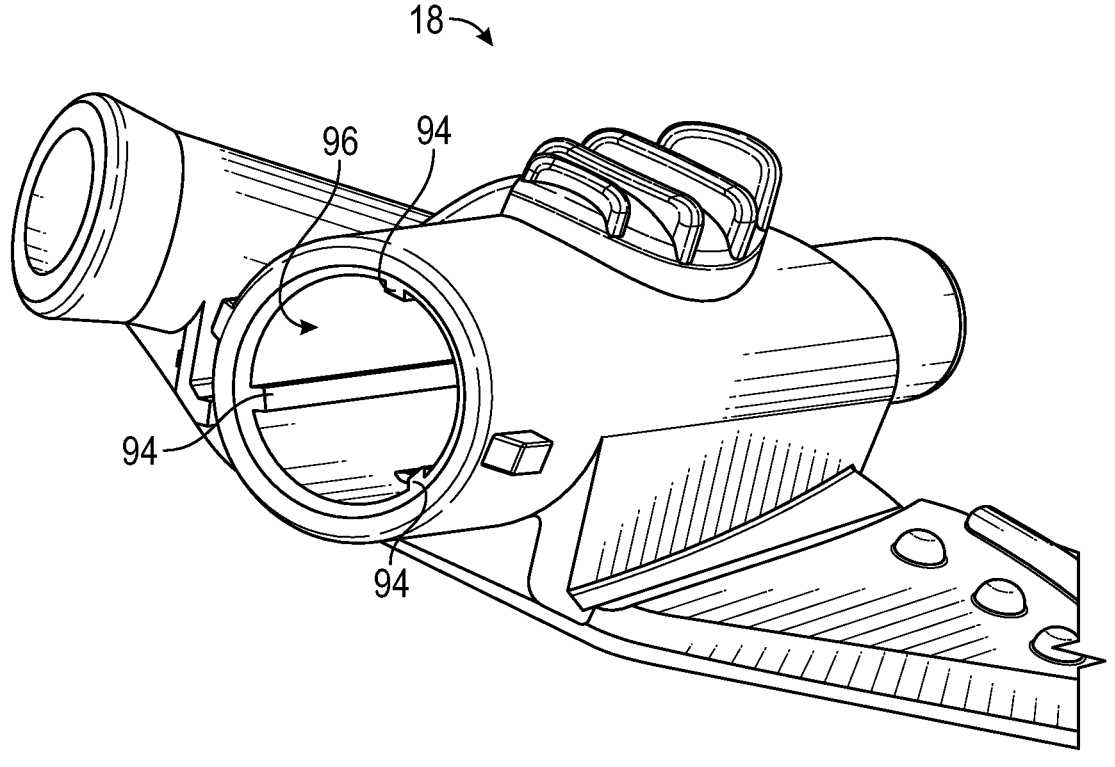
FIG. 17A is an upper perspective view of an example catheter adapter with example stabilization ribs, according to some embodiments.
Figure 17B:
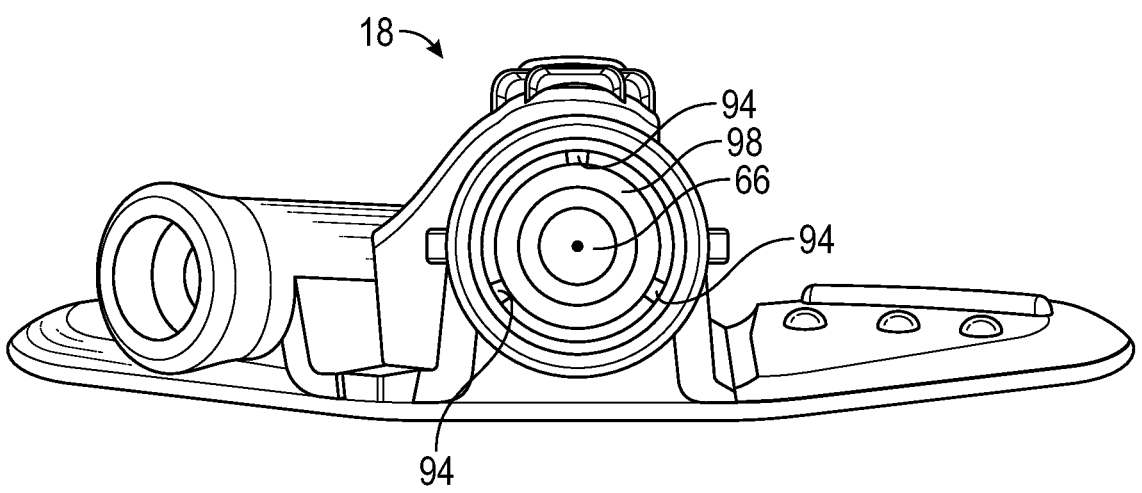
FIG. 17B is a rear view of the catheter adapter of FIG. 17A, according to some embodiments.

Referring now to FIGS. 17A-17D, FIG. 17A illustrates the catheter adapter 18 with one or more stabilization features, such as, for example, stabilization ribs 94, according to some embodiments. FIG. 17B is a rear view of the catheter adapter 18 of FIG. 17A. In some embodiments, the stabilization ribs 94 may stabilize and prevent rocking of the septum canister 98 containing a septum 66. In some embodiments, the stabilization ribs 94 may be aligned with the central axis of the catheter adapter 18. In some embodiments, the stabilization ribs 94 may be disposed at the proximal and/or distal ends of the catheter adapter 18. In some embodiments, the stabilization ribs 94 may extend along a portion of a length of the inner wall of the catheter adapter 18. In some embodiments, the stabilization ribs 94 may extend from a proximal end to a distal end of the catheter adapter 18. In some embodiments, the stabilization ribs 94 may be generally linear. In some embodiments, the stabilization ribs 94 may be disposed within a lumen 96 of the catheter adapter 18. In some embodiments, the stabilization ribs 94 may be replaced by other suitable protrusions.

Figure 17C:
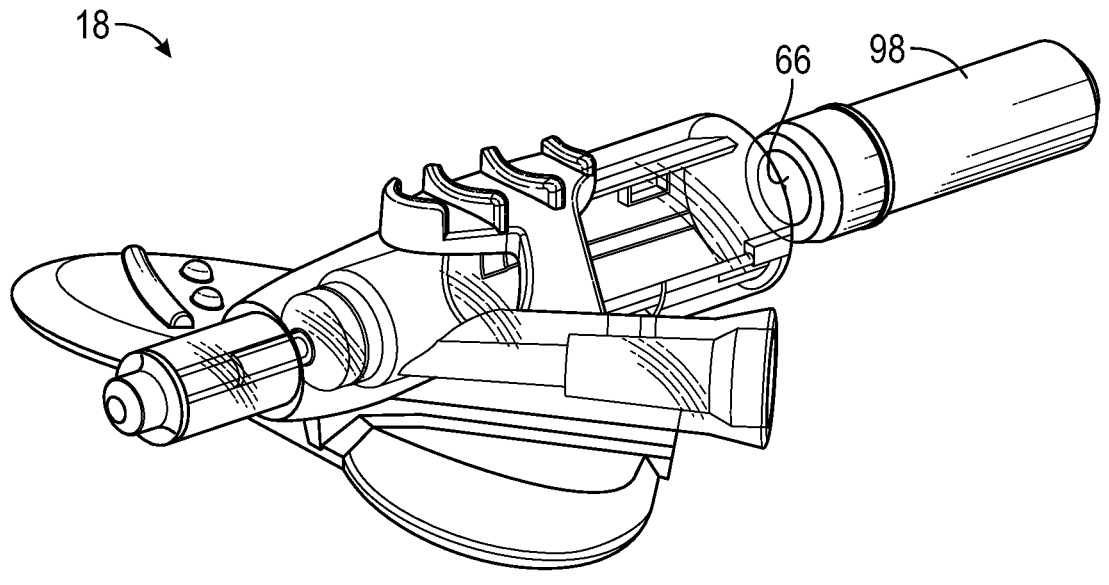
FIG. 17C is an upper perspective view of the catheter adapter of FIG. 17A, illustrating an example septum canister and example septum removed from the catheter adapter, according to some embodiments.
Figure 17D:
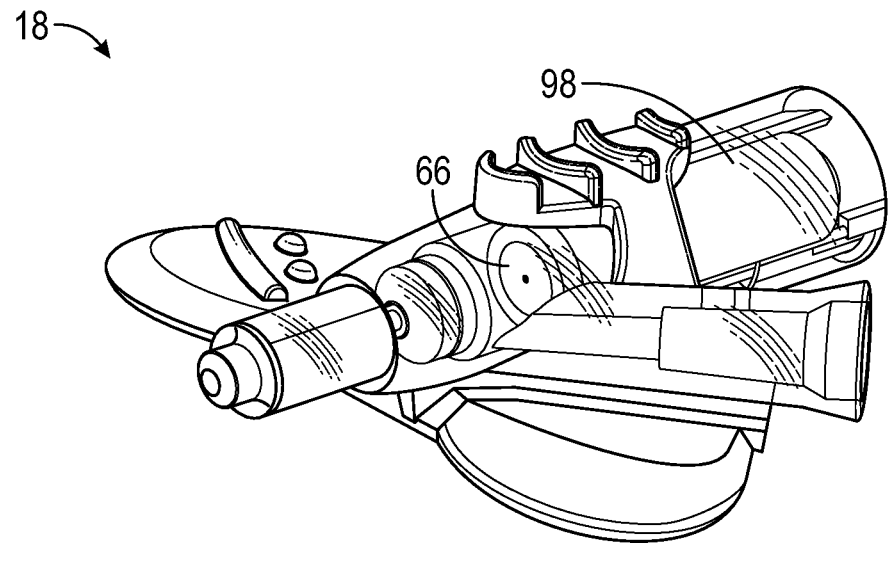
FIG. 17D is an upper perspective view of the catheter adapter of FIG. 17A, illustrating the septum canister and the septum secured within the catheter adapter, according to some embodiments.

FIG. 17C illustrates an exploded view of the catheter adapter 18 and a septum sub-assembly that includes the septum canister 98 and the septum 66. FIG. 17D illustrates an upper perspective view of the septum sub-assembly inserted in the proximal end of the catheter adapter 18. In some embodiments, the septum 66 may include any number of pieces. In some embodiments, the septum 66 may be a one-piece septum or, as illustrated, for example, in FIG. 18A, a two-piece septum 66.

In some embodiments, the catheter adapter 18 that includes the stabilization ribs 94 may enable a robust snap-fit between the catheter adapter 18 and the septum canister 98. In some embodiments, welding, bonding, or other securement methods may be used in addition to the stabilization ribs 98, which may increase a stability of the septum canister 98 within the catheter adapter 18.

Figures 18A, 18B:
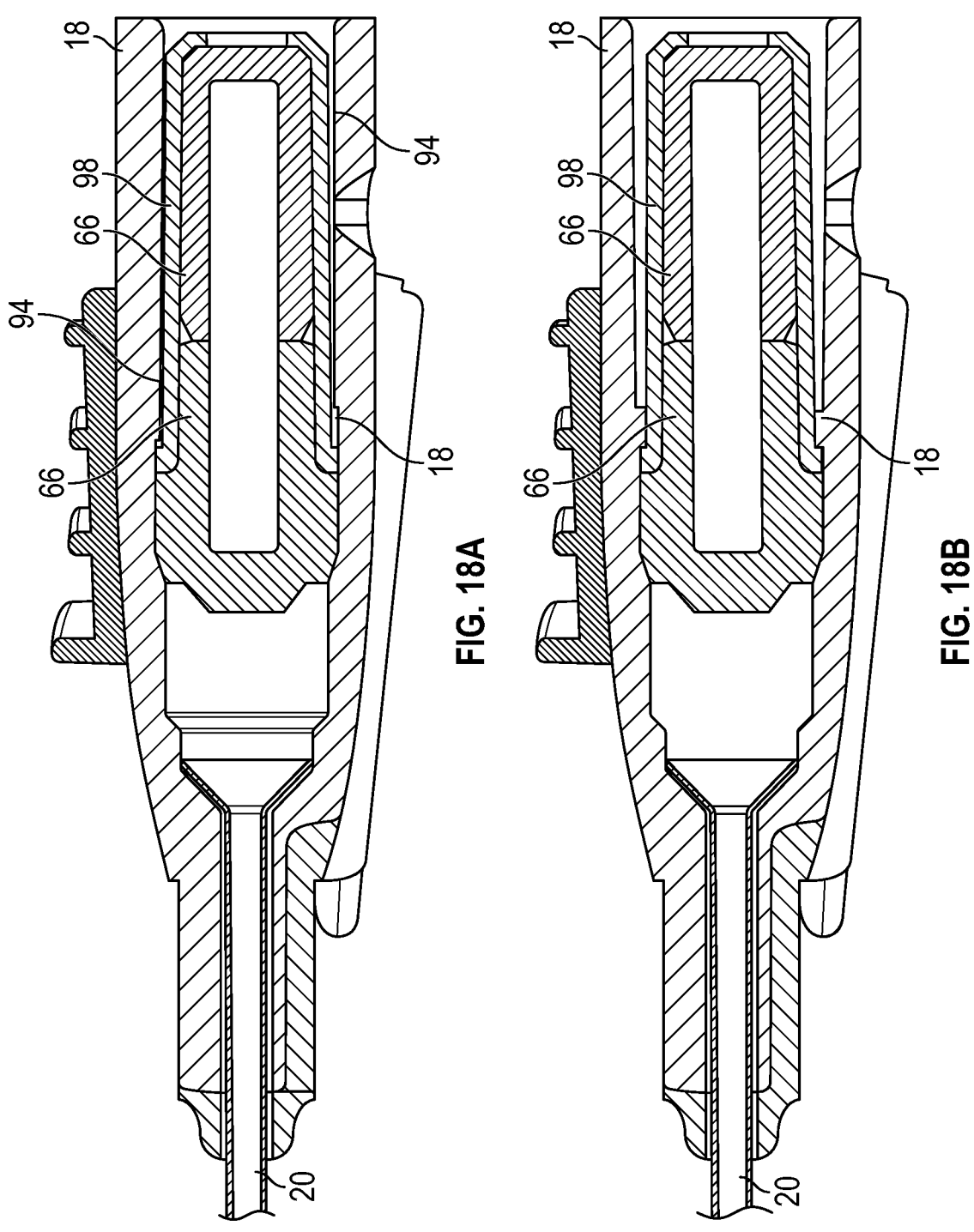
FIG. 18A is a cross-sectional view of the catheter adapter of FIG. 16A, according to some embodiments.
FIG. 18B is a cross-sectional view of the catheter adapter of FIG. 17A, according to some embodiments.

Referring now to FIGS. 18A-18B, a comparison between the catheter adapter 18 with stabilization ribs 98 (e.g., FIG. 18A) and the catheter adapter 18 without ribs 98 (e.g., FIG. 18B) is illustrated, according to some embodiments. In some embodiments, the stabilization ribs 98 may facilitate a reduced gap between an inner wall of the catheter adapter 18 and the septum canister 98. In some instances, a larger gap between the inner wall and the septum canister 98 may result in increased radial displacement and increased potential for the septum canister 98 to become unsnapped when forced off axis due to eccentric loading, for example.

In some embodiments, the stabilization ribs 94 provide securement of the septum canister 98 while providing easy extraction from a core pin during manufacturing. In some embodiments, stresses may be radial only for a short under-cut, then deformation due to the core pin may take a shape.

In some embodiments, the stabilization ribs 94 may be molded in a soft second short, such as, for example, from a thermoplastic elastomer ("TPE") resin. This may allow a relatively low-stress press fit between the catheter adapter 18 and the septum canister 98, with little or no clearance between the inner wall of the catheter adapter 18 and the septum canister 98.

Figure 19A:
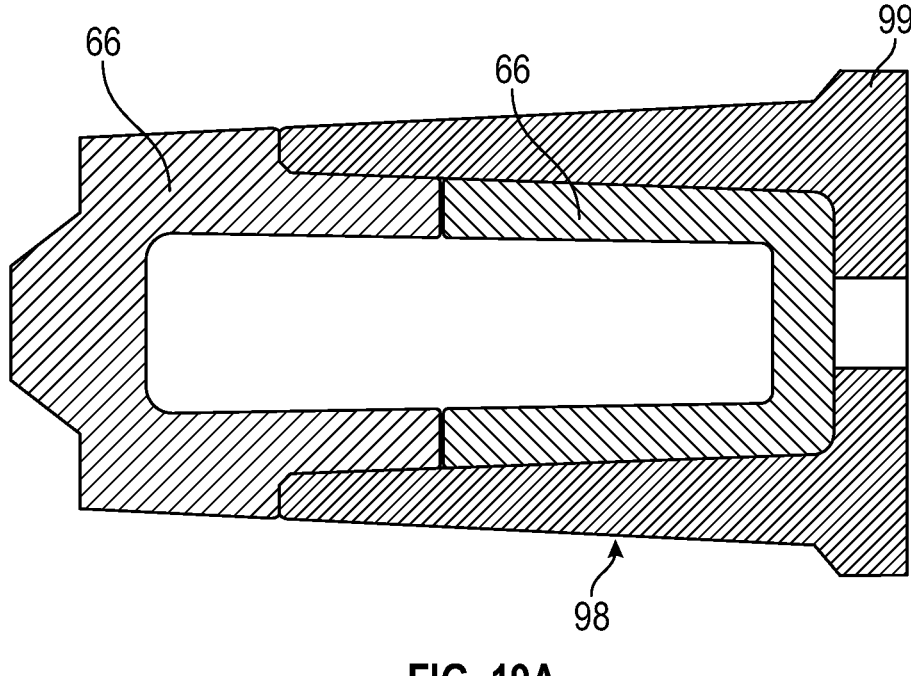
FIG. 19A is a cross-sectional view of an example septum canister, according to some embodiments.
Figure 19B:
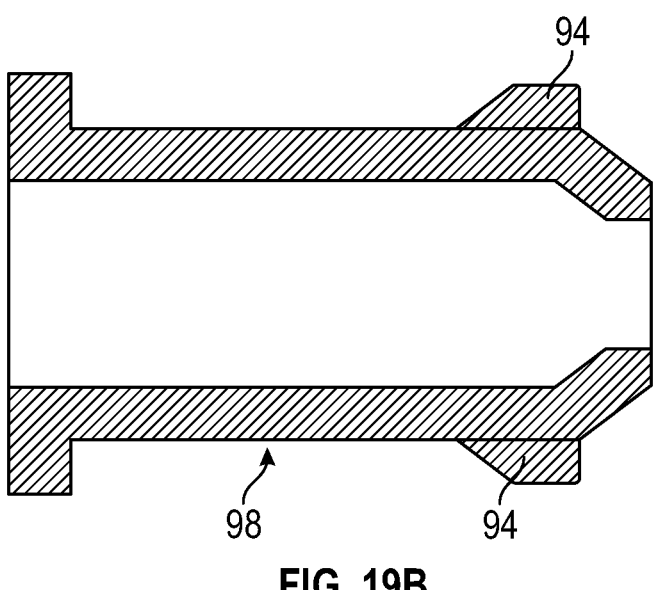
FIG. 19B is a cross-sectional view of another example septum canister coupled with an example septum, according to some embodiments.

Various types of septum canisters 98 may be used. In some embodiments, the septum canister 98 may correspond to the septum canister 98 currently used in the BD NEXIVA™ and BD PEGASUS™ products. FIGS. 19A and 19B illustrate example septum canisters 98, according to some embodiments. Referring to FIG. 19A, in some embodiments, a proximal end of the canister 98 may include a snap flange 99 or other snap feature that may snap into the catheter adapter 18. In some embodiments, the snap flange 99 may be annular. In some embodiments, a draft on the inner wall of the catheter adapter 18 may be compensated for by a taper in the canister 98 along a length of the canister 98. In some embodiments, because the snap flange 99 may be close to the proximal end of the catheter adapter 18, an undercut in molding may be very short, making the adapter core pin easier to extract. In some embodiments, the septum canister 98 illustrated in FIG. 19A may be molded in a simple "open and shut" mold configuration.

Referring now to FIG. 19B, in some embodiments, the snap flange 99 may be disposed at a proximal end of the canister 98. In some embodiments, the snap flange 99 may be disposed at any position along a length of the canister 98 and/or the catheter adapter 18. In some embodiments, one or more other stabilization ribs 94 may be added to take up the clearance between the inner wall of the catheter adapter 18 and the septum canister 98.

Figure 19C:
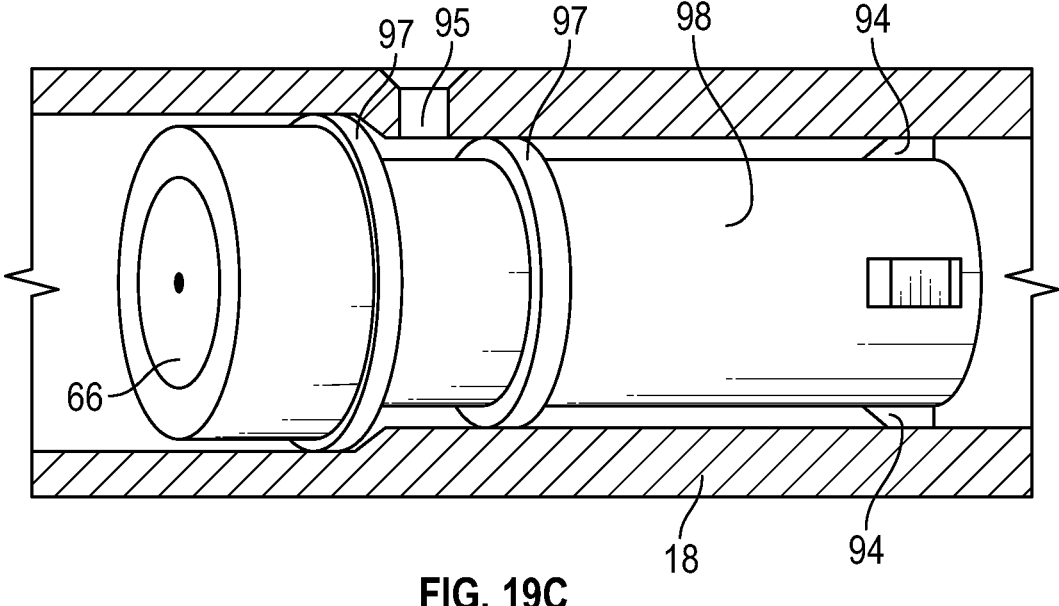
FIG. 19C is a cross-sectional view of another example septum canister disposed within an example catheter adapter, according to some embodiments.

As illustrated in FIG. 19C, in some embodiments, ribs 97 on the septum canister 98 may be disposed on either or both sides of an adhesive port 95 to contain the adhesive and allow annular distribution of the adhesive. In some embodiments, the ribs 97 may direct flow of an adhesive for a full annular bond proximate and/or between the ribs 97.

Various embodiments of the present invention may further comprise a cannula safety mechanism. In some embodiments, the catheter system 10 may include various types of safety mechanisms to provide cannula tip coverage. In some embodiments, a particular safety mechanism may be releasably-joined to the catheter adapter 18 via an external or internal interlock or an interference fit. In some embodiments, the particular safety mechanism may be releasably-joined to the catheter adapter 18 with an external or internal stability interface.

In some embodiments, the catheter system 10 may include a cannula safety mechanism. In some embodiments, the safety mechanism may include any safety mechanism configured to secure a sharpened, distal tip of the cannula 16, which may include an introducer needle, when the cannula 16 is withdrawn from a catheter 20 of the particular catheter device, preventing accidental needle sticks.

The safety mechanism may be coupled with the catheter system 10 in any number of ways. In some embodiments, the safety mechanism may include an internal interlock in which the safety mechanism is coupled with an internal surface of a catheter adapter 18. Coupling may include threading, fitting, snapping, connecting, attaching, fastening, clipping, hooking, or any other suitable means of coupling. Non-limiting examples of safety mechanisms that include an internal interlock are provided in: U.S. Pat. No. 8,496,623, titled BI-DIRECTIONAL CANNULA FEATURE CAP-TURE MECHANISM, filed Mar. 2, 2009; U.S. Pat. No. 9,399,120, titled BI-DIRECTIONAL CANNULA FEA-TURE CAPTURE MECHANISM, filed Jul. 11, 2013; U.S. Patent Application No. 62/314,262, titled CANNULA CAP-TURE MECHANISM, filed Mar. 28, 2016, each of which is herein incorporated by reference in its entirety. In some embodiments, the safety mechanism may include a clip disposed within the catheter adapter, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the safety mechanism may include an external interlock in which the safety mechanism is coupled with an external surface of the catheter adapter 18. In some embodiments, the safety mechanism may be coupled with an external surface of the catheter adapter 18 and an internal and/or external surface of a needle hub 12. Coupling may include threading, fitting, snapping, connect-ing, attaching, fastening, clipping, hooking, or any other suitable means of coupling. Non-limiting examples of safety mechanisms that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAV-ING EXTERNAL NEEDLE SHIELD AND INTERNAL BLOOD CONTROL SEPTUM, filed Jun. 4, 2014, which is herein incorporated by reference in its entirety. The V-clip may selectively retain a portion of the catheter adapter.

In some embodiments, a defeatable mechanical connec-tion is provided between the safety mechanism and at least one other component of the catheter system 10. In some instances, the mechanical connection is defeated upon securement of the distal tip of the cannula 16 within the safety mechanism. In some embodiments, a surface of the safety mechanism is selectively coupled to one or more of the following: the catheter adapter 18, a blood control valve, an extension tube, and the grip 14.

In some embodiments, the safety mechanism may include a safety barrel, which may be spring-loaded. For example, the safety barrel may be spring loaded as in the BD™ Insyte® AUTOGUARD™ BC shielded protective IV cath-eter. In some embodiments, the safety mechanism may be passively and/or actively activated. In some embodiments, the safety mechanism may be configured to interact with a needle feature, such as a ferrule, notch, crimp or bump on the needle. In some embodiments, the safety mechanism may include an arm or lever that may be actuated to capture the distal tip within the safety mechanism and prevent the tip from emerging prior to safe disposal. In some embodiments, the safety mechanism may be attached to a body of the needle and may be capable of sliding along the length thereof.

In some embodiments, in an assembled position prior to catheterization, the safety mechanism may be disposed between the catheter adapter 18 and the needle hub 12. In some embodiments, the catheter adapter 18 and the needle hub 12 may be spaced apart by at least a portion of the safety mechanism in the assembled position prior to catheteriza-tion. In some embodiments, in the assembled position prior to catheterization, a proximal end of the catheter adapter 18 may be disposed between a distal end of the safety mecha-nism and a distal end of a grip 14 of the hub component 31, such as, for example, a paddle grip. In some embodiments, in the assembled position prior to catheterization, the proxi-mal end of the catheter adapter 18 body may be disposed between the distal end of the safety mechanism and a proximal end of the grip 14 of the needle hub 12. In some embodiments, a portion of the safety mechanism may over-lap with a portion of the grip 14 of the needle hub 12. In some embodiments, at least a portion of at least one of the catheter adapter 18 and the grip 14 overlaps at least some portion of the safety mechanism. In some embodiments, no portion of the catheter adapter 18 or the grip 14 overlaps any portion of the safety mechanism.

In any of the above described embodiments, the compo-nents of the securement platform 26 may be formed of the same material by injection molding or other processes. This material may be an elastomeric or other low-durometer material that is relatively gentle against the patient's skin and/or dressings used to keep the catheter component in place during fluid delivery. For example, some embodiments of the present invention comprise a low-durometer material having a durometer hardness of from approximately 30 Shore A to approximately 90 Shore D. In some embodi-ments, a low-durometer material may include a durometer hardness of from approximately 50 Shore A to approxi-mately 90 Shore D. In some embodiments, the components of the securement platform 26 may be formed of a thermo-plastic elastomer (TPE) or the like.

All examples and conditional language recited herein are intended for pedagogical objects to aid the reader in under-standing the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

We claim:

1. An IV catheter system, comprising:

a catheter adapter having a proximal end, a distal end, and a lumen extending through the proximal end and the distal end, wherein the catheter adapter further comprises an annular wall extending between the distal end and the proximal end and forming the lumen, wherein a first portion of the annular wall at the proximal end of the catheter adapter is constructed of a first material and a second portion of the proximal end of the annular wall is constructed of a second material, wherein the second portion comprises a notch proximate the first portion, the notch having a width and a length longer than the width, wherein the length of the notch is generally parallel with a longitudinal axis of the catheter adapter, the notch extending in a proximal direction to a proximal-most surface of the proximal end of the catheter adapter, wherein the first portion and the second portion are proximate the lumen, wherein the second material has a lower durometer than the first material.

2. The IV catheter system of claim 1, wherein the notch forms a bottom portion of an outer circumference of the annular wall configured to be closest to skin of a patient.

3. The IV catheter system of claim 1, further comprising a septum disposed within the lumen of the catheter adapter, wherein the notch is proximal to the septum.

4. The IV catheter system of claim 1, wherein the catheter adapter further comprises an outer circumference, wherein the another second portion constructed of the second material and the first portion constructed of the first material are disposed on the outer circumference.

5. An IV catheter system, comprising:

a catheter adapter having a proximal end, a distal end, and an outer circumference, wherein a portion of the catheter adapter is constructed of a first material and another portion of the catheter adapter is constructed of a second material, wherein the second material has a lower durometer than the first material; and a securement platform coupled to the catheter adapter and constructed of the second material, wherein the another portion of the catheter adapter constructed of the second material extends from a proximal end of the securement platform to a proximal-most edge of the catheter adapter, wherein the portion of the catheter adapter constructed of the first material extends to the proximal-most edge of the catheter adapter, wherein the another portion of the catheter adapter comprises a strip forming a bottom surface of the catheter adapter configured to contact skin of a patient, wherein the another portion constructed of the second material and the portion constructed of the first material form the outer circumference at the proximal-most edge, wherein a width of the strip is less than the outer circumference of the catheter adapter.

6. The IV catheter system of claim 5, wherein the strip comprises a first edge, a second edge opposite the first edge, a width extending from the first edge to the second edge, and a length longer than the width and extending from the proximal end of the securement platform, wherein the first material is lateral to the first edge and lateral to the second edge and contacts the first edge and the second edge.

7. The IV catheter system of claim 5, further comprising a septum disposed within a lumen of the catheter adapter, wherein the strip is proximal to the septum.

8. An IV catheter system, comprising:

a catheter adapter having a proximal end and a distal end, wherein a portion of the catheter adapter is constructed of a first material and another portion of the catheter adapter is constructed of a second material, wherein the second material has a lower durometer than the first material, wherein the another portion comprises an indicator feature having a T-shape and disposed on an upper surface of the catheter adapter, wherein the T-shape comprises a stem and a crossbar perpendicular to the stem, wherein both the stem and the crossbar contact an outer circumference of the catheter adapter; and a central push tab feature coupled to the upper surface of the catheter adapter and constructed of the second material, wherein the indicator feature extends in a proximal direction from the central push tab feature.

* * * * *